(12) United States Patent
Khripin et al.

(10) Patent No.: US 9,238,809 B2
(45) Date of Patent: Jan. 19, 2016

(54) COMPOSITIONS, METHODS, AND KITS FOR ISOLATING AND ANALYZING NUCLEIC ACIDS USING AN ANION EXCHANGE MATERIAL

(75) Inventors: Yuri Khripin, Gaithersburg, MD (US); Dirk Loeffert, Hilden (DE); Roland Fabis, Leverkusen (DE); Nadine Krueger, Solingen (DE)

(73) Assignees: QIAGEN GAITHERSBURG, INC., Gaithersburg, MD (US); QIAGEN GMBH, Hilden (DE)

( * ) Notice: Subject to any disclaimer, the term of this patent is extended or adjusted under 35 U.S.C. 154(b) by 305 days.

(21) Appl. No.: 12/851,311

(22) Filed: Aug. 5, 2010

(65) Prior Publication Data
US 2011/0071031 A1 Mar. 24, 2011

Related U.S. Application Data

(60) Provisional application No. 61/231,371, filed on Sep. 24, 2009, provisional application No. 61/295,269, filed on Jan. 15, 2010.

(51) Int. Cl.
*C12Q 1/68* (2006.01)
*C07H 23/00* (2006.01)
*C12N 15/10* (2006.01)

(52) U.S. Cl.
CPC ..... *C12N 15/101* (2013.01); *Y10T 436/143333* (2015.01)

(58) Field of Classification Search
CPC .................................................. C12N 15/101
USPC ...................... 536/23.1, 26.43; 435/6.1, 91.1; 210/634; 422/430
See application file for complete search history.

(56) References Cited

U.S. PATENT DOCUMENTS

| 5,234,809 A | 8/1993 | Boom et al. |
| 5,856,192 A | 1/1999 | Bloch |
| 6,914,137 B2 | 7/2005 | Baker |
| 2009/0275486 A1* | 11/2009 | Kurn et al. ..................... 506/26 |

FOREIGN PATENT DOCUMENTS

| EP | 1 473 299 | 11/2004 |
| WO | 03/101494 | 12/2003 |
| WO | 2004/055207 | 7/2004 |
| WO | 2008/000343 | 1/2008 |

OTHER PUBLICATIONS

International Preliminary Report and Written Opinion based on International Application No. PCT/US2010/044586; issued Mar. 27, 2012 (8 pages).
International Search Report based on PCT/US2010/044586; mailed Jan. 24, 2011 (5 pages).
Zhang et al.: "PCR Microfluidic Devices for DNA Amplification," Biotech Advances; 2006; pp. 243-284; Elsevier Inc.
(Continued)

*Primary Examiner* — Jezia Riley
(74) *Attorney, Agent, or Firm* — Miles & Stockbridge PC

(57) ABSTRACT

The present disclosure relates to methods for isolating, amplifying, and/or analyzing nucleic acids in the presence of an anion exchange material by performing the isolation, amplification and/or analysis step in the presence of at least one anionic compound.

18 Claims, 35 Drawing Sheets

(56) References Cited

OTHER PUBLICATIONS

Partial European Search Report of EP10006062, dated Oct. 22, 2010 (6 pages).
Chen et al., "Supressed anion chromatography using mixed zwitterionic and carbonate eluents," Journal of Chromatography; 2006; pp. 3-11.
Partial International Search Report of PCT/US2010/044586 dated Oct. 27, 2010 (5 pages).
International Search Report and Written Opinion of PCT/US2010/044586 dated Jan. 24, 2011 (15 pages).
Hotchkiss, Jr. et al., "Analysis of Oligogalacturonic Acids with 50 or Fewer Residues by High-Performance Anion-Exchange Chromatography and Pulsed Amperometric Detection," Analytical Biochem.; Feb. 1, 1990; 184(s):200-6.
Tyagi et al., "Use of Automated Chromatography on the Amino Acid Analyzer with Lithium Citrate Buffers to Separate Nucleic Acid Bases, Nucleosides, Nucleotides and Their Precursors," Journal of Biochem Biochemical and Biophysical Methods; Aug. 1979; 1(4):221-6.
European Office Action dated Apr. 22, 2014, issued in Application No. 10 745 497.7-1406.

\* cited by examiner

A 1 2 3 4 5 6 7 8 9 10 11 12 13 14 15 16 17

B 1 2 3 4 5 6 7 8 9 10 11 12 13 14 15 16 17

Fig. 3 - continued -
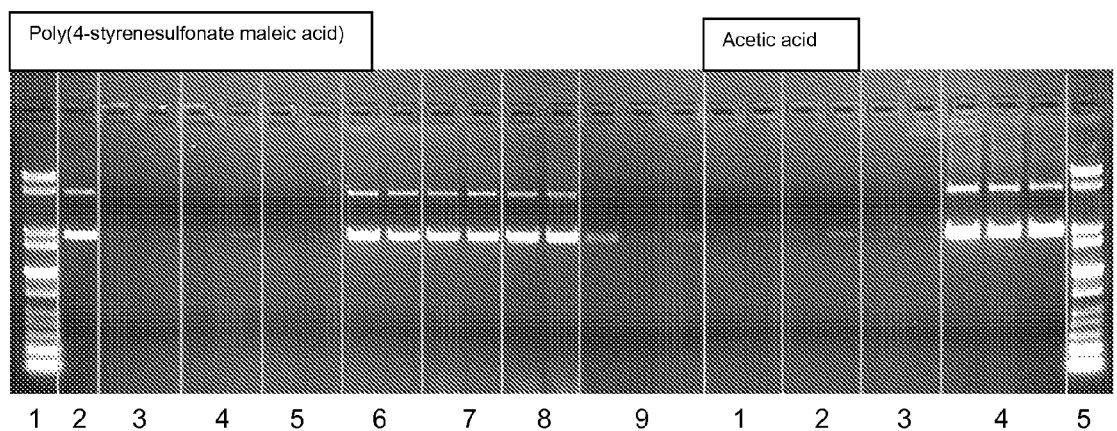
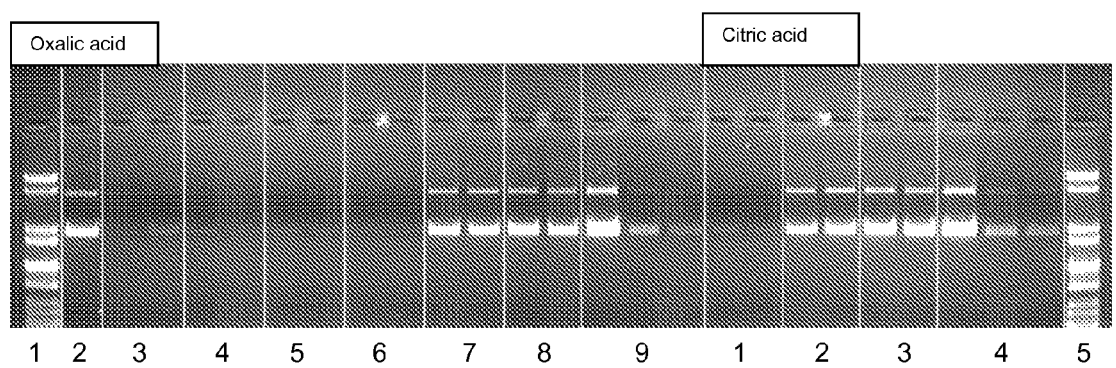

Fig. 3 - continued -
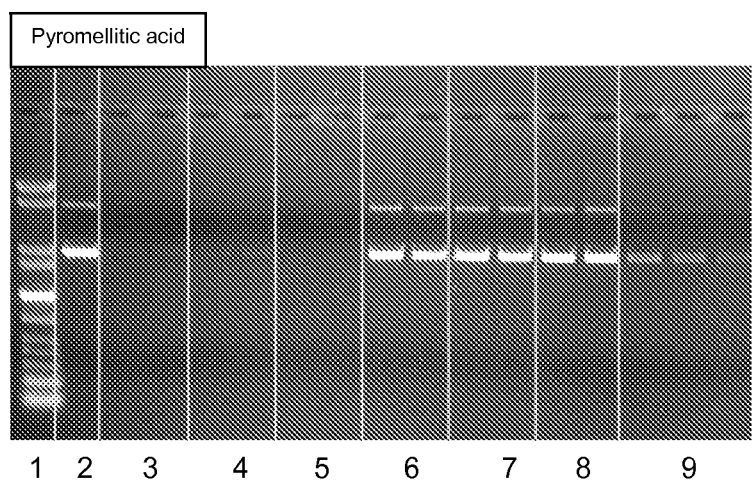
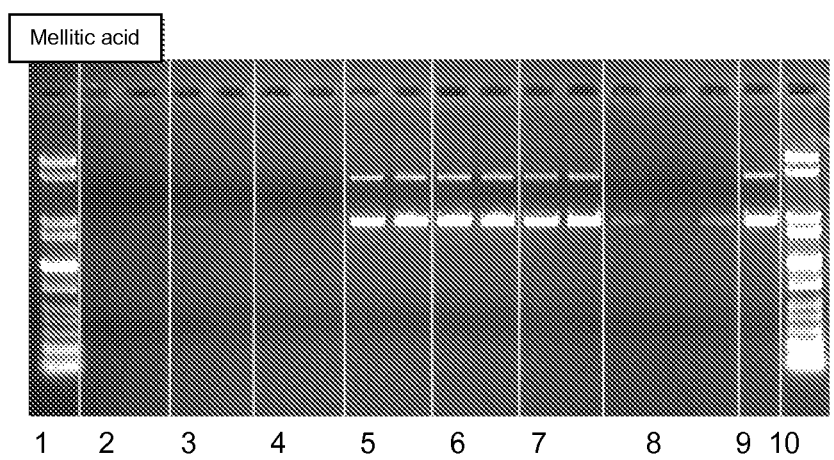

Elution with 0.1% polyacrylic acid

Dilution with 0.1% polyacrylic acid

Elution with 0.125% polyacrylic acid

Dilution with 0.125% polyacrylic acid

COMPOSITIONS, METHODS, AND KITS FOR ISOLATING AND ANALYZING NUCLEIC ACIDS USING AN ANION EXCHANGE MATERIAL

CROSS REFERENCE TO RELATED APPLICATIONS

This application claims priority from U.S. Provisional Patent Application Ser. No. 61/231,371 (filed Aug. 5, 2009), U.S. Provisional Patent Application Ser. No. 61/295,269 (filed Jan. 15, 2010), and European Patent Application Serial No. EP 10006062.3 (filed Jun. 11, 2010), the contents of which are incorporated herein by reference in their entireties. A PCT application entitled "Compositions, Methods, and Kits for Isolating and Analyzing Nucleic Acids Using an Anion Exchange Material" (filed concurrently herewith on Aug. 5, 2010) is also incorporated herein by reference in its entirety.

FIELD OF INVENTION

The present invention relates to methods, compositions, and kits for isolating, eluting, and analyzing nucleic acids using anion exchange materials.

BACKGROUND

Ion-exchange is a process that allows the separation of ions and polar molecules based on the charge properties of the molecules. In principle, ion exchange functions by retaining a target analyte molecules in a stationary phase based on reversible ionic interactions. Typically, the ion exchange composition comprises a stationary phase bearing a capture molecule. Under appropriate buffer and ionic conditions, the capture molecule bears a net charge, the target molecule bears an opposite net charge, while contaminants bear a net neutral charge or a similar net charge to the capture molecule. As a result, the target molecule is retained by the ion exchange composition, while contaminants are removed. The target molecule can then be eluted by neutralizing the charge of the capture or target molecule (e.g. by altering the pH) or treating the composition with another molecule that displaces the target molecule (e.g. by treating with a high salt solution). Such processes are broadly categorized as either cation exchange or anion exchange, depending upon the net charge of the molecule that is being isolated.

Anion exchange is commonly used to purify nucleic acids from complex biological solutions. The nucleic acids can be selectively adsorbed because of their negative charge onto anion exchange resins and then eluted. For low molecular weight nucleic acids, elution buffers typically include salts in high concentrations. Simple organic and inorganic anions have lower selectivity coefficients than nucleic acid, but at high concentrations they can displace nucleic acid from the resins. High molecular weight nucleic acid cannot be eluted by salts because of their extremely high selectivity for the resin. In this case, elution is most often performed by raising the pH, since at high pH weak anion exchange groups of the resin lose their charge.

Thus, elution of nucleic acids from ion exchange resin usually is based on an interrelationship of pH and salt concentration. However, these procedures present some difficulties for downstream processing and analysis of the target nucleic acid. Alkali buffers cannot be used for RNA isolation since RNA is degraded in alkaline solutions. DNA is also alkali-sensitive to some extent, most notably, to the deamination of cytosine (conversion of deoxycytosine into deoxyuracil), especially when heated. Storage of alkali buffers is also problematic, as such solutions are often corrosive, toxic, and have poor shelf stability due to absorbance of $CO_2$ from the air. High salt concentrations that are often employed for elution often interfere with downstream enzymatic reactions such as polymerase chain reaction (PCR), ligation reactions, restriction analysis, cDNA generation or isothermal amplification. Therefore, the resulting nucleic acid eluates need to be desalted, which adds additional handling steps to the nucleic acid isolation procedure and may lead to loss of nucleic acids due to the increased number of handling steps or possible contamination. DNA cannot be directly processed enzymatically because most enzymes are completely denatured under alkaline conditions. Thus, high pH elution also requires additional handling steps because it requires neutralization of the eluate, which further dilutes the eluate, increases labor steps, and may not be appropriate for all enzymatic downstream assays.

In addition, the presence of commonly-used anion exchange materials can inhibit downstream analysis of nucleic acids. As such, current protocols require that the nucleic acid be separated from the anion exchange material before the purified nucleic acid can be analyzed. Unfortunately, complete separation of the eluate and the anion exchange material often cannot be achieved, thus reducing both the efficiency and the accuracy of subsequent analyses and amplifications. Moreover, the additional step of eluting and separating the eluate from the anion exchange material hampers the utility of anion exchange in fully automated nucleic acid purification and analysis procedures.

Thus, materials and methods are disclosed for isolating nucleic acids which do not require additional handling steps prior to a further use of the isolated nucleic acids. In particular, the isolated nucleic acids should be directly suitable for any amplification or analysis procedures.

SUMMARY OF INVENTION

The present disclosure relates to materials and methods for isolating and analyzing nucleic acids comprising the use of anion exchange chromatography in conjunction with an anionic compound. Using anionic compounds, in particular anionic compounds having at least two anionic groups, nucleic acids can be eluted from the anion exchange material without the use of unfavourably high pH values and/or to use high salt concentrations. Moreover, the presence of an anionic compound having at least two anionic groups has been found to permit amplification of nucleic acids in the presence of an anion exchange material.

In one aspect, a method of isolating nucleic acids is disclosed, said method comprising providing a nucleic acid complexed with an anion exchange material and eluting the bound nucleic acid by adding a solution comprising at least one anionic compound comprising at least two anionic groups. In one embodiment, the anionic compound comprising at least two anionic groups is a polyanionic compound, preferably a polyanionic organic compound. In another embodiment, the compound comprising at least two anionic groups is a non-polymeric compound, preferably a non-polymeric organic compound. In yet another embodiment, the elution step is performed without high salt conditions or severe changes in pH. In another embodiment, the nucleic acid complexed with the anion exchange material is provided by a method comprising the steps of contacting an anion-exchange composition with a sample comprising the nucleic acid, wherein the anion-exchange composition is capable of reversibly binding nucleic acid; and optionally washing the anion-exchange composition to remove unbound sample components. In the present methods, the compound comprising at least two anionic groups displaces the nucleic acids from the anion-exchange material. Using an anionic compound comprising at least two anionic groups for elution of the bound nucleic acid provides the advantages that these compounds do not have to be removed for performing subsequent analyses steps, including amplification steps, as they do not or only slightly interfere with such steps. Furthermore, only low concentrations of the compound comprising at least two anionic groups is necessary for effectively eluting the nucleic acid.

In another aspect, a method of analyzing a nucleic acid in the presence of an anion exchange material is provided, said method comprising providing a nucleic acid complexed with the anion exchange material to form a nucleic acid-anion exchange complex and analyzing the nucleic acid in the presence of at least one compound comprising at least two anionic groups. In one embodiment, the anionic compound comprising at least two anionic groups is a polyanionic compound. In another embodiment, the anionic compound comprising at least two anionic groups is a non-polymeric compound. In another embodiment, the nucleic acid complexed with the anion exchange material is provided by a method comprising the steps of contacting an anion-exchange composition with a sample comprising the nucleic acid, wherein the anion-exchange composition is capable of reversibly binding nucleic acid; optionally washing the anion-exchange composition to remove unbound sample components; and optionally separating the nucleic acid-anion exchange complex from other material.

Yet another aspect is an elution composition comprising an anionic compound comprising at least two anionic groups and further comprising at least one buffer. One advantage of the provided methods and compositions is that they provide flexibility with respect to the used elution conditions and elution buffers and furthermore, may make the elution more effective. Therefore, the present elution composition may comprise any buffer or composition commonly used for elution. By way of example and not limitation, the elution buffer may be formed by combining the anionic compound may be combined with water, low salt buffers, or biological buffers such as CHAPS, MES, HEPES, MOPS, TRIS, TRICINE and PIPES. In one embodiment, the compound comprising at least two anionic groups is a polyanionic compound. In another embodiment, the compound comprising at least two anionic groups is a non-polymeric compound.

Yet another aspect relates to an eluate obtained by the elution methods disclosed herein.

Yet another aspect is an amplification composition comprising a polymerase and an anionic compound comprising at least two anionic groups. In another embodiment, the amplification composition optionally comprises: an enzyme having reverse transcriptase activity; and enzyme having helicase activity; a nick-inducing agent; $Mg^{2+}$ or a source thereof, such as $MgCl_2$; a ribonucleotide triphosphate (NTP); a deoxyribonucleotide triphosphate (dNTP); $K^+$ or a source thereof, such as KCl; $NH_4^+$ or a source thereof, such as $(NH_4)_2SO_4$; a buffer, such as Tris; and/or a reducing agent, such as 2-mercapthoethanol or dithiothreitol (DTT). In one embodiment, the compound comprising at least two anionic groups is a polyanionic compound. In another embodiment, the compound comprising at least two anionic groups is a non-polymeric compound.

Yet another aspect is a kit for isolating nucleic acids from a sample, the kit comprising an anion exchange material and an anionic compound comprising at least two anionic groups.

In another aspect, a kit for amplifying a nucleic acid is provided comprising a polymerase, an anion exchange material, and an anionic compound comprising at least two anionic groups. In another embodiment, the amplification composition optionally comprises: $Mg^{2+}$ or a source thereof, such as $MgCl_2$; a ribonucleotide triphosphate (NTP); a deoxyribonucleotide triphosphate (dNTP); $K^+$ or a source thereof, such as KCl; $NH_4^+$ or a source thereof, such as $(NH_4)_2SO_4$; a buffer, such as Tris; and/or a reducing agent, such as 2-mercapthoethanol or dithiothreitol (DTT). In one embodiment, the compound comprising at least two anionic groups is a polyanionic compound. In another embodiment, the compound comprising at least two anionic groups is a non-polymeric compound.

In a further aspect, the use of an anionic compound comprising at least two anionic groups for displacing a nucleic acid reversibly bound to an anion-exchange material from said anion-exchange material is provided. In one embodiment, the compound comprising at least two anionic groups is a polyanionic compound. In another embodiment, the compound comprising at least two anionic groups is a non-polymeric compound.

| Lane | Sample |
|---|---|
| 1 | 1 kb+ Ladder |
| 2 | 1 µg 300 bp control |
| 3 | 1 µg, 2 µg, 3 µg 500 bp control |
| 4 | Flow-through, binding, wash 1, wash 2 |
| 5 | Eluate 1, pH 7.0, 1 µg 500 bp |
| 6 | Eluate 1, pH 7.0, 2 µg 500 bp |
| 7 | Eluate 1, pH 7.0, 3 µg 500 bp |
| 8 | Eluate 2, pH 8.5, 50 mM MES, 50 mM NaCl |
| 9 | Flow-through, binding, wash 1, wash 2 |
| 10 | Eluate 1, pH 7.0, 1 µg 500 bp |
| 11 | Eluate 1, pH 7.0, 2 µg 500 bp |
| 12 | Eluate 1, pH 7.0, 3 µg 500 bp |
| 13 | Eluate 2, pH 8.5, 50 mM MES, 50 mM NaCl |
| 14 | 1 kb+ Ladder |

Figure 2:
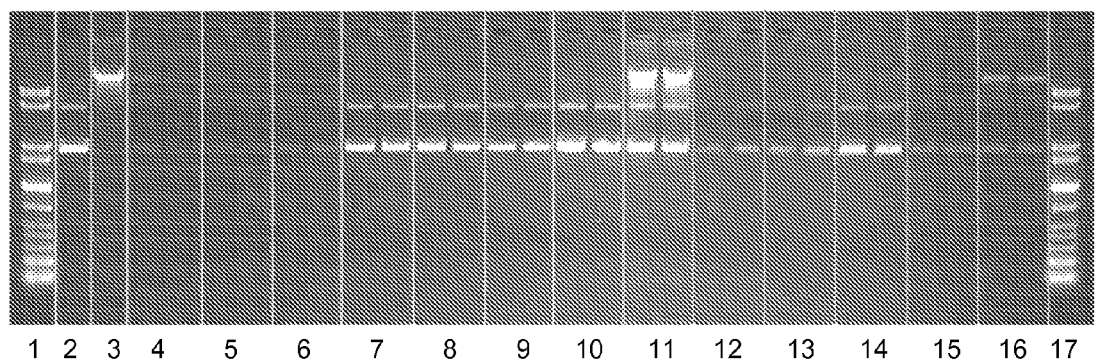
Figure 2:
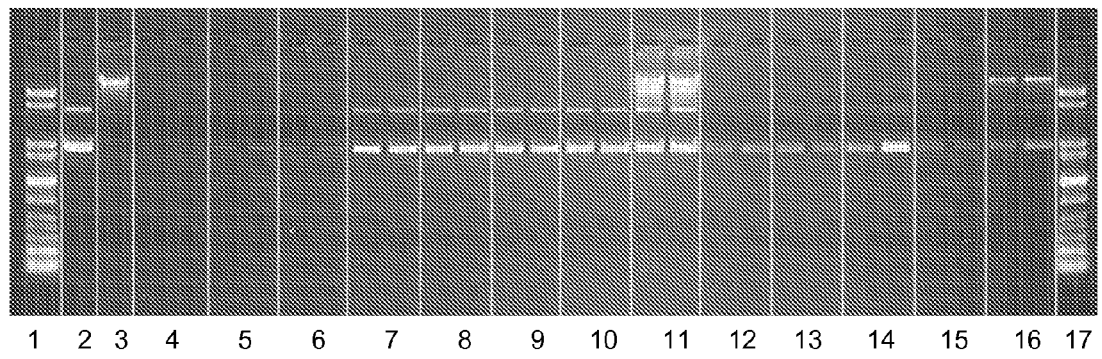

FIG. 2 shows a Gel-electrophoretic analysis of the bound and eluted nucleic acids. Plasmid DNA was bound onto polyethylenimine magnetic beads and eluted using dextransulfate, polyacrylic acid, oxalic acid, mellitic acid or genomic DNA. A: Binding and elution at pH 8.0. B: Binding and elution at pH 8.5. The gels are loaded as follows:

| Lane | Sample |
|---|---|
| | A |
| 1 | 1 kb+ ladder |
| 2 | 2 µg pUC21 control |
| 3 | 2 µg gDNA control |
| 4 | Flow-through, binding, pH 8.0 |
| 5 | Wash 1, MilliQ1 |
| 6 | Wash 2, MilliQ1 |
| 7 | Eluate 1, 500 ng dextran sulfate |
| 8 | Eluate 1, 500 ng polyacrylic acid |

| Lane | Sample |
|---|---|
| 9 | Eluate 1, 500 ng oxalic acid |
| 10 | Eluate 1, 500 ng mellitic acid |
| 11 | Eluate 1, 2 µg gDNA |
| 12 | Eluate 2, pH 8.5, 50 mM MES, 50 mM NaCl, (dextran sulfate) |
| 13 | Eluate 2, pH 8.5, 50 mM MES, 50 mM NaCl, (polyacrylic acid) |
| 14 | Eluate 2, pH 8.5, 50 mM MES, 50 mM NaCl, (oxalic acid) |
| 15 | Eluate 2, pH 8.5, 50 mM MES, 50 mM NaCl, (mellitic acid) |
| 16 | Eluate 2, pH 8.5, 50 mM MES, 50 mM NaCl, (2 µg gDNA) |
| 17 | 1 kb+ ladder |
| B | |
| 1 | 1 kb+ ladder |
| 2 | 2 µg pUC21 control |
| 3 | 2 µg gDNA control |
| 4 | Flow-through, binding, pH 8.5 |
| 5 | Wash 1, MilliQ1 |
| 6 | Wash 2, MilliQ1 |
| 7 | Eluate 1, 500 ng dextran sulfate |
| 8 | Eluate 1, 500 ng polyacrylic acid |
| 9 | Eluate 1, 500 ng oxalic acid |
| 10 | Eluate 1, 500 ng mellitic acid |
| 11 | Eluate 1, 2 µg gDNA |
| 12 | Eluate 2, pH 8.5, 50 mM MES, 50 mM NaCl, (dextran sulfate) |
| 13 | Eluate 2, pH 8.5, 50 mM MES, 50 mM NaCl, (polyacrylic acid) |
| 14 | Eluate 2, pH 8.5, 50 mM MES, 50 mM NaCl, (oxalic acid) |
| 15 | Eluate 2, pH 8.5, 50 mM MES, 50 mM NaCl, (mellitic acid) |
| 16 | Eluate 2, pH 8.5, 50 mM MES, 50 mM NaCl, (2 µg gDNA) |
| 17 | 1 kb+ ladder |

Figure 3:
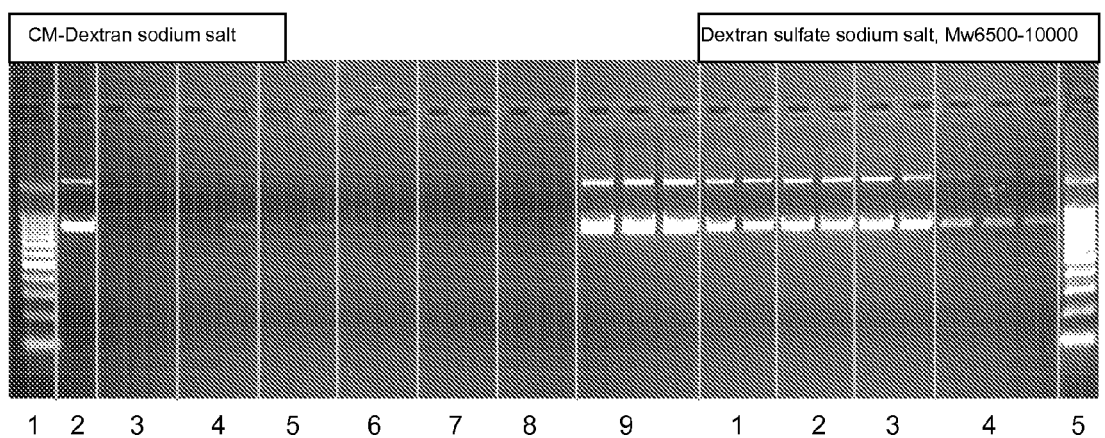
Figure 3:
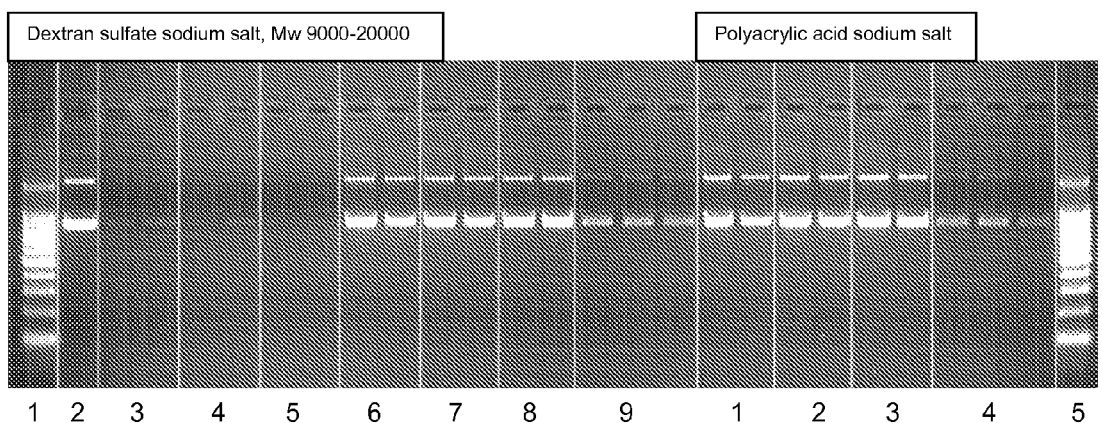

FIG. 3 shows a Gel-electrophoretic analysis of the bound and eluted nucleic acids. Plasmid DNA was bound onto spermine magnetic beads and eluted using carboxymethyl dextran, dextransulfate, polyacrylic acid, poly(4-styrenesulfonic maleic acid), acetic acid, oxalic acid, citric acid, pyromellitic acid, or mellitic acid. The gels are loaded as follows:

| Lane | Sample |
|---|---|
| CM-Dextran sodium salt | |
| 1 | 200 bp ladder |
| 2 | 2 µg pUC21 control |
| 3 | Flow-through binding |
| 4 | Wash 1, MilliQ |
| 5 | Wash 2, MilliQ |
| 6 | Eluate 1, 2000 ng buffer 5 |
| 7 | Eluate 1, 5000 ng buffer 5 |
| 8 | Eluate 1, 10000 ng buffer 5 |
| 9 | Eluate 2 (buffer 5), 50 mM NaCl, 50 mM Tris pH 8.5 |
| Dextran sulfate sodium salt, Mw 6500-10000 | |
| 1 | Eluate 1, 2000 ng buffer 2 |
| 2 | Eluate 1, 5000 ng buffer 2 |
| 3 | Eluate 1, 10000 ng buffer 2 |
| 4 | Eluate 2, (buffer 2) 50 mM NaCl, 50 mM TRIS pH 8.5 |
| 5 | 200 bp ladder |
| Dextran sulfate sodium salt, Mw 9000-20000 | |
| 1 | 200 bp ladder |
| 2 | 2 µg pUC21 control |
| 3 | Flow-through binding |
| 4 | Wash 1, MilliQ |
| 5 | Wash 2, MilliQ |
| 6 | Eluate 1, 2000 ng buffer 3 |
| 7 | Eluate 1, 5000 ng buffer 3 |
| 8 | Eluate 1, 10000 ng buffer 3 |
| 9 | Eluate 2 (buffer 3) 50 mM NaCl, 50 mM TRIS pH 8.5 |
| Polyacrylic acid sodium salt | |
| 1 | Eluate 1, 2000 ng buffer 4 |
| 2 | Eluate 1, 5000 ng buffer 4 |
| 3 | Eluate 1, 10000 ng buffer 4 |
| 4 | Eluate 2, (buffer 4) 50 mM NaCl, 50 mM TRIS pH 8.5 |
| 5 | 200 bp ladder |

| Lane | Sample |
|---|---|
| Poly (4-styrenesulfonate maleic acid) | |
| 1 | 1 kb+ ladder |
| 2 | 2 µg pUC21 control |
| 3 | Flow-through binding |
| 4 | Wash 1, MilliQ |
| 5 | Wash 2, MilliQ |
| 6 | Eluate 1, 2000 ng buffer 5 |
| 7 | Eluate 1, 5000 ng buffer 5 |
| 8 | Eluate 1, 10000 ng buffer 5 |
| 9 | Eluate 2 (buffer 5) 50 mM NaCl, 50 mM TRIS pH 8.5 |
| Acetic acid | |
| 1 | Eluate 1, 2000 ng buffer 6 |
| 2 | Eluate 1, 5000 ng buffer 6 |
| 3 | Eluate 1, 10000 ng buffer 6 |
| 4 | Eluate 2, (buffer 6) 50 mM NaCl, 50 mM TRIS pH 8.5 |
| 5 | 1 kb+ ladder |
| Oxalic acid | |
| 1 | 1 kb+ ladder |
| 2 | 2 µg pUC21 control |
| 3 | Flow-through binding |
| 4 | Wash 1, MilliQ |
| 5 | Wash 2, MilliQ |
| 6 | Eluate 1, 2000 ng buffer 7 |
| 7 | Eluate 1, 5000 ng buffer 7 |
| 8 | Eluate 1, 10000 ng buffer 7 |
| 9 | Eluate 2 (buffer 7) 50 mM NaCl, 50 mM TRIS pH 8.5 |
| Citric acid | |
| 1 | Eluate 1, 2000 ng buffer 8 |
| 2 | Eluate 1, 5000 ng buffer 8 |
| 3 | Eluate 1, 10000 ng buffer 8 |
| 4 | Eluate 2, (buffer 8) 50 mM NaCl, 50 mM TRIS pH 8.5 |
| 5 | 1 kb+ ladder |
| Pyromellitic acid | |
| 1 | 1 kb+ ladder |
| 2 | 2 µg pUC21 control |
| 3 | Flow-through binding |
| 4 | Wash 1, MilliQ |
| 5 | Wash 2, MilliQ |
| 6 | Eluate 1, 2000 ng buffer 9 |
| 7 | Eluate 1, 5000 ng buffer 9 |
| 8 | Eluate 1, 10000 ng buffer 9 |
| 9 | Eluate 2 (buffer 9) 50 mM NaCl, 50 mM TRIS pH 8.5 |
| Mellitic acid | |
| 1 | 1 kb+ ladder |
| 2 | Flow-through binding |
| 3 | Wash 1, MilliQ |
| 4 | Wash 2, MilliQ |
| 5 | Eluate 1, 2000 ng buffer 11 |
| 6 | Eluate 1, 5000 ng buffer 11 |
| 7 | Eluate 1, 10000 ng buffer 11 |
| 8 | Eluate 2 (buffer 11) 50 mM NaCl, 50 mM TRIS pH 8.5 |
| 9 | 2 µg pUC21 control |
| 10 | 1 kb+ ladder |

Figure 4:
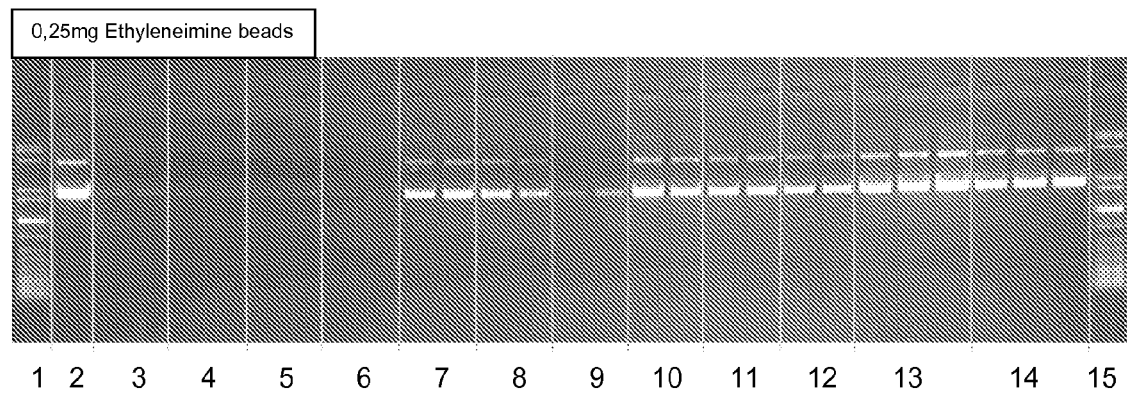

FIG. 4 shows a Gel-electrophoretic analysis of the bound and eluted nucleic acids. Plasmid DNA was bound onto spermine or polyethylenimine magnetic beads and eluted using "base-free" DNA. The gels are loaded as follows:

| 0.25 mg Ethyleneimine beads | |
|---|---|
| Lane | Sample |
| 1 | 1 kb+ ladder |
| 2 | 5 µg pUC21 control |
| 3 | Flow-through binding pH 8.0 |
| 4 | Flow-through binding pH 8.5 |
| 5 | Wash 1, MilliQ, pH 8.0 |

0.25 mg Ethyleneimine beads

| Lane | Sample |
|---|---|
| 6 | Wash 1, MilliQ, pH 8 5 |
| 7 | Eluate 1, pH 8.0, 2 µg 'base-free' |
| 8 | Eluate 1, pH 8.0, 5 µg 'base-free' |
| 9 | Eluate 1, pH 8.0, 10 µg 'base-free' |
| 10 | Eluate 1, pH 8.5, 2 µg 'base-free' |
| 11 | Eluate 1, pH 8.5, 5 µg 'base-free' |
| 12 | Eluate 1, pH 8.5, 10 µg 'base-free' |
| 13 | Binding pH 8.0, Elutate 2, pH 8.5, 50 mM MES/NaCl, 2/5/10 µg ('base-free') |
| 14 | Binding pH 8.5, Elutate 2, pH 8.5, 50 mM MES/NaCl, 2/5/10 µg ('base-free') |
| 15 | 1 kb+ ladder |

Figure 5:
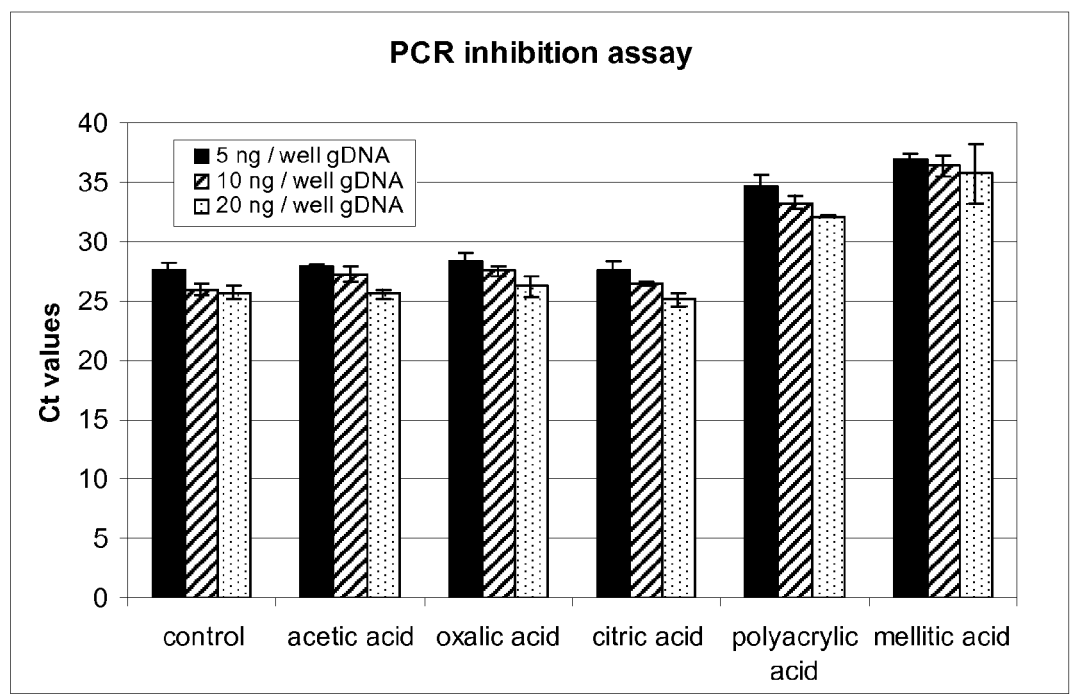

FIG. 5 shows a PCR inhibition assay. The influence of different carboxylic acids on the ct-value of a β-actin PCR was tested.

Figure 6:
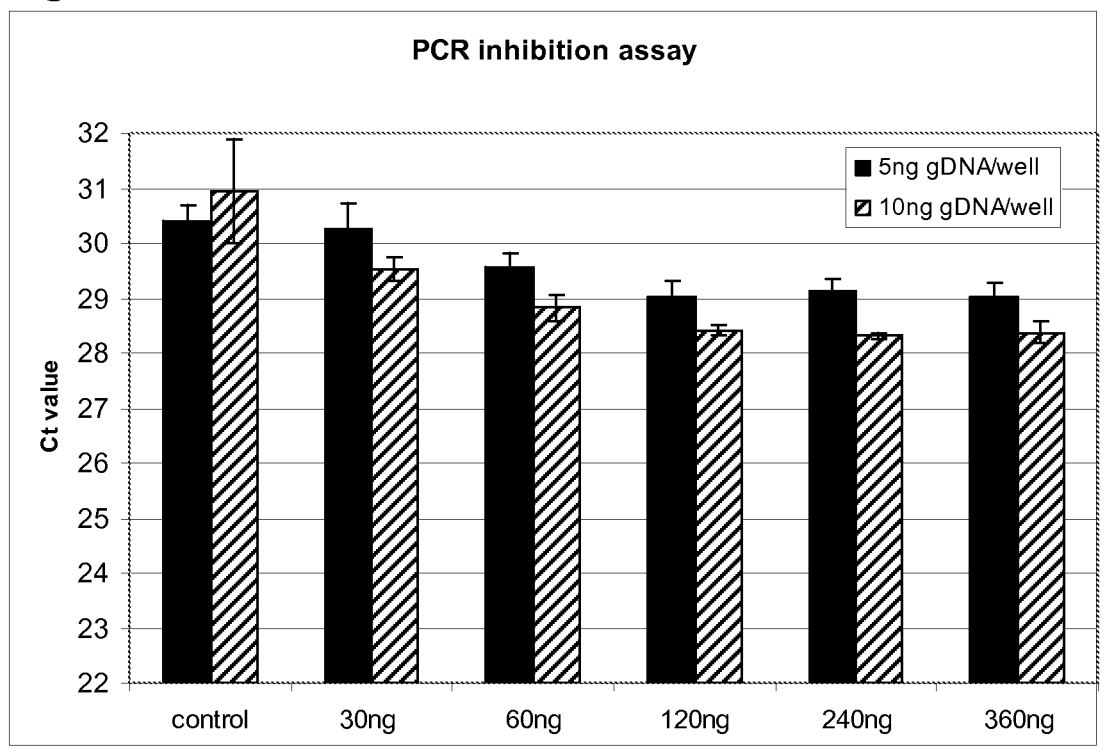

FIG. 6 shows a PCR inhibition assay. The influence of different citric acid concentrations on the ct-value of a β-actin PCR was tested.

Figure 7:
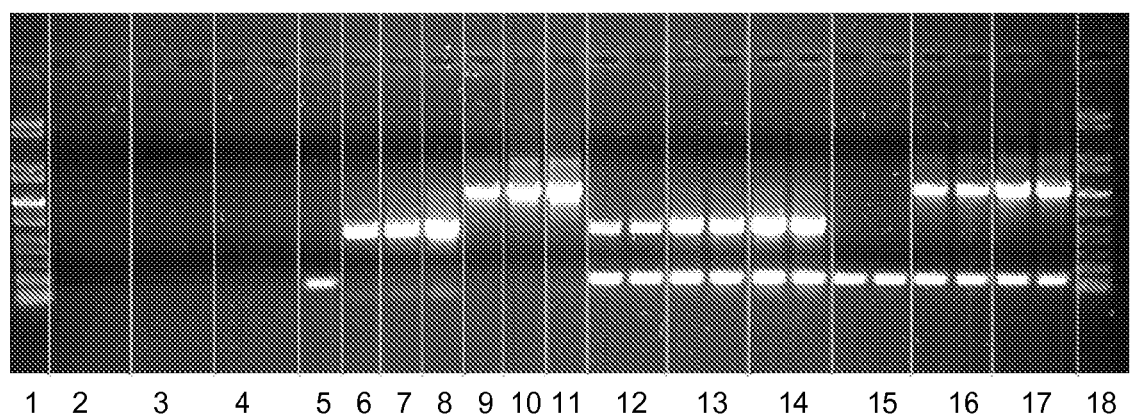

FIG. 7 shows a Gel-electrophoretic analysis of the bound and eluted nucleic acids. A 100 bp DNA fragment was bound onto spermine magnetic beads and eluted using a 500 bp or 1000 bp DNA fragment. The gels are loaded as follows:

| Lane | Sample |
|---|---|
| 1 | 1 kb+ ladder |
| 2 | Flow-through, binding, 1 µg 100 bp |
| 3 | Wash 1, 100 µl MilliQ |
| 4 | Wash 2, 100 µl MilliQ |
| 5 | 1 µg 100 bp control |
| 6 | Control 500 bp, 1 µg |
| 7 | Control 500 bp, 2 µg |
| 8 | Control 500 bp, 3 µg |
| 9 | Control 1000 bp, 1 µg |
| 10 | Control 1000 bp, 2 µg |
| 11 | Control 1000 bp, 3 µg |
| 12 | 500 bp elution, 25 mM MES, pH 7.0, 1 µg |
| 13 | 500 bp elution, 25 mM MES, pH 7.0, 2 µg |
| 14 | 500 bp elution, 25 mM MES, pH 7.0, 3 µg |
| 15 | 1000 bp elution, 25 mM MES, pH 7.0, 1 µg |
| 16 | 1000 bp elution, 25 mM MES, pH 7.0, 2 µg |
| 17 | 1000 bp elution, 25 mM MES, pH 7.0, 3 µg |
| 18 | 1 kb+ |

Figure 8:
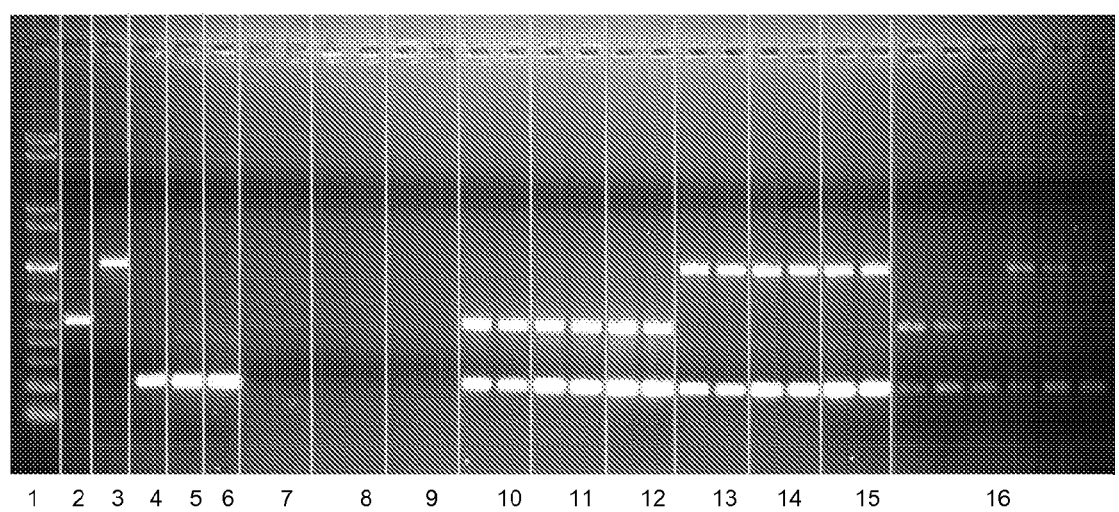

FIG. 8 shows a Gel-electrophoretic analysis of the bound and eluted nucleic acids. A 500 bp or 1000 bp DNA fragment was bound onto spermine magnetic beads and eluted using a 200 bp DNA fragment. The gels are loaded as follows:

| Lane | Sample |
|---|---|
| 1 | 1 kb+ ladder |
| 2 | 1 µg 500 bp control |
| 3 | 1 µg 1000 bp control |
| 4 | Control 200 bp, 1 µg |
| 5 | Control 200 bp, 2 µg |
| 6 | Control 200 bp, 3 µg |
| 7 | Flow-through, binding, pH 7.0 |
| 8 | Wash 1, MilliQ |
| 9 | Wash 2, MilliQ |
| 10 | binding 500 bp, 200 bp elution, 1 µg |
| 11 | binding 500 bp, 200 bp elution, 2 µg |
| 12 | binding 500 bp, 200 bp elution, 3 µg |
| 13 | binding 1000 bp, 200 bp elution, 1 µg |
| 14 | binding 1000 bp, 200 bp elution, 2 µg |
| 15 | binding 1000 bp, 200 bp elution, 3 µg |
| 16 | $2^{nd}$ elution (50 mM NaCl, 50 mM TRIS, pH 8.5) |

Figure 9:
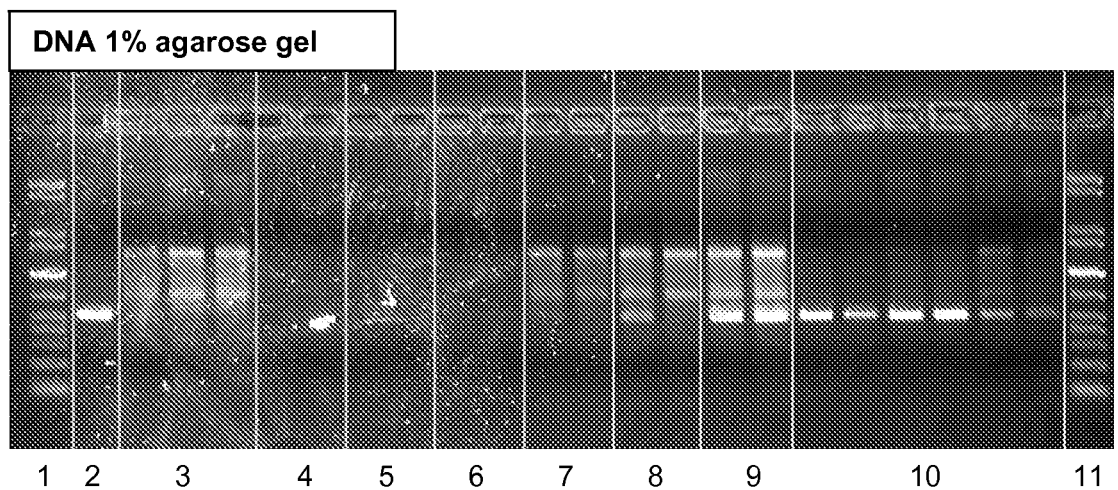
Figure 9:
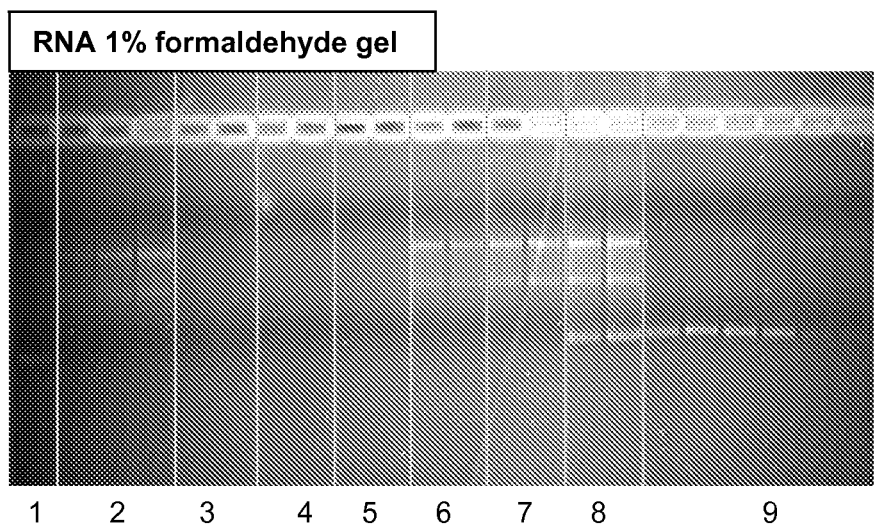

FIG. 9 shows a Gel-electrophoretic analysis of the bound and eluted nucleic acids. A 500 bp DNA fragment was bound onto spermine magnetic beads and eluted using RNA. The gels are loaded as follows:

| Lane | Sample |
|---|---|
| | DNA, 1% agarose gel |
| 1 | 1 kb+ ladder |
| 2 | 1 µg 500 bp control |
| 3 | 1 µg, 2 µg, 3 µg RNA control |
| 4 | Flow-through binding |
| 5 | Wash 1 |
| 6 | Wash 2 |
| 7 | Eluate 1, pH 7.0, 1 µg RNA |
| 8 | Eluate 1, pH 7.0, 2 µg RNA |
| 9 | Eluate 1, pH 7.0, 3 µg RNA |
| 10 | Eluate 2, pH 8.5, 50 mM NaCl, 50 mM TRIS |
| 11 | 1 kb+ ladder |
| | RNA, 1% formaldehyde gel |
| 1 | 1 µg 500 bp control |
| 2 | 1 µg, 2 µg, 3 µg RNA control |
| 3 | Flow-through binding |
| 4 | Wash 1 |
| 5 | Wash 2 |
| 6 | Eluate 1, pH 7.0, 1 µg RNA |
| 7 | Eluate 1, pH 7.0, 2 µg RNA |
| 8 | Eluate 1, pH 7.0, 3 µg RNA |
| 9 | Eluate 2, pH 8.5, 50 mM NaCl, 50 mM TRIS |

Figure 10:
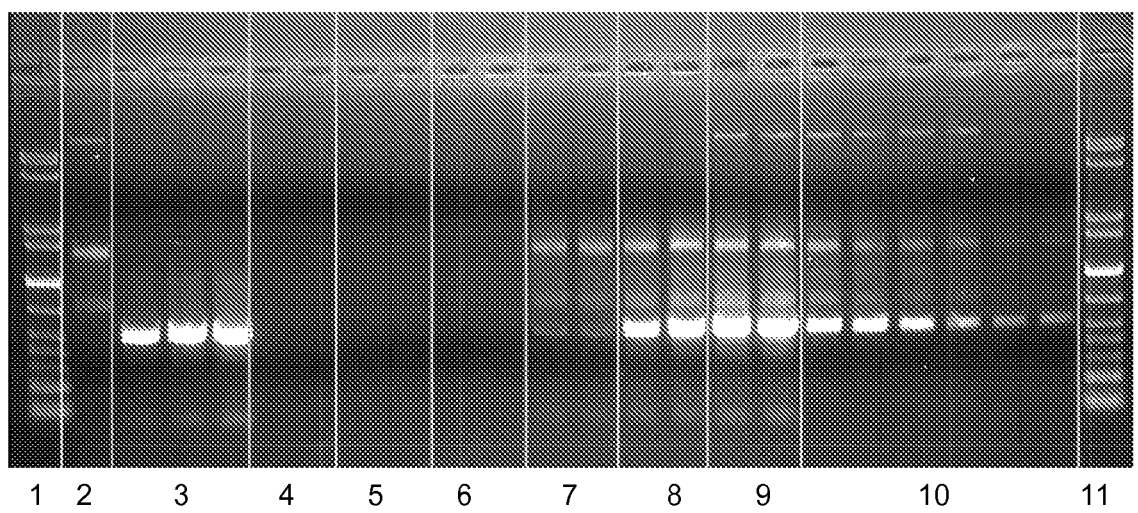

FIG. 10 shows a Gel-electrophoretic analysis of the bound and eluted nucleic acids. RNA was bound onto spermine magnetic beads and eluted using a 500 bp DNA fragment. The gels are loaded as follows:

| Lane | Sample |
|---|---|
| 1 | 1 kb+ ladder |
| 2 | 2 µg RNA control |
| 3 | 1 µg, 2 µg, 3 µg 500 bp control |
| 4 | Flow-through binding |
| 5 | Wash 1 |
| 6 | Wash 2 |
| 7 | Eluate 1, 1 µg 500 bp |
| 8 | Eluate 1, 2 µg 500 bp |
| 9 | Eluate 1, 3 µg 500 bp |
| 10 | Eluate 2, 50 mM NaCl, 50 mM TRIS, pH 8.5 |
| 11 | 1 kb+ ladder |

Figure 11:
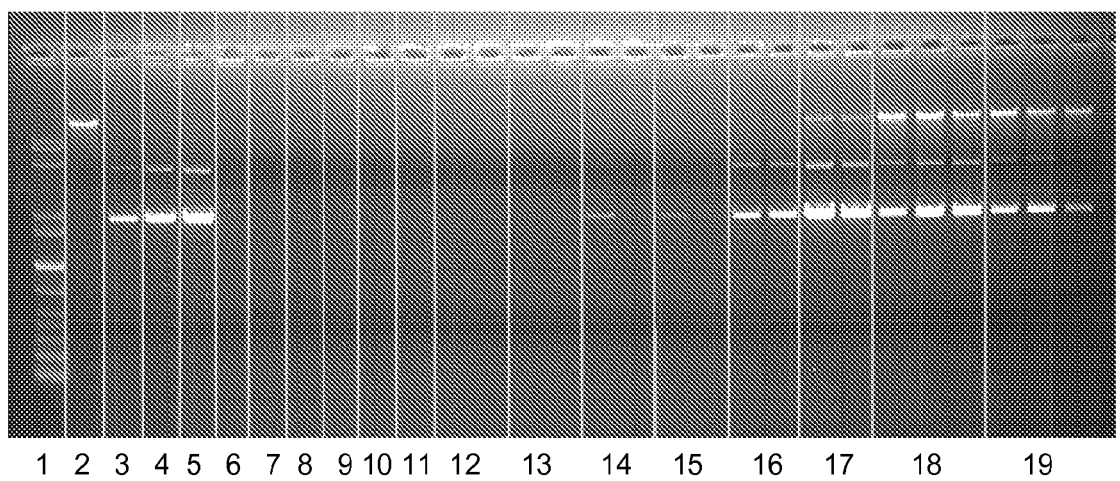

FIG. 11 shows a Gel-electrophoretic analysis of the bound and eluted nucleic acids. Genomic DNA was bound onto spermine magnetic beads and eluted using plasmid DNA. The gels are loaded as follows:

| Lane | Sample |
|---|---|
| 1 | 1 kb+ ladder |
| 2 | 1 µg gDNA control |
| 3 | 1 µg pUC21 control |
| 4 | 2 µg pUC21 control |
| 5 | 3 µg pUC21 control |
| 6 | 0.25 mg NK_04, binding |
| 7 | 0.25 mg NK_04, wash 1 |

-continued

| Lane | Sample |
|---|---|
| 8 | 0.25 mg NK_04, wash 2 |
| 9 | 0.125 mg NK_04, binding |
| 10 | 0.125 mg NK_04, wash 1 |
| 11 | 0.125 mg NK_04, wash 2 |
| 12 | Elution 1, 0.25 mg NK_04, 12.5 mg MES, pH 7.0, 1 µg |
| 13 | Elution 1, 0.25 mg NK_04, 12.5 mg MES, pH 7.0, 2 µg |
| 14 | Elution 1, 0.25 mg NK_04, 12.5 mg MES, pH 7.0, 3 µg |
| 15 | Elution 1, 0.125 mg NK_04, 12.5 mg MES, pH 7.0, 1 µg |
| 16 | Elution 1, 0.125 mg NK_04, 12.5 mg MES, pH 7.0, 2 µg |
| 17 | Elution 1, 0.125 mg NK_04, 12.5 mg MES, pH 7.0, 3 µg |
| 18 | Elution 2, 0.25 mg NK_04, 50 mM TRIS, 50 mM NaCl pH 8.5 |
| 19 | Elution 2, 0.125 mg NK_04, 50 mM TRIS, 50 mM NaCl pH 8.5 |

Figure 12:
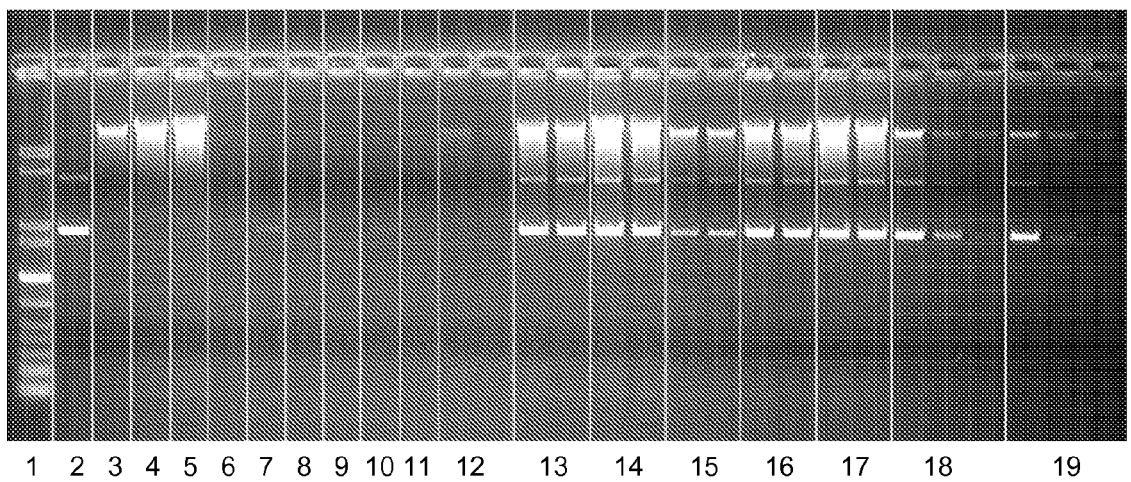

FIG. 12 shows a Gel-electrophoretic analysis of the bound and eluted nucleic acids. Plasmid DNA was bound onto spermine magnetic beads and eluted using genomic DNA. The gels are loaded as follows:

| Lane | Sample |
|---|---|
| 1 | 1 kb+ ladder |
| 2 | 1 µg pUC21 control |
| 3 | 1 µg gDNA control |
| 4 | 2 µg gDNA control |
| 5 | 3 µg gDNA control |
| 6 | 0.25 mg NK_04, binding |
| 7 | 0.25 mg NK_04, wash 1 |
| 8 | 0.25 mg NK_04, wash 2 |
| 9 | 0.125 mg NK_04, binding |
| 10 | 0.125 mg NK_04, wash 1 |
| 11 | 0.125 mg NK_04, wash 2 |
| 12 | Elution 1, 0.25 mg NK_04, 12.5 mg MES, pH 7.0, 1 µg |
| 13 | Elution 1, 0.25 mg NK_04, 12.5 mg MES, pH 7.0, 2 µg |
| 14 | Elution 1, 0.25 mg NK_04, 12.5 mg MES, pH 7.0, 3 µg |
| 15 | Elution 1, 0.125 mg NK_04, 12.5 mg MES, pH 7.0, 1 µg |
| 16 | Elution 1, 0.125 mg NK_04, 12.5 mg MES, pH 7.0, 2 µg |
| 17 | Elution 1, 0.125 mg NK_04, 12.5 mg MES, pH 7.0, 3 µg |
| 18 | Elution 2, 0.25 mg NK_04, 50 mM TRIS, 50 mM NaCl pH 8.5 |
| 19 | Elution 2, 0.125 mg NK_04, 50 mM TRIS, 50 mM NaCl pH 8.5 |

Figure 13:
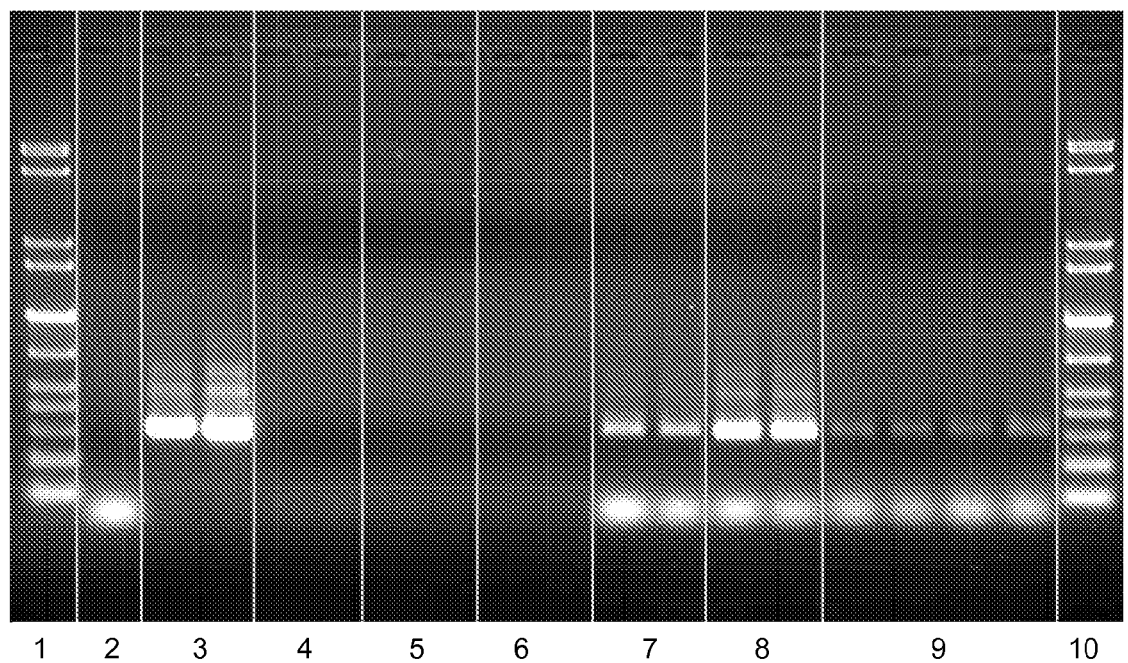

FIG. 13 shows a Gel-electrophoretic analysis of the bound and eluted nucleic acids. siRNA was bound onto polyethylenimine magnetic beads and eluted using a 300 bp DNA fragment. The gels are loaded as follows:

| Lane | Sample |
|---|---|
| 1 | 1 kb+ ladder |
| 2 | 1.5 µg siRNA control |
| 3 | 1 µg, 2 µg, 300 bp control |
| 4 | Flow-through binding |
| 5 | Wash 1 |
| 6 | Wash 2 |
| 7 | Eluate 1, 2 µg 300 bp |
| 8 | Eluate 1, 3 µg 300 bp |
| 9 | Eluate 2, pH 8.5, 50 mM TRIS, 100 mM NaCl |
| 10 | 1 kb+ ladder |

FIG. 14 shows that amplification curves in PCR are normal and PAA does not promote artifact formation in PCR. FIGS. 14A-14B show the results of an experiment where threshold cycles (Ct) were detected using a TaqMan®-MGB probe. FIG. 14C provides the results of an experiment where melting curves were recorded to confirm product identity in PCR. See Example 15.

Figure 15:
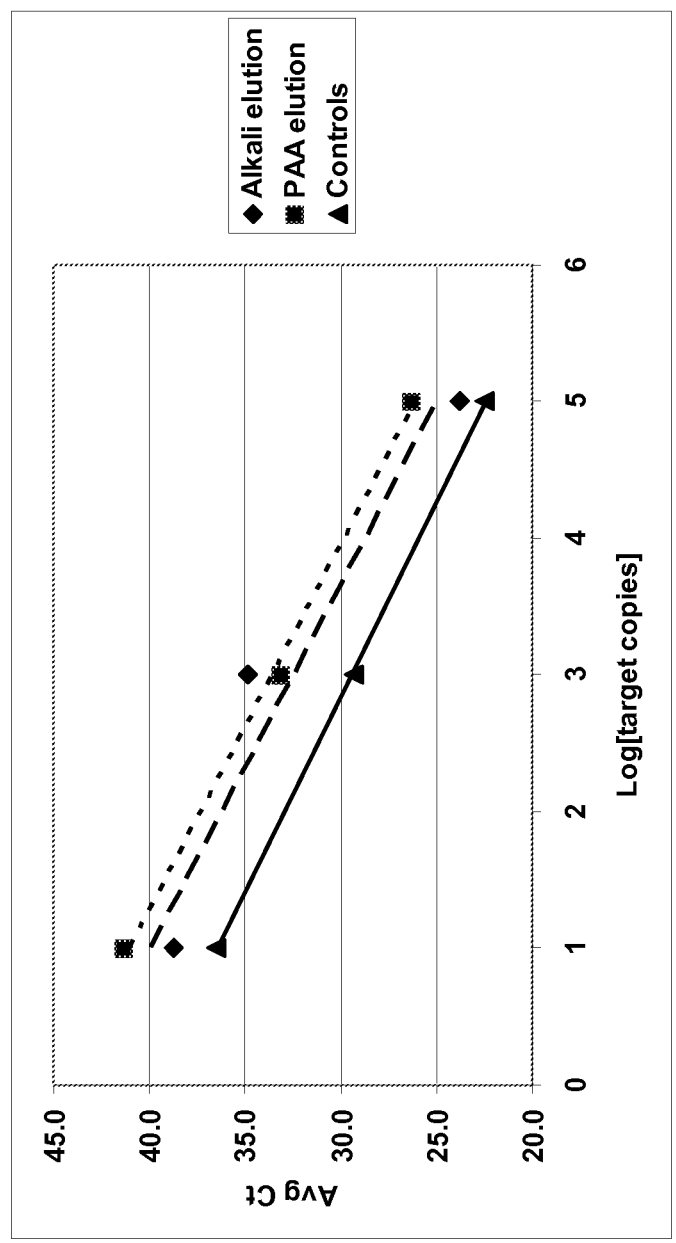

FIG. 15 provides the results of real-time PCR of various concentrations of *Neisseria Gonorrhoeae* (NG) DNA comparing the different elutions: AXpH™ beads, alkali or PAA.

Figure 16A:
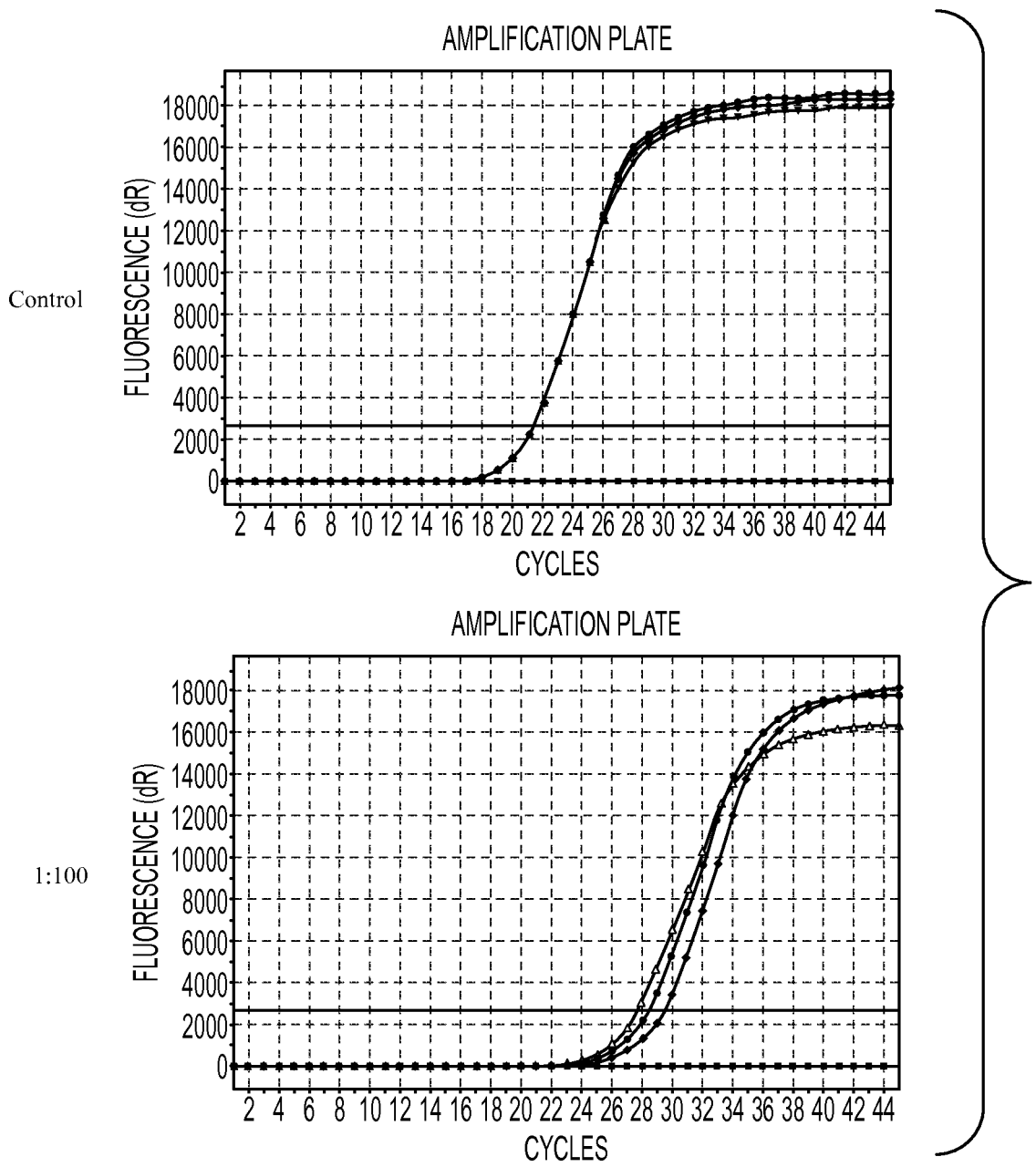
Figure 16B:
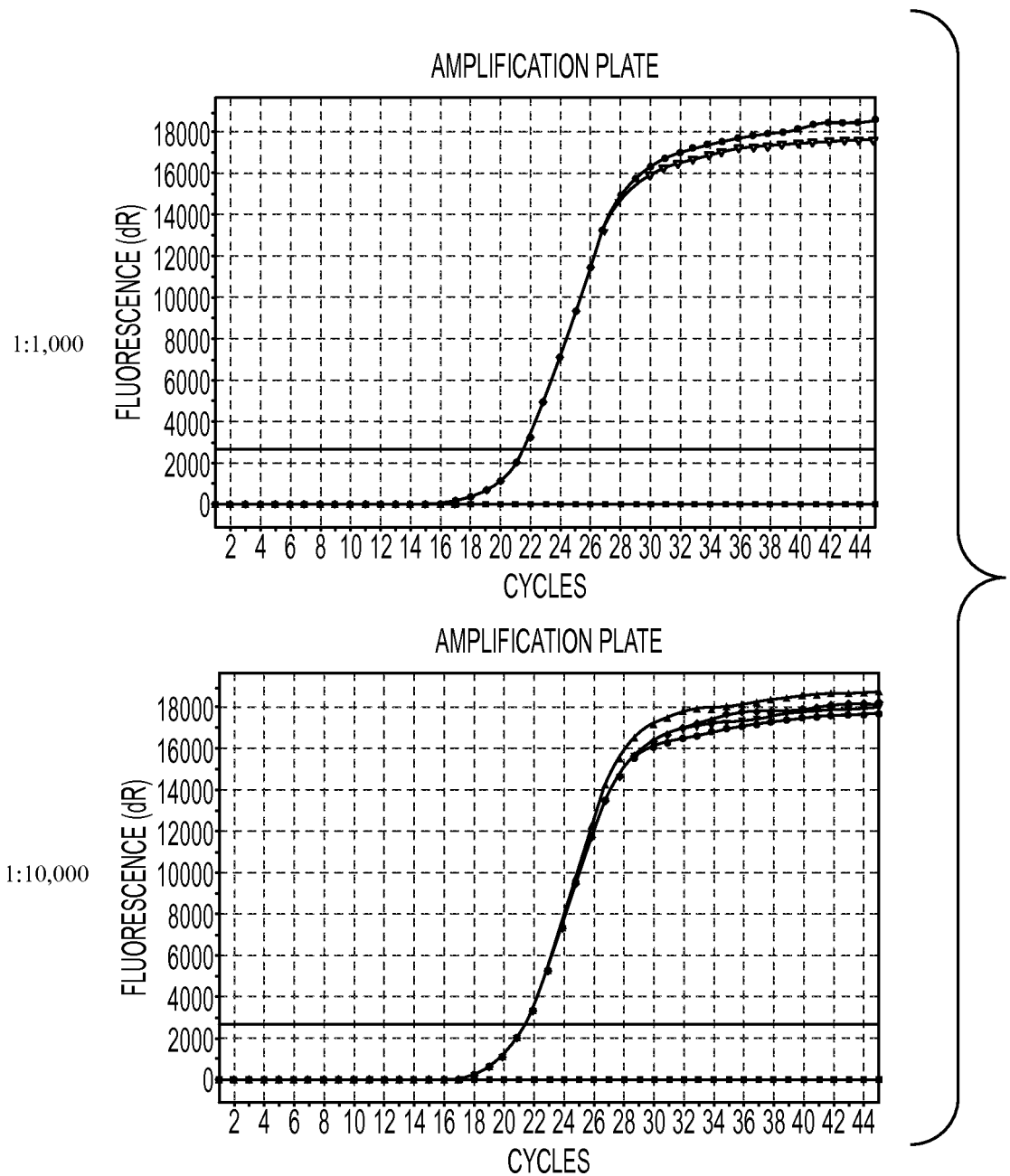

FIG. 16 demonstrates the inhibitory effect of anion exchange materials on PCR. Real time PCR amplifications were performed in triplicate in the presence of no beads (FIG. 16A) or 1:10 (FIG. 16A), 1:100 (FIG. 16B), and 1:1000 (FIG. 16B) dilutions of AXpH™ beads. Fluorescent signals were generated using reporter probes labeled with 6-FAMT™ ("FAM") dye, which is an isomer of carboxyfluorescein as described in Brandis, Dye structure affects Taq DNA polymerase terminator selectivity, Nucl. Acids Res. 1999 27(8): 1912-1918. Inhibition is shown by a shift of the linear phase of the amplification curve to the right.

Figure 17:
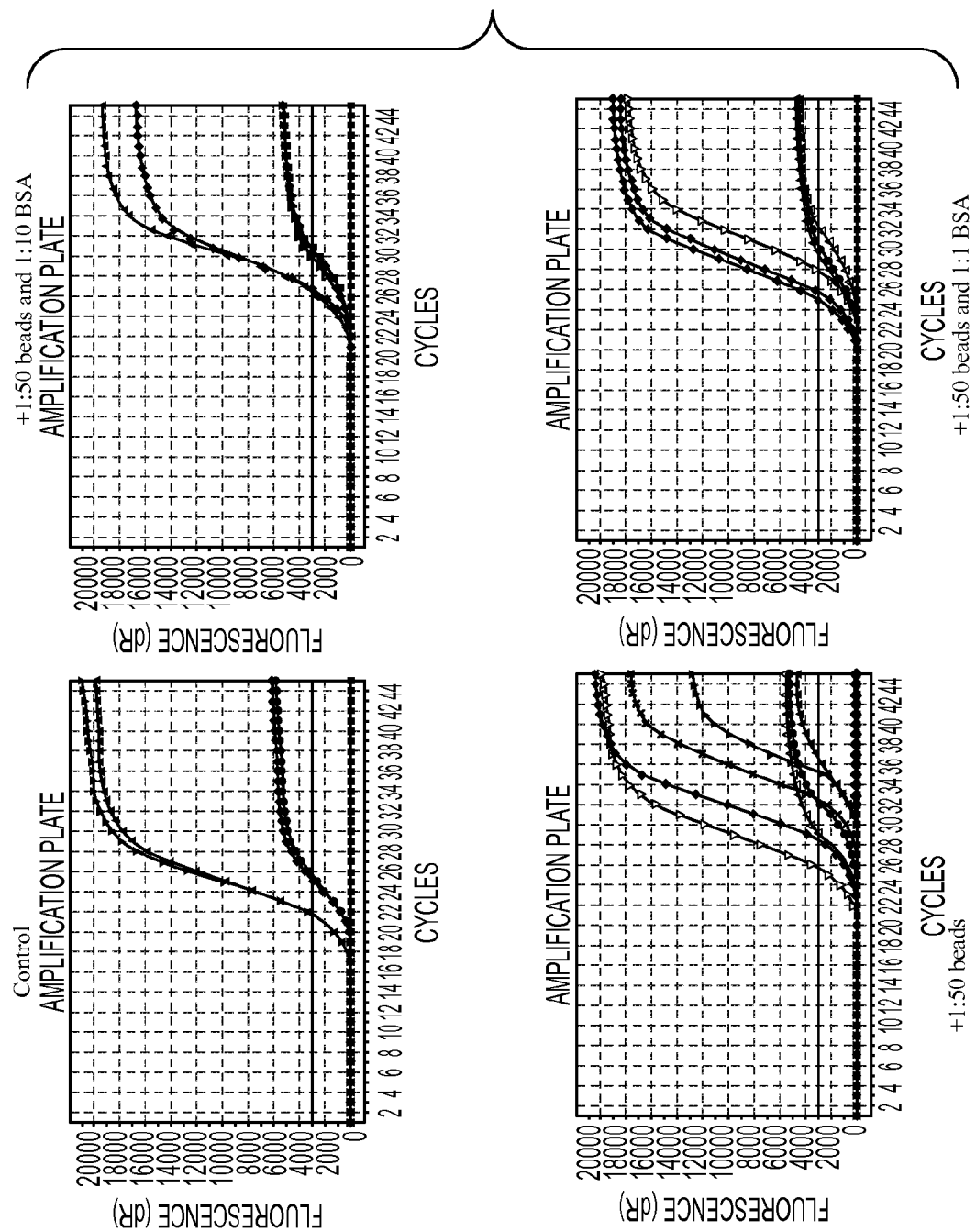

FIG. 17 demonstrates that bovine serum albumin does not rescue PCR in the presence of anion exchange materials. Real time PCR amplifications were performed in triplicate in the presence of 1:50 dilutions of AXpH™ beads and 0, 1:1, and 1:10 dilutions of 1 mg/ml stock bovine serum albumin to a final concentration of 0.1 mg/ml and 0.01 mg/ml of BSA. Fluorescent signals were generated using reporter probes labeled with either FAM (top curve) or 5'-Tetrachloro-Fluorescein ("TET") dye (lower curve).

Figure 18:
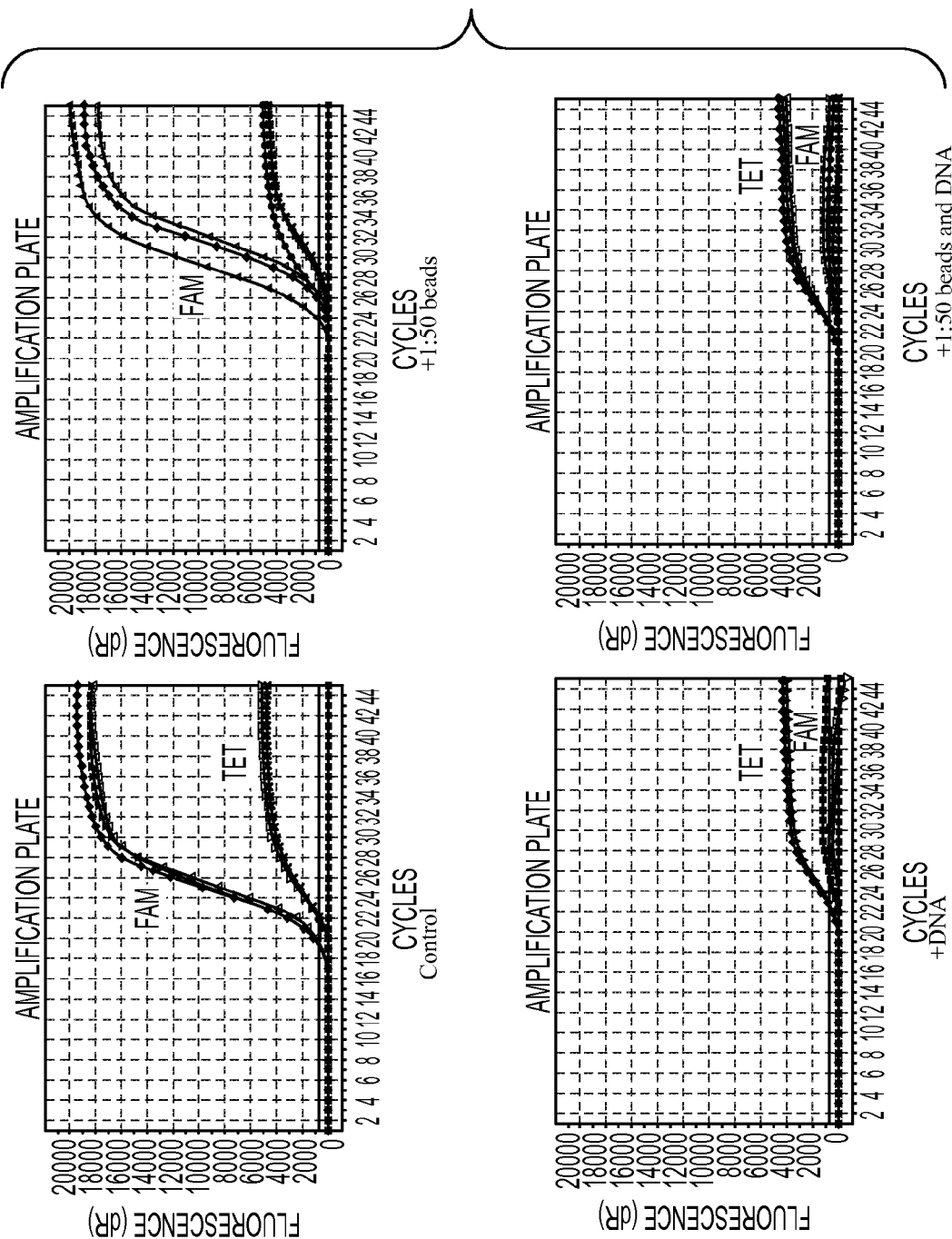

FIG. 18 demonstrates that addition of carrier DNA reverses inhibition of PCR reaction by anion exchange bead carryover. Real time PCR amplifications were performed in triplicate in the presence of 1:50 dilutions of AXpH™ beads and 0 or 100 ng/ml of carrier DNA. Fluorescent signals were generated using reporter probes labeled with either FAM (top curve) or TET (lower curve). As can be seen, carrier DNA appeared to quench any signal generated by FAM. However, use of TET dye indicated that carrier DNA reversed the inhibitory effect of the presence of the AXpH™ beads.

Figure 19A:
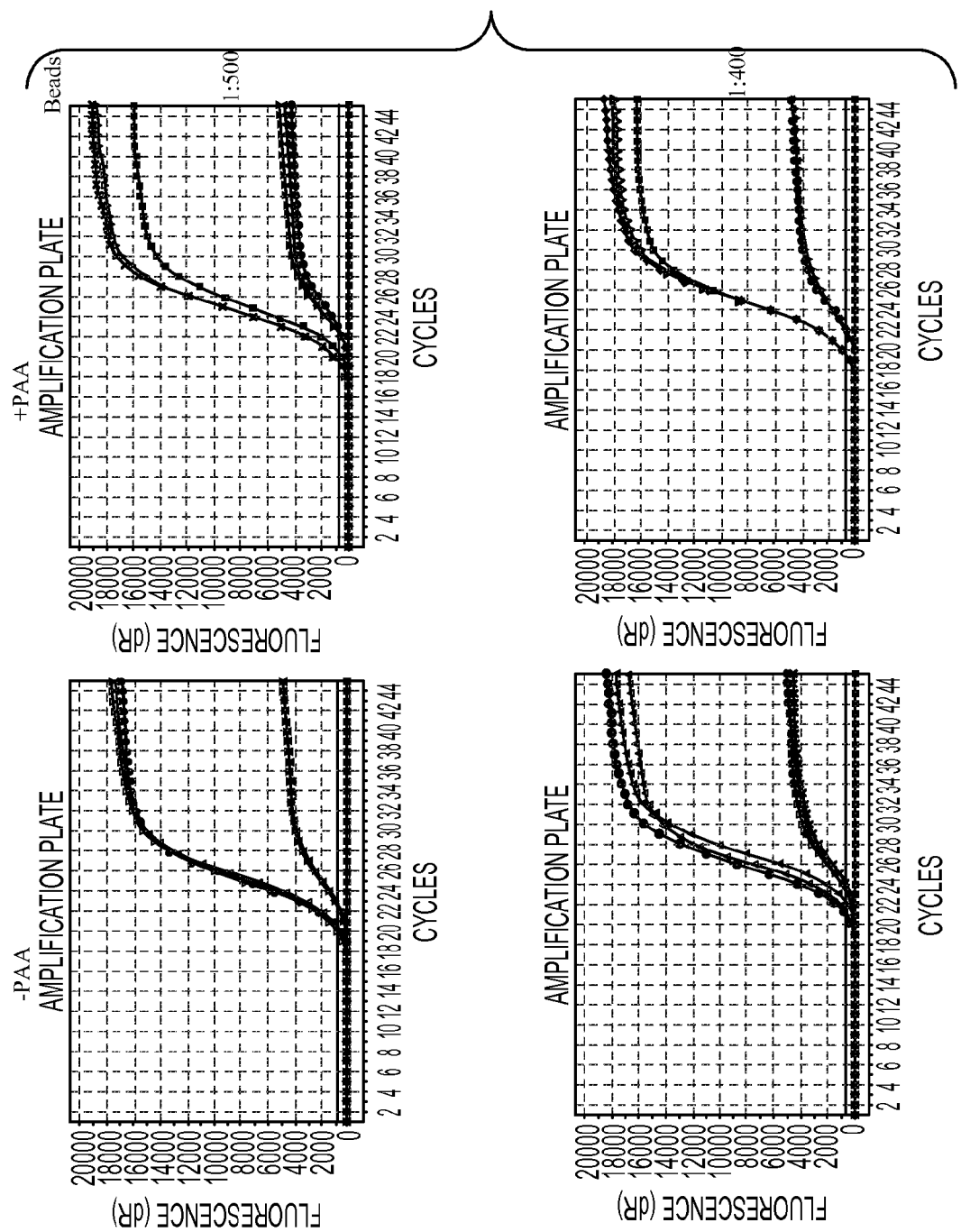
Figure 19B:
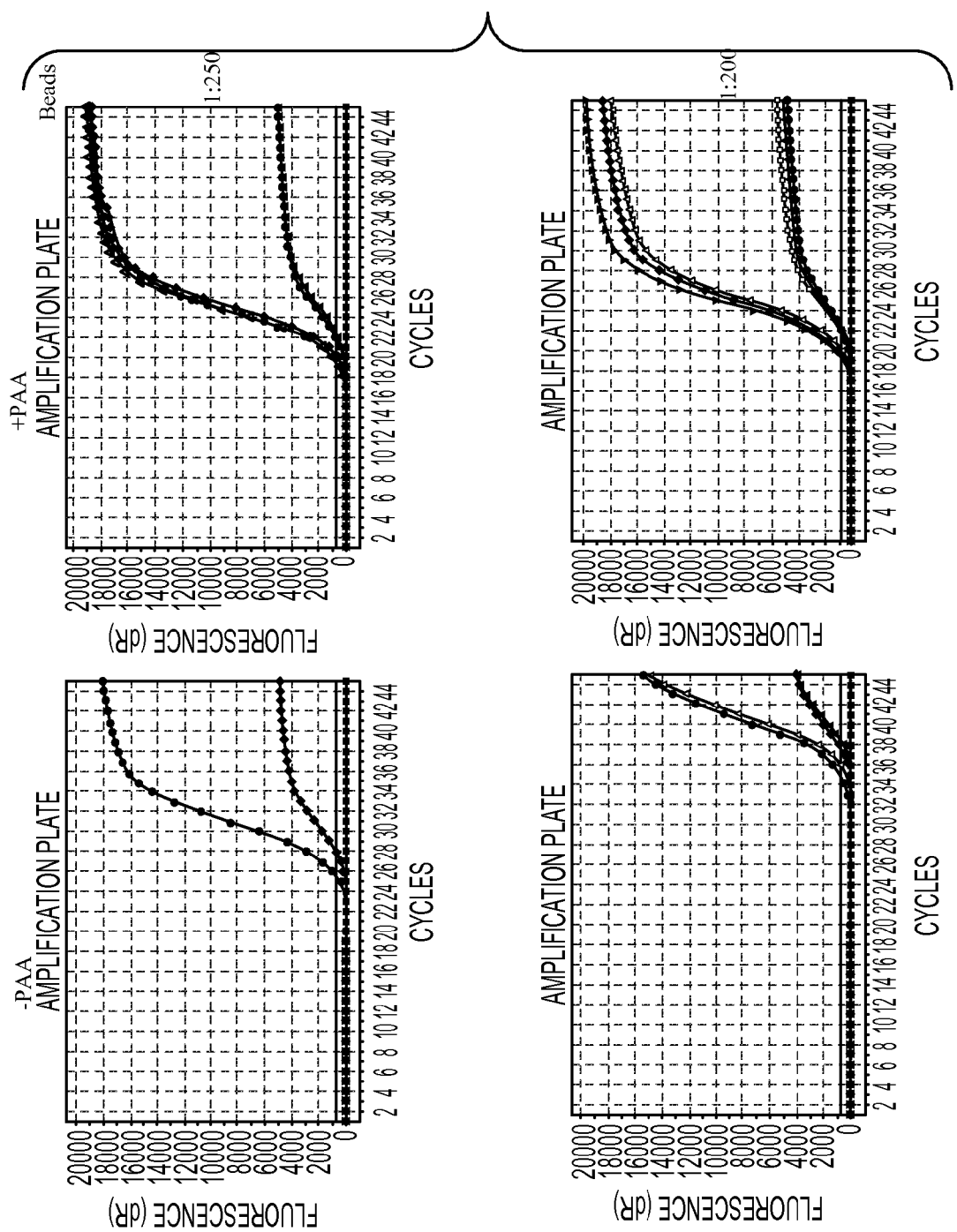

FIG. 19 demonstrates that polyacrylic acid ("PAA") also rescues PCR in the presence of anion exchange materials. Real time PCR amplifications were performed in triplicate in the presence of 1:200 (FIG. 19A), 1:250 (FIG. 19A); 1:400 (FIG. 19B); and 1:500 (FIG. 19B) dilutions of AXpH™ beads in the presence ("PAA+") or absence ("PAA−") of 25 ng/ml PAA. Fluorescent signals were generated using reporter probes labeled with either FAM (top curve) or TET (lower curve).

Figure 20A:
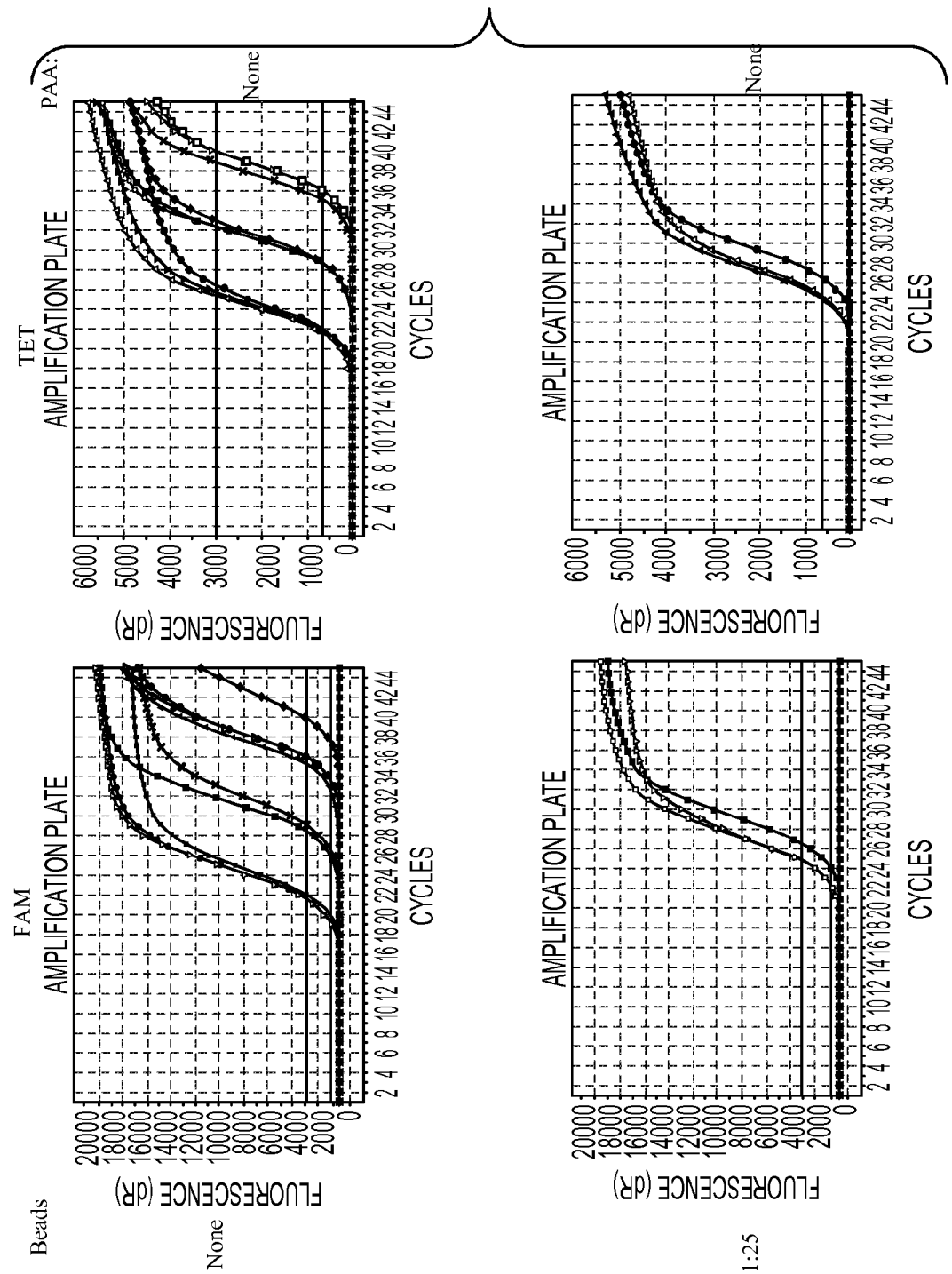
Figure 20B:
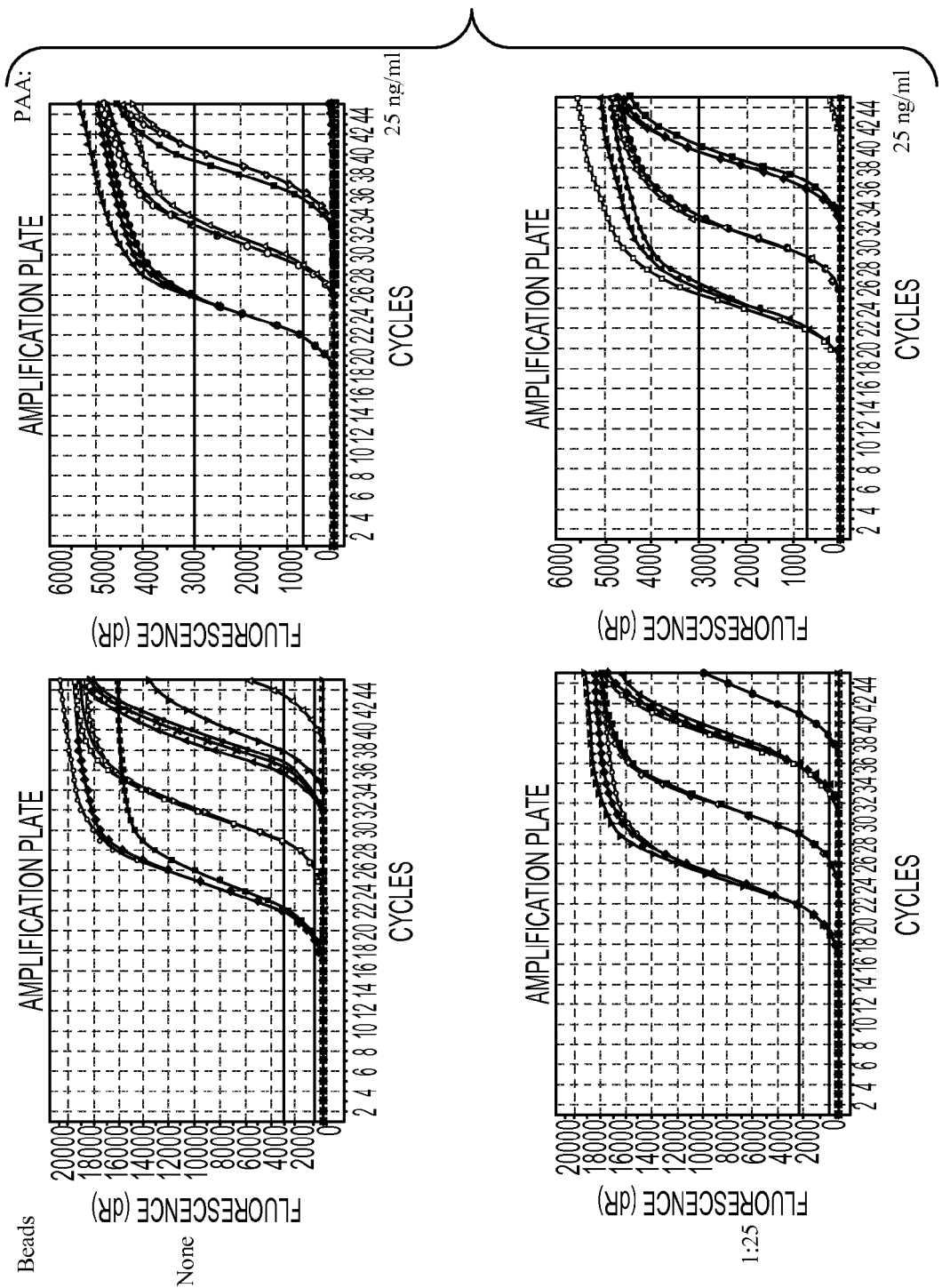
Figure 21A:
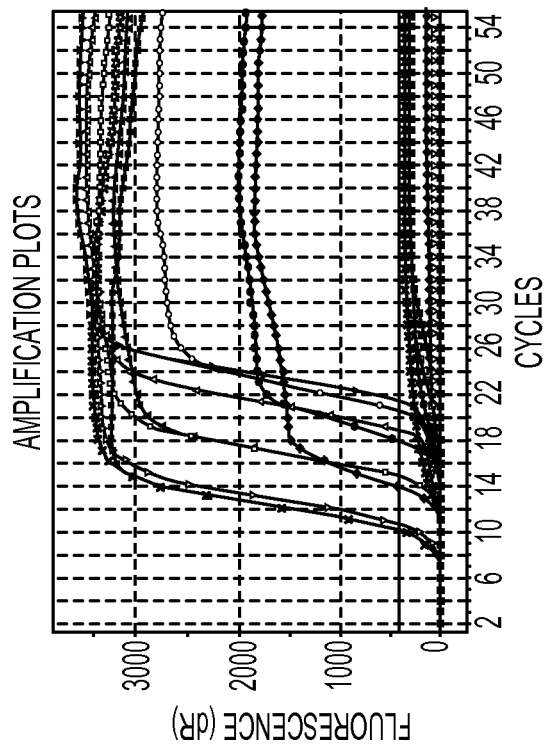
Figure 21A:
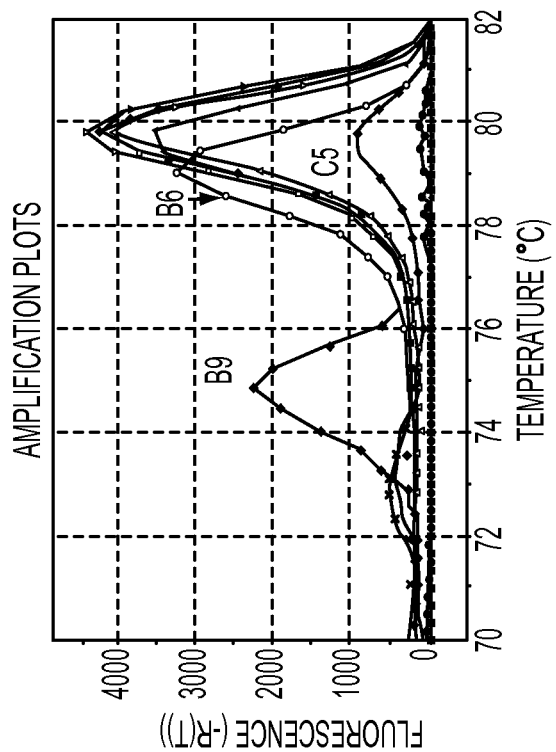
Figure 21B:
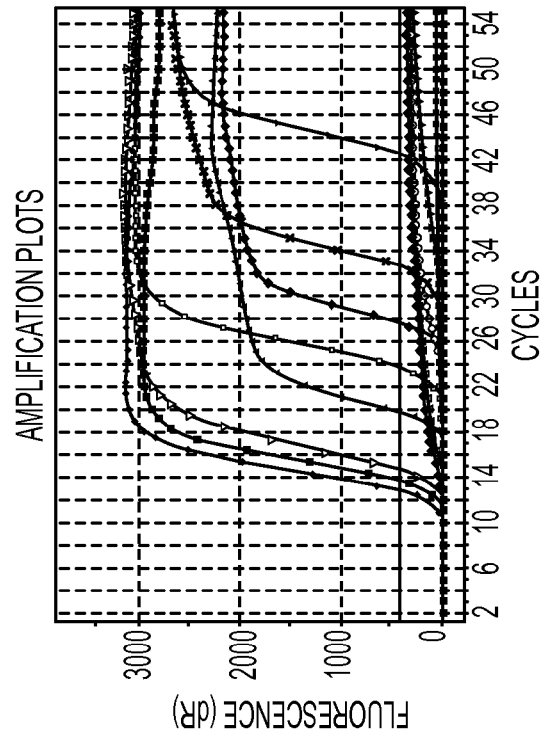
Figure 21B:
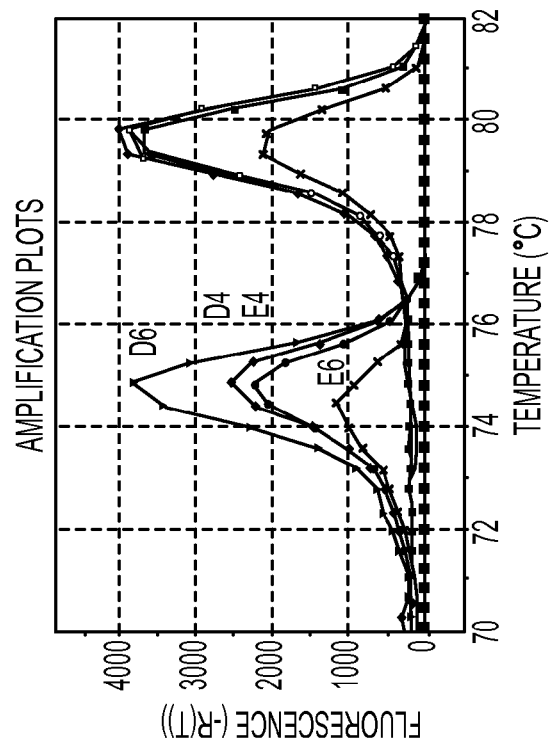
Figure 21C:
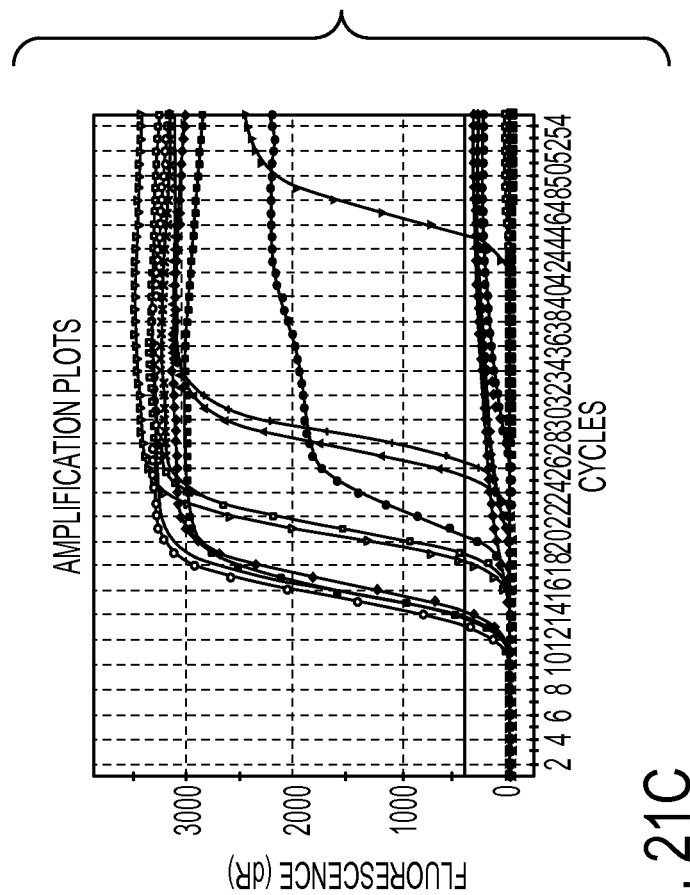
Figure 21C:
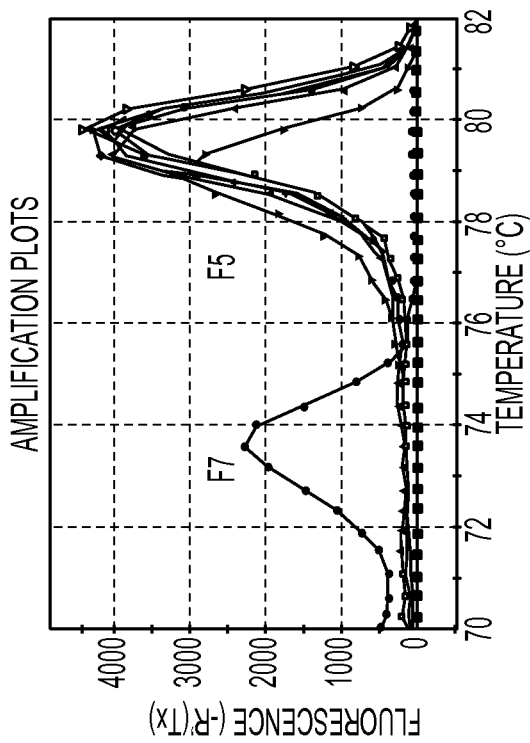

FIG. 20 demonstrates that the rescue effect of PAA an effect that holds for low target concentration in the presence of high anion exchange concentrations. Real time PCR amplifications were performed in triplicate on 10, 103, and 105 copies of a target nucleic acid in the presence of a 1:25 dilution of AXpH™ beads and 0 or 25 ng/mL PAA. Fluorescent signals were generated using reporter probes labeled with either FAM or 5'-Tetrachloro-Fluorescein dye ("TET") as indicated. As can be seen, three distinct curves are present in the control (FIG. 20A, top curves), which is extinguished by the addition of AXpH™ beads for all but the highest concentration of target nucleic acid (FIG. 20A, bottom curves). Addition of PAA reverses this effect (FIG. 20B).

FIG. 21 demonstrates the inhibitory effects of anion exchange materials on tHDA and shows that amplification can be rescued by PAA. Real time amplifications of NG DNA were performed in triplicate on 10, $10^3$, and $10^5$ copies of a target nucleic acid in the presence of a 1:25 dilution of AXpH™ beads and 0 or 25 ng/mL PAA. Fluorescent signals were generated using labeled reporter probes. FIG. 21A demonstrates control tHDA activity (no PAA or beads), FIG. 21B demonstrates tHDA activity in the presence of beads, and FIG. 21C demonstrates tHDA activity in the presence of beads and PAA.

Figure 22A:
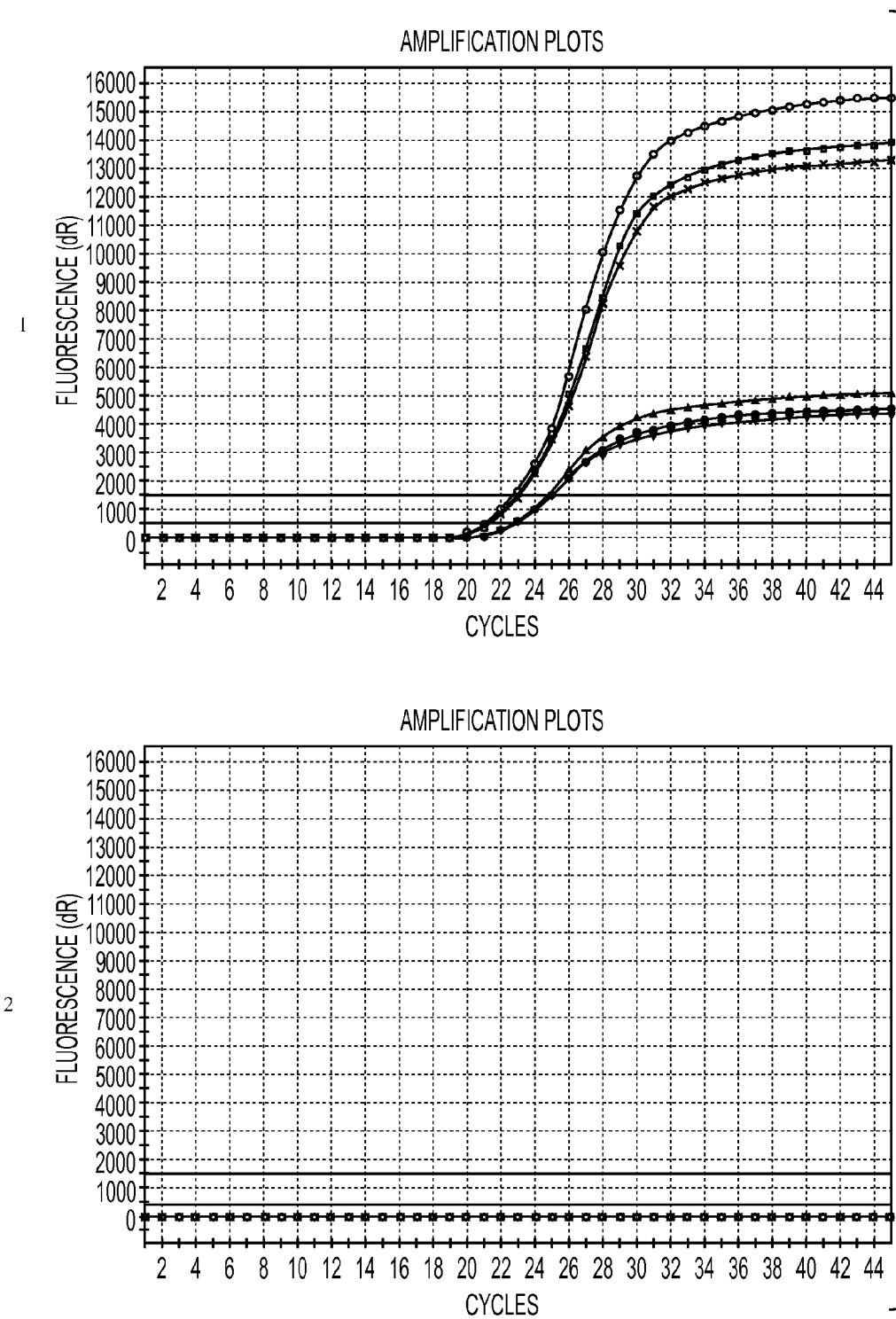
Figure 22B:
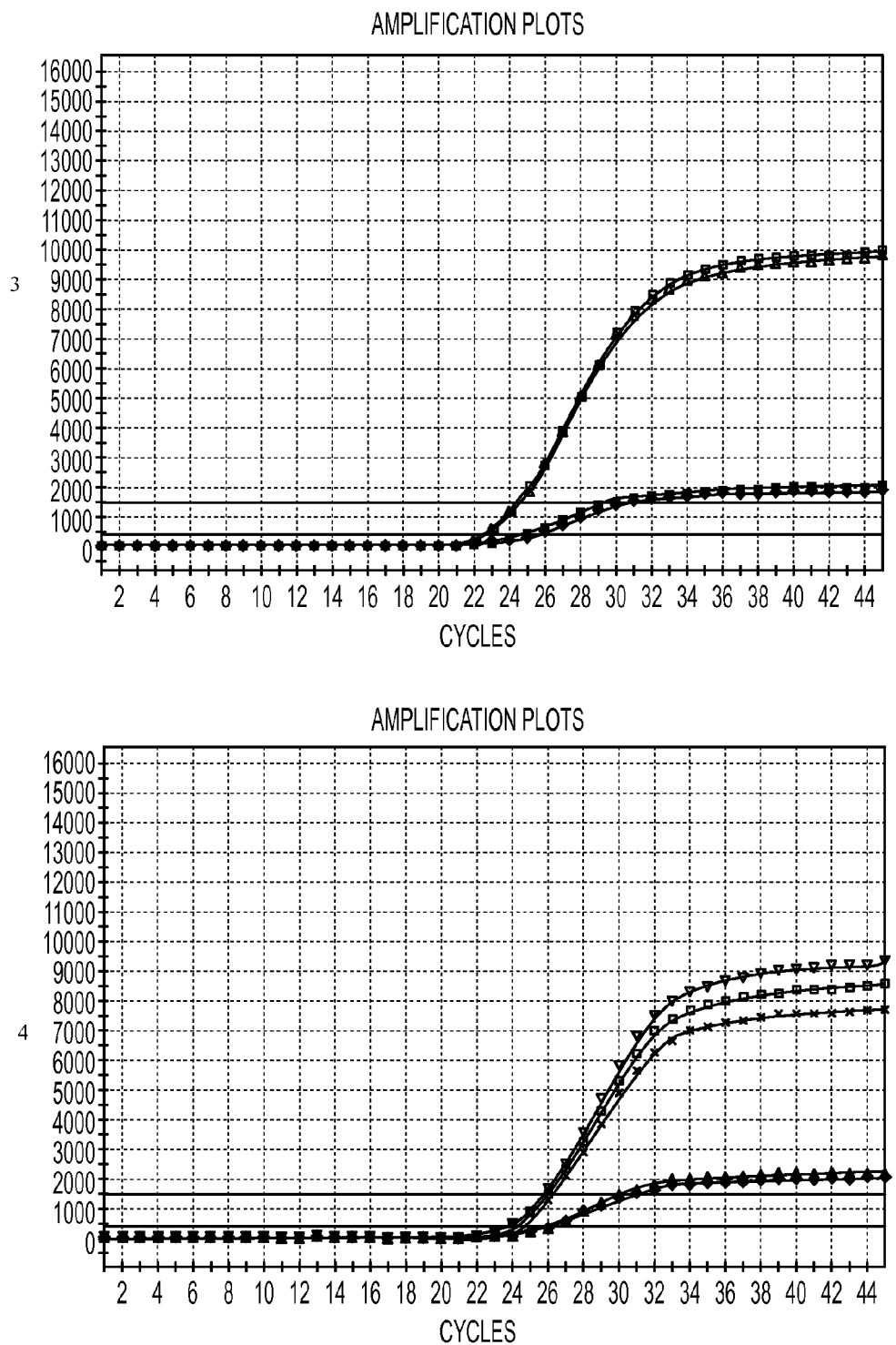
Figure 22C:
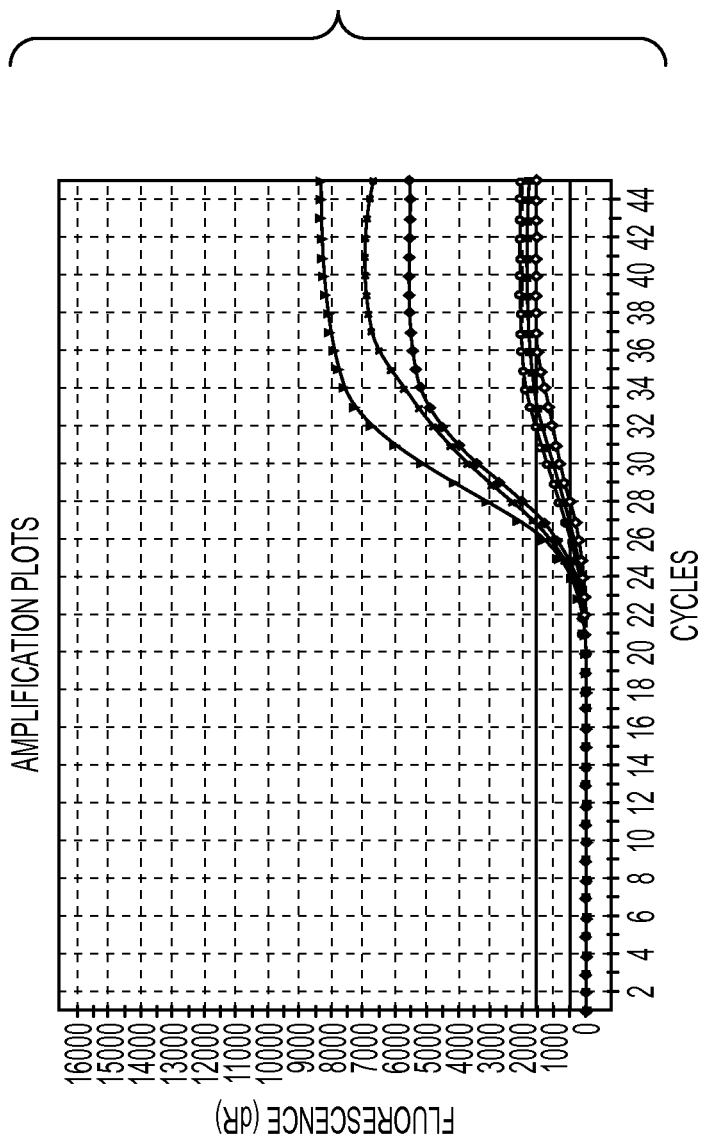

FIG. 22 demonstrates that the presence of high molecular weight PAA (PAA-H), low molecular weight PAA (PAA-L), or polymethacrylic acid ("+PMA") permits amplification of a target NG DNA in the presence of AXpH™ beads. A standard three step real time PCR reaction was performed in triplicate for all examples using TaqMan® probes labeled with either TET (top curves) or FAM (bottom curves). All amplifications were performed in the presence of 2.5 mM MgCl₂. FIG. 22A: 1 is a positive amplification control utilizing a target nucleic acid in wash buffer (10 mM Tris, pH 8; 0.1% NP-40 alternative); 2 is a bead control utilizing a target nucleic acid in wash buffer in the presence of AXpH™ beads. FIG. 22B: 3 is a target amplified in wash buffer plus PAA-H (0.25%) and AXpH™ beads; 4 is a target amplified in wash buffer plus PAA-L (0.25%) and AXpH™ beads. FIG. 22C: 5 is a target amplified in wash buffer plus PMA (0.25%) and AXpH™ beads.

Figure 23:
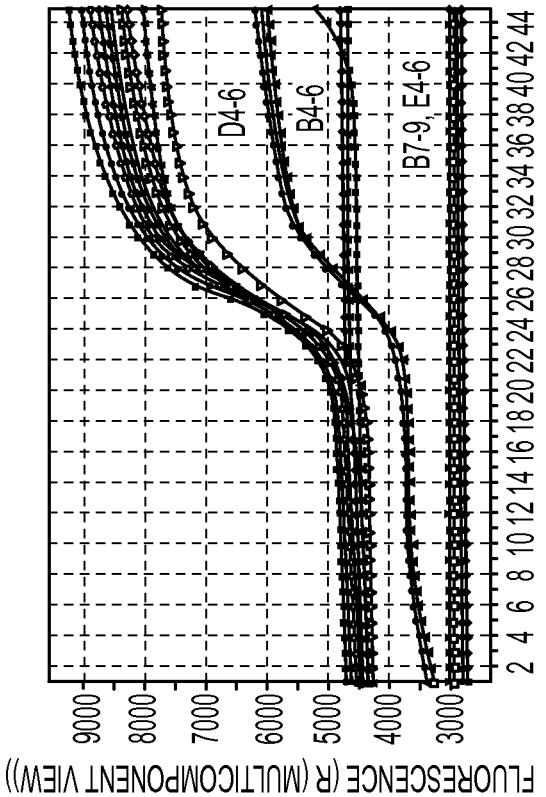
Figure 23:
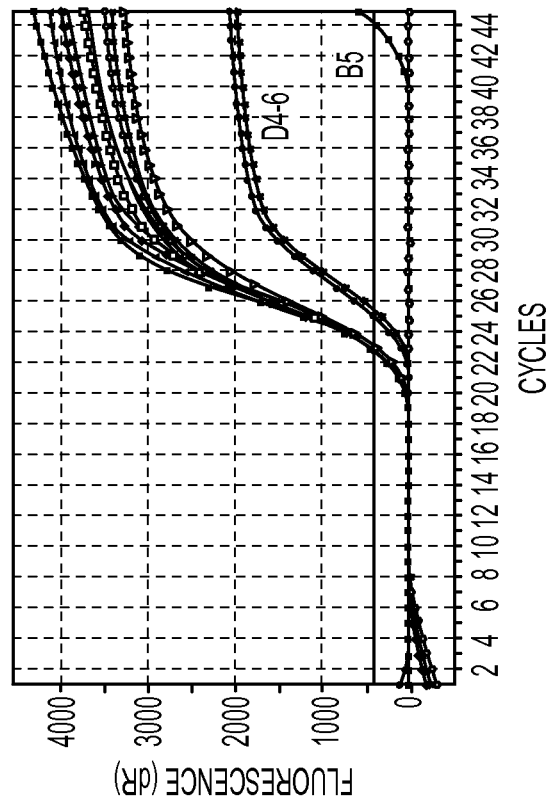

FIG. 23 demonstrates that the presence of polyglutamic acid ("PGA") permits PCR amplification in the presence of anion exchange materials. A standard three step real time PCR reaction was performed on a NG DNA in triplicate for all examples using TaqMan® probes. B7-9 is an absolute negative control using wash buffer (10 mM Tris, pH 8; 0.1% NP-40 alternative) in the absence of both target nucleic acid and AXpH™ beads. The curves at A are positive amplification controls using target nucleic acid dissolved in either wash buffer alone or wash buffer plus 1.25% PGA, 1.25% polyadenylate ("poly-A"), or 1.25% carboxymethyldextran ("CMD"). As can be seen, none of the polyanionic compounds significantly affected amplification of the target. B4-6 is a bead control to demonstrate the effect of anion exchange materials on amplification of the target. E4-6 indicates amplification of the target in the presence of 1.25% CMD and AXpH™ beads. D4-6 indicates amplification of target in the presence of 1.25% PGA and AXpH™ beads. The left plot shows the data expressed as derivative curves. The right plot shows raw data.

Figure 24:
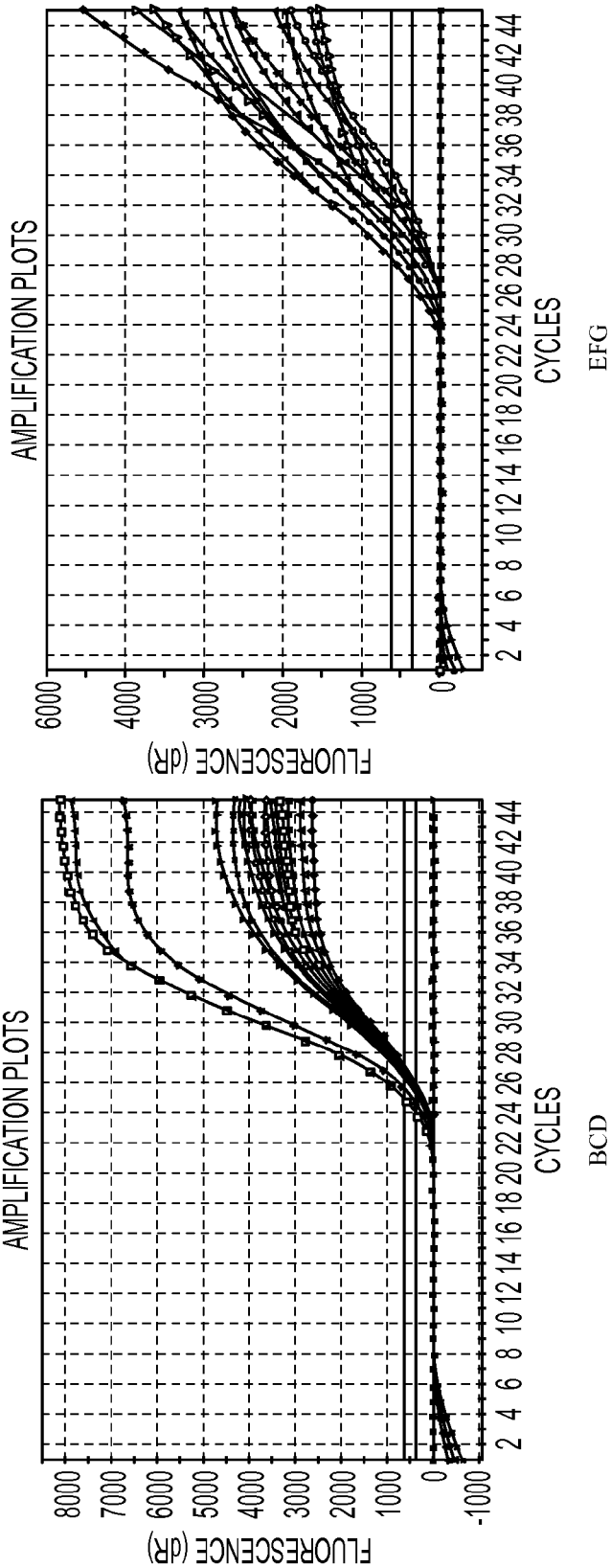

FIG. 24 demonstrates that PAA inhibits PCR, which can be corrected by increasing the concentration of $Mg^{2+}$. Target NG DNAs were amplified in the presence of either 0.05 or 0.1% PAA in the presence of two types of anion exchange materials (BCD and EFG, respectively) and 3, 7, or 11 mM $Mg^{2+}$. As can be seen in the figure, increasing the concentration of $Mg^{2+}$ reversed the inhibitory effect of PAA.

DETAILED DESCRIPTION OF THE INVENTION

It has long been known that nucleic acids can be releasably adsorbed onto certain positively ionized materials, owing to the negatively ionized phosphates of the nucleic acid backbone. This property is frequently manipulated to purify nucleic acids from complex biological materials through a procedure termed anion exchange. In the typical scenario, a solid phase is coated with "capture moieties" to form an anion exchange material. Under appropriate ionic and pH conditions, the phosphate backbone of nucleic acids will bear a net negative charge, while the capture moiety will bear a net positive charge. Thus, the nucleic acid will bind to the capture moiety, while neutrally or positively charged molecules, such as proteins, will not. The solid phase with the bound nucleic acid can then be separated from the remaining by various means, such as by centrifugation or application of a magnetic field. The anion exchange material can then be washed and, in the typical scheme, the nucleic acid eluted back into solution by altering the salt and/or pH conditions to form an eluate. The eluate can then be separated from the anion exchange material and used in subsequent analyses. Numerous such methods have been previously described. These methods are clean and easy to perform, result in relatively high nucleic acid yields, and do not require the dangerous and expensive chemicals necessary with tradition chemical extraction methods of purification. However, they do present some problems.

For example, elution of nucleic acids from anion exchange materials typically requires some combination of pH and/or ionic strength manipulation to elute bound nucleic acids from the anion exchange material. Nucleic acids eluted in this manner generally cannot be used directly in analytical methods, such as PCR, as the resulting eluate has a non-optimal pH and/or elevated ionic strength. Therefore, it would be desirable to develop materials and methods that permit elution of nucleic acids anion exchange materials at analytically appropriate pH and ion concentrations.

Accordingly, the present disclosure relates to materials, methods, and kits for isolating a nucleic acid with an anion exchange material, wherein an anionic compound comprising at least two anionic groups is added during an elution step.

In one aspect, a method of eluting a nucleic acid from an anion exchange material is disclosed, said method comprising: a) providing a nucleic acid-anion exchange complex; and b) adding a composition comprising an anionic compound comprising at least two anionic groups to the nucleic acid-anion exchange complex, wherein the anionic compound displaces the nucleic acid from the anion exchange material.

As used herein, the verb "to complex" shall refer to the process of a positively ionized capture moiety on the anion exchange material associating directly with a negatively ionized moiety on either the phosphate backbone of a target nucleic acid or an anionic compound. The noun "complex" shall refer to the chemical structure formed by such an association. The term "nucleic acid-anion exchange complex" shall refer to the chemical structure formed when a nucleic acid complexes with a positively ionizable capture moiety on an anion exchange material.

In one embodiment, the nucleic acid-anion exchange material is provided by a method comprising: (1) contacting an anion exchange material with a sample comprising a nucleic acid under conditions in which a complex forms between the anion exchange material and the nucleic acid, and (2) isolating the complex from the sample. In a further embodiment, the step of forming a complex between the anion exchange material and the nucleic acid is performed under pH, ionic strength, and/or detergent conditions such that the nucleic acid of interest complexes with the anion exchange material, but contaminants such as proteins, endotoxins, and liposomes do not. The conditions may be further refined such that only specific nucleic acids form a complex with the anion exchange material.

In another embodiment, the nucleic acid-anion exchange material is provided by a method comprising: (1) contacting a sample comprising the nucleic acid with the anion exchange material, (2) forming a complex between the anion exchange material and the nucleic acid, (3) isolating the complex from the sample, and (4) washing the complex to remove impurities. The wash conditions may be selected such that substantially all non-nucleic acid material is removed. Suitable wash buffers are known in the art and include but are not limited to solutions comprising water, alcohols in particular branched or unbranched alcohols having 1 to 5 carbon atoms, such as ethanol or isopropanol, polyethylenglycols, polypropylenglycols, acetone, carbohydrates, aqueous solutions comprising salts and mixtures of the foregoing. By way of example and not limitation, the wash buffer may comprise 0.1% NP-40 in 0.1 mM Tris, pH 8.0. The wash conditions further may be refined such that specific nucleic acids are removed as impurities as well.

Another problem with isolating nucleic acids using anion exchange materials is that the eluate often does not completely separate from the anion exchange material, resulting in analytical samples contaminated with the anion exchange material, commonly referred to as "bead carryover". This is problematic because the presence of anion exchange materials often interferes with subsequent analysis of the nucleic acid. Moreover, molecular biological analyses are increasingly automated. Ideally, one would like to combine both the isolation and the analytical methods into a single automated process with as few steps and reagents as possible. The potential for anion exchange materials interfering with analysis of the nucleic acid makes predictable and reliable automation of such processes difficult. Therefore, it would be desirable to develop materials and methods that permit analysis of nucleic acids in the presence of anion exchange materials.

Accordingly, the present disclosure relates to materials, methods, and kits for analyzing a nucleic acid in the presence of an anion exchange material and an anionic compound comprising at least two anionic groups, wherein the anionic compound reverses inhibition of the analytical process caused by the anion exchange material.

It should be understood that the analysis step of the methods disclosed herein is intended to be performed in the presence of the anion exchange material. The presence of the anion exchange material can be either unintentional, as in the case of carry-over during nucleic acid purification, or it can be intentional, as when nucleic acids are analyzed directly from the isolated nucleic acid-anion exchange complex.

Nucleic Acid

The nucleic acids according to the present disclosure are not limited and include any nucleic acid. By way of example and not limitation, the nucleic acid may be: DNA, including but not limited to genomic DNA, mitochondrial DNA, bacterial DNA, viral DNA, plasmids, cosmids, linear oligodeoxynucleotides and polydeoxynucleotides, cDNA, PCR fragments, PCR amplicons, tHDA amplicons, LCR amplicons, long-range PCR amplicons, oligonucleotides, primers, probes, artificial or synthetic DNA; RNA, including but not limited to mRNA, tRNA, rRNA, viral RNA, siRNA, miRNA, RNAi, linear oligonucleotides, linear polynucleotides, probes, artificial or synthetic RNA; artificial nucleic acids such as PNA and LNA as well as combinations thereof such as nucleic acids comprising both DNA and RNA, and hybrids thereof such as RNA:DNA hybrids; complexes of nucleic acids with other biological components. The nucleic acid may be single-stranded or double-stranded. It may contain modifications such as natural modifications and artificial modifications, and may contain artificial nucleotides comprising, e.g., artificial bases, artificial sugar moieties and/or artificial connections between the nucleotides.

Nucleic acids can include, without limitation, nucleic acids found in specimens or cultures (e.g. cellular, microbiological and viral cultures) including biological and environmental samples. The ribonucleic acids may be found in any biological samples from cell culture, bacteria, viruses, an animal, including a human, fluid, solid (e.g., stool) or tissue samples. Target nucleic acids may further be found in biological samples including, but not limited to cervical samples (e.g., a sample obtained from a cervical swab), adenoid cells, anal epithelial cells, blood, blood products such as serum, plasma or buffy coat, saliva, cerebral spinal fluid, pleural fluid, milk, lymph, sputum, urine and semen.

In other embodiments, the nucleic acids are from other viral, bacteria, mycobacteria or plasmodia, for example cytomegalovirus (CMV), herpes, HIV, *Chlamydia, Gonorrhea, Staphylococcus aureus*, tubercolis, Sars Coronavirus and/or influenza.

In one embodiment, the nucleic acids are human papillomavirus (HPV) and include genetic variants of HPV. A variant includes polymorphisms, mutants, derivatives, modified, altered, or other forms of the nucleic acid. In one embodiment, the nucleic acid is an HPV nucleic acid. In another embodiment, the HPV nucleic acid is HPV DNA and/or RNA of a high risk HPV type. In another embodiment, the nucleic acids are high risk HPV types such as, 16, 18, 31, 33, 35, 39, 45, 51, 52, 56, 58, 59, 68, 26, 66, and/or 82.

Sample Comprising a Nucleic Acid

Samples that contain nucleic acid include, but are not limited to, a specimen or culture (e.g., cellular, microbiological and viral cultures) including biological and environmental samples. Biological samples may be from any source such as cell culture, bacteria, viruses, an animal, including a human, fluid, solid (e.g., stool) or tissue samples, as well as liquid and solid food and feed products and ingredients such as dairy items, vegetables, meat and meat byproducts, and waste. Environmental samples include, for example, environmental material such as surface matter, soil, water and industrial samples, as well as samples obtained from food and dairy processing instruments, apparatus, equipment, utensils, disposable and non-disposable items. Exemplary biological samples including, but not limited to, cell samples, such as cervical epithelial cells (e.g., a sample obtained from a cervical swab), adenoid cells, anal epithelial cells, blood, blood products such as serum, plasma or buffy coat, saliva, cerebral spinal fluid, pleural fluid, milk, lymph, sputum and semen, and may be collected, for example, in Preservcyt, Surepath and/or Digene Collection Medium ("DCM"). The sample may comprise a deoxyribonucleic acid (DNA) and/or ribonucleic acid (RNA).

The sample may be processed prior to contacting it with the anion-exchange material if desired for any reason. For example, a biological sample comprising cells comprising nucleic acids may be treated to lyse the cells in order to release the nucleic acid. The lysate comprising the nucleic acids may then be added to the anion-exchange material. One skilled in the art would appreciate desirable methods for treating a sample containing nucleic acids before contacting the solution with an anion-exchange material. For example, the cells may be lysed with a suitable lysis buffer comprising, for example, 2% Triton X-100, 0.2 M EDTA, 40 mM sodium citrate, 40 mM boric acid in 100 mM Tris HCl, pH 7.0. If an alkali lysis buffer is used to prepare the sample, the pH of the sample may need to be neutralized to a pH that allows the nucleic acids to bind to the anion-exchange material prior to contacting the sample with the anion-exchange material.

In other embodiments, the sample may comprise nucleic acids from other viral, bacteria, mycobacteria or plasmodia, for example cytomegalovirus (CMV), herpes, HIV, *Chlamydia, Gonorrhea, Staphylococcus aureus*, tubercolis, Sars Coronavirus or influenza.

In a further embodiment, the sample is treated such that the nucleic acid is "free." As used herein, the phrase "free nucleic acid" shall indicate that the nucleic acid is not associated with large macromolecular structures, such as vesicles, liposomes, micelles, ribosomes, nuclei, mitochondria, viral caspids and/or envelopes, endosomes, or exosomes.

Anion-Exchange Material

The present disclosure advantageously utilizes anion exchange material. The terms "anion exchange material", "anion exchange material", "anion exchange matrix" and "anion exchange resin" are used synonymously herein and in particular are not restricted to materials which are resins in the chemical meaning. As used herein, the term "anion exchange material" shall refer to any material that can be used to selectively remove nucleic acids from a solution via the formation of a complex between the phosphate backbone of the nucleic acid and a positively ionizable capture moiety of the material.

Numerous anion exchange materials have previously been described and would be immediately recognized by a person having ordinary skill in the art, including for example those described in U.S. Pat. No. 6,914,137, U.S. Pat. No. 5,990,301, US 20100009351A1, and EP 0 268 946 B1, the disclosures of which are hereby incorporated by reference. Any anion exchange material suitable for purifying nucleic acids may be used.

In one aspect, the anion exchange material comprises a solid phase and a positively ionizable capture moiety.

Any solid phase suitable for anion exchange chromatography may be used, including but not limited to silica, borosilicates, silicates, anorganic glasses, organic polymers such as poly(meth)acrylates, polyurethanes, polystyrene, agarose, polysaccharides such as cellulose, metal oxides such as aluminum oxide, magnesium oxide, titanium oxide and zirconium oxide, metals such as gold or platinum, agarose, sephadex, sepharose, polyacrylamide, divinylbenzene polymers, styrene divinylbenzene polymers, dextrans, and derivatives thereof, and/or silica gels, beads, membranes, and resins; glass or silica surfaces, such as beads, plates, and capillary tubes; magnetizable or magnetic (e.g. paramagnetic, superparamagnetic, ferromagnetic or ferrimagnetic) particles, including but not limited to polystyrene, agarose, polyacrylamide, dextran, and/or silica materials having a magnetic material incorporated therein or associated therewith. In some embodiments, the capture moieties can be linked to the surfaces of the processing vessels such as micro-tubes, wells of micro-plates, or capillaries, and using these surfaces nucleic acids can be isolated on a micro scale. In one embodiment, the solid phase will be treated, manufactured, or otherwise processed such that the nucleic acid of interest will not bind directly to the solid phase during the purification step.

Anion exchange materials include, but are not limited to, materials modified with positively ionizable capture moieties. Examples of such ionizable groups are monoamines, diamines, polyamines, and nitrogen-containing aromatic or aliphatic heterocyclic groups. In one embodiment, the positively ionizable capture moiety comprises at least one primary, secondary or tertiary amino group. In another embodiment, the positively ionizable capture moiety is selected from the group consisting of a primary amine of the formula $R_3N$, a secondary amine of the formula $R_2NH$, and a tertiary amine $X-(CH_2)_n-Y$, wherein:
  X is $R_2N$, RNH or $NH_2$,
  Y is $R_2N$, RNH or $NH_2$,
  R is independently of each other a linear, branched or cyclic alkyl, alkenyl, alkynyl or aryl substituent which may comprise one or more heteroatoms, preferably selected from O, N, S and P, and
  n is an integer in the range of from 0 to 20, preferably 0 to 18.

Examplary capture moieties include, but are not limited to, aminomethyl (AM), aminoethyl (AE), aminoalkyl, alkylaminoalkyl, dialkylaminoalkyl such as diethylaminoethyl (DEAE), ethylendiamine, diethylentriamine, triethylentetraamine, otetraethylenpentaamine, pentaethylenhexaamine, trimethylamino (TMA), triethylaminoethyl (TEAE), linear or branched polyethylenimine (PEI), carboxylated or hydroxyalkylated polyethylenimine, jeffamine, spermine, spermidine, 3-(propylamino)propylamine, polyamidoamine (PAMAM) dendrimers, polyallylamine, polyvinylamine, N-morpholinoethyl, polylysine, and tetraazacycloalkanes.

Biological buffer compounds also may be used as functional groups of the anion exchange material, such as those described in the patents or applications U.S. Pat. No. 6,914, 137 and EP 1 473 299. Further examples of the positively ionizable groups are polyhydroxylated amines, detergents, surfactants, heterocycles, dyes, negatively charged groups in combination with metal ions or metal oxides, histidine and polyhistidine. Such groups are also described, for example, in the patent application WO 2003/101494 and patent application EP 09 007 338.8. Also zwitterionic groups such as amino acids or betaines may be used. In one embodiment, the anion exchange material comprises spermine-modified magnetic silica beads.

The solid phase may be functionalized for attachment of the capture moieties, for example with functionalities such as Si—O—Si, Si—OH, alcohol, diol or polyol, carboxylate, amine, phosphate or phosphonate. The positively ionizable capture moieties may be attached to the solid phase, for example, by using epoxides, (activated) carboxylic acids, acid anhydrides, acid chlorides, formyl groups, tresyl groups or pentafluorophenyl groups. The functional groups may be attached directly to the solid phase or via (linear or branched) spacer groups, e.g. hydrocarbons such as $-(CH_2)_n-$ groups, carbohydrates, polyethylenglycols and polypropylenglycols. Alternatively, a polymer composed of monomers comprising a capture moiety such as an amino functional group can be used as anion exchange material.

In some embodiments, ionizable groups can be linked to the surfaces of processing vessels, such as micro-tubes, micro-plates, or capillaries, and using these surfaces nucleic acids can be isolated on a micro scale.

In a further embodiment, the solid phase is treated, manufactured, or otherwise processed such that the nucleic acid of interest will not bind directly to the solid phase during the purification step.

In one embodiment, a PEI-modified paramagnetic silica bead is used as the anion exchange material. Exemplary PEI-modified magnetic silca beads include AXpH™ beads (commercially available from Qiagen GmbH, Hilden Germany). AXpH™ beads can be separated magnetically from wash buffer and eluate, which is easier than the filtration needed when working with cellulose and other non-magnetic resins.

Nucleic Acid Binding

The ion exchange process known in the art usually involves two primary steps: (1) binding nucleic acids to the anion-exchange material at a pH that causes the material to be positively charged; and (2) elution and/or displacement of nucleic acids from said material, by either increasing salt concentration and/or increasing the pH above the pKa of the capture moieties ("pH shift method"). In the present disclosure, a solution comprising at least one compound comprising at least two anionic groups is applied to the anion-exchange material to elute the nucleic acids.

It will be understood by the person having ordinary skill in the art that the precise ionic and pH conditions necessary to cause complex formation and elution necessarily depends on both the identity and the concentration of both the capture moiety and the nucleic acid of interest. Methods of charging the anion-exchange material to prepare it for loading the nucleic acid are known to those skilled in the art.

In one aspect, the positively ionizable capture moiety bears a first net positive charge at a first pH and ionic strength and either a neutral charge or a second net positive charge that is lower than the first net positive charge at a second pH and ionic strength, such that the nucleic acid of interest binds to the positively ionizable capture moiety at the first pH and ionic strength and is released at the second pH and ionic strength.

In a further aspect, the positively ionizable capture moiety bears a first net positive charge at a first pH and ionic strength and a second net positive charge at a second pH and ionic strength, wherein a first nucleic acid and a second nucleic acid bind to the positively ionizable capture moiety at the first pH and ionic strength and the first nucleic acid, but not the second nucleic acid, is released from the positively ionizable capture moiety at the second pH and ionic strength.

The binding of the nucleic acid to the anion exchange material is usually done in an aqueous solution, preferably comprising buffer substances. Suitable biological buffers are CHAPS, MES, HEPES, MOPS, TRIS, TRICINE and PIPES. Furthermore, the solution may contain chaotropic salts such as sodium perchlorate, guanidium hydrochloride, and guanidium thiosulfate, as described, e.g., in U.S. Pat. No. 5,234,809, and/or cosmotropic salts such as ammonium sulfate, zinc sulfate, potassium sulfate and cobalt sulfate, as described, e.g., in WO 2004/055207. The binding buffer may also contain further salts such as chlorides, sulfates, phosphates, acetates, formiates, citrates, azides, and nitrates, as well as further organic compounds such as alcohols, diols, triols, polyols, polyethylenglycols, polypropylenglycols, acetone, acetonitrile, urea, guanidine, carbohydrates and surface-active substances such as surfactants or detergents, for example tween, triton, brij, nonidet or pluronic. Salts preferably are present in a concentration of about 1 M or less, preferably 0.5 M or less, more preferably 250 mM or less, most preferably 100 mM or less. Binding of the nucleic acids is preferably done at a pH in the range of about 3 to about 10, preferably about 5 to about 9.

Furthermore, binding of the nucleic acid to the anion exchange material may be combined with a treatment of the sample such as lysis of cells or tissue in the sample or digestion of specific compounds such as proteins, DNA and/or RNA in the sample. To this end, the binding buffer may further comprise lysis agents such as enzymes, surfactants, chaotropic salts or chelators (e.g. EDTA or NTA), and/or digestion agents such as proteases, DNases and RNases. These sample treatment, however, may also be done in a preceding step prior to the binding of the nucleic acid to the anion exchange material (see also above).

Binding, as well as pre-treatment steps such as lysis and/or enzymatic pretreatment processes can be performed at elevated temperatures in order to speed up the respective processes.

It may be possible to wash the anion exchange material after the sample has been added to the anion exchange material to remove unbound material in the sample, such as proteins, polysaccharides, et cetera. Suitable washing buffers which can be used to remove non-target materials are known in the prior art and include but are not limited to solutions comprising water, alcohols in particular branched or unbranched alcohols having 1 to 5 carbon atoms, such as ethanol or isopropanol, polyethylenglycols, polypropylenglycols, acetone, carbohydrates, aqueous solutions comprising salts and mixtures of the foregoing. An exemplary wash buffer comprises, for example, 0.1% NP-40 in 0.1 mM Tris, pH 8.0.

Elution

After the nucleic acid is bound to the anion exchange material, the bound nucleic acid can be eluted by adding a solution comprising an anionic compound comprising at least two anionic groups or a mixture of such anionic compounds.

1. Anionic Compound

The anionic compound(s) displaces the nucleic acids from the anion exchange material. The present method does not need to involve a change in pH in particular above the pKa of the capture moiety to cause elution, but rather relies on the anionic compound(s) to elute nucleic acid from anion-exchange material bound with nucleic acid. The anionic compound(s) can displace nucleic acid from anion-exchange materials at relatively low concentrations due to their own high selectivity to the material.

The optimal concentration of anionic compounds to be used in the eluate should be determined for any particular application; this concentration should be high enough to provide high recovery of nucleic acids, but not too high to compromise any subsequent operations and processes. The anionic compounds may be used at varying concentrations necessary to elute the nucleic acid. For example, the concentration may be 0.1% to about 2.0% and in certain embodiments, the concentration is from about 0.5% to about 1.0%. It is understood that any numerical value recited herein includes all values from the lower value to the upper value (and including the lower value and the upper value). For example, all possible combinations of numerical values between the lowest value and the highest value enumerated are to be considered expressly stated in this application. For example, for a concentration range stated as 0.025% to about 2.5%, it is intended that values such as 0.05, 0.2, 0.3, 0.4, 1.8, 1.9, etc. or any ranges within this range such as 0.3 to 1.0 or 0.4 to 2.4, etc., are expressly enumerated in this specification. These low concentrations have little or no effect on subsequent detection/analysis steps such as amplification or enzymatic reactions. Thus, the eluate can be used directly without a neutralization step typically required when using pH based or a desalting step when using a salt buffer based elution.

As used herein, "anionic compound" shall refer to any compound having a net negative charge at the pH and salt conditions used to elute or analyze the nucleic acid.

As used herein, the phrase "anionic group" shall refer to any functional group, covalently bound to the anionic compound, that bears a net negative charge at the pH and salt conditions used to elute or analyze the nucleic acid. In all cases, each anionic group of each anionic compound may be the same or different.

Suitable anionic compounds include polyanionic compounds, as well as non-polymeric anionic compounds. Preferably, the anionic compound is organic.

Suitable non-polymeric anionic compounds useful in the methods and compositions disclosed herein include, for example, any non-polymeric organic compounds comprising at least two anionic groups. By way of example and not limitation, the non-polymeric anionic compound may comprise at least 2, at least 3, at least 4, at least 5, or at least six anionic groups. In another embodiment, the non-polymeric anionic compound comprises from 2 to 6 or 3 to 6 anionic groups. In another embodiment, the non-polymeric anionic compound may comprise not more than 15 anionic groups, not more than 10 anionic groups, not more than 8 anionic groups, or not more than 6 anionic groups. The non-polymeric organic anionic compound preferably has 2 to 40 carbon atoms, more preferably 2 to 20 carbon atoms, even more preferably 2 to 12 carbon atoms. It may be linear, branched or cyclic and may be aliphatic (being saturated or unsaturated) or aromatic (having one or more conjugated or fused rings).

In one embodiment, the at least two anionic groups are selected from the group consisting of a carboxylic acid group, a sulfonic acid group, a phosphonic acid group, a phosphate group, a carbonate group, and combinations thereof.

As used herein, the term "acid group" shall encompass both the referenced acid and, alternatively, its conjugated base.

In one embodiment, the at least two anionic groups are selected from the group consisting of: a carboxylate group, a sulfonate group, a phosphonate group, and an ionized phosphate group. In another embodiment, the anionic group is a carboxylic acid/carboxylate group. In another embodiments, the non-polymeric anionic compound is selected from the group consisting of a dicarboxylic acid, tricarboxylic acid, tetracarboxylic acid, pentacarboxylic acid, hexacarboxylic acid, heptacarboxylic acid, octacarboxylic acid, nonacarboxylic acid, and a decacarboxylic acid.

In another embodiment, the non-polymeric compound comprising at least two anionic groups is a carboxylic acid, such as oxalic acid, fumaric acid, glutaric acid, maleic acid, malic acid, malonic acid, succinic acid, glutaric acid, adipic acid, pimelic acid, suberic acid, azelaic acid, tartronic acid, tartaric acid, citric acid, isocitric acid, citraconic acid, mesaconic acid, itaconic acid, aconitic acid, propane-1,2,3-tricarboxylic acid, aconitic acid, butane-1,2,3,4-tetracarboxylic acid, triethyl-1,1,2-ethanetricarboxylic acid, cyclopropane dicarboxylic acid, cyclobutane dicarboxylic acid, cyclobutane tricarboxylic acid, cyclopentane dicarboxylic acid, cyclohexane dicarboxylic acid, cyclohexane tricarboxylic acid, cyclohexane tetracarboxylic acid, cyclohexane hexacarboxylic acid, cyclooctane dicarboxylic acid, phthalic acid, isophthalic acid, terephthalic acid, hemimellitic acid, trimellitic acid, trimesic acid, mellophanic acid, prehnitic acid, pyromellitic acid, benzene pentacarboxylic acid, and mellitic acid, hexacarboxylic acid of dierythritol, octaacetic acid of trierythritol, iminodiacetic acid, nitrilotriacetic acid, ethylenediamine tetraacetic acid, diethylenetriamine pentaacetic acid, α-ketoglutaric acid, glutamic acid, aspartic acid, dicarboxymalonic acid, (18-crown-6)-2,3,11,12-tetracarboxylic acid, oligomers of 2 to 10, preferably 2 to 6, polymerizable or condensable acidic monomers such as acrylic acid, methacrylic acid, or vinylacetic acid.

In another embodiment, the non-polymeric compound comprising at least two anionic groups is an organosulfonic acid, such as methyl disulfonic acid, ethyl disulfonic acid, benzene disulfonic acid, phenole disulfonic acid, or naphthalene disulfonic acid.

In another embodiment, the non-polymeric compound comprising at least two anionic groups is an organophosphonic acids, such as hydroxyethane diphosphonic acid.

In another embodiment, the non-polymeric compound comprising at least two anionic groups is an organophosphate.

In another embodiment, the non-polymeric compound comprising at least two anionic groups is a carbonate.

In another embodiment, the non-polymeric compound comprising at least two anionic groups is a diacetylacetone.

In another embodiment, the non-polymeric anionic compound is selected from the group consisting of oxalic acid, mellitic acid, pyromellitic acid and citric acid.

The non-polymeric anionic compound may optionally be substituted, as long as the substituents do not interfere with or inhibit the ability of the compound to displace the nucleic acid from the anion exchange material. Exemplary substituents include, for example, halogen atoms such as fluorine, chloride, bromide or iodine, and hydroxyl, oxy, aldehyde, keto, alkoxy, ether, ester, amino, thiol, thioether, thioester, linear or branched alkyl, alkenyl, alkynyl, saturated or unsaturated cycloalkyl and aryl groups. In one embodiment, the anionic compound comprises 1 to 6 substituents or 1 to 3 substituents. In another embodiment, these substituents comprise—if present—not more than 20, 10, 8, 6, 4 or 2 carbon atoms.

In one embodiment, the non-polymeric anionic compound is a low molecular weight compounds. In another embodiment, the non-polymeric anionic compound has a molecular weight of 5,000 Da or less. In another embodiment, the non-polymeric anionic compound has a molecular weight of 3,000 Da or less. In another embodiment, the non-polymeric anionic compound has a molecular weight of 2,000 Da or less.

Non-polymeric anionic compounds having at least two anionic groups have the advantage that only relatively low concentrations of the anionic compound are necessary to effectively elute the bound nucleic acid. Furthermore, the presence of non-polymeric anionic compounds do not interfere with or inhibit subsequent amplification reactions, even at rather high concentrations.

In another aspect, the anionic compound comprising at least two anionic groups is a polyanionic compounds. As used herein, the phrase "polyanionic compound" shall refer to a polymeric anionic compound.

In one embodiment, the polyanionic compound is selected from the group consisting of: polymerized unsaturated carboxylic acids (e.g. acrylic, methacrylic, maleic, etc.) or copolymers of these acids with other monomers, such as acrylamide or acrylonitrile; acidic polypeptides such as polyglutamic or polyaspartic acid, or copolymers of acidic polypeptides with other amino acids; modified dextran and other modified or polyanionic polycarbohydrates bearing covalently attached ionized groups, such as carboxymethyl dextran, dextran sulfate and dextran phosphate or mixtures thereof; polystyrene with anionic groups, such as polystyrenesulfonates; and even other nucleic acids such as double-stranded or single-stranded DNA or RNA, or analogs thereof such as "base-free" nucleic acid (nucleic acid which only comprises the backbone structure and does not comprise any bases attached to the sugar moieties). In another embodiment, polyacrylic acid (PAA), polymethacrylic acid (PMA), polyglutamic acid (PGA), and/or dextran sulfate (DS) are selected. In another embodiment, a "low molecular weight" polyacrylic acid (a weight average Fw~5,100; approximately a 70-mer) is selected. In another embodiment, "high molecular weight" polyacrylic acid (a weight average Fw>200,000; i.e. longer than a 2,800-mer), is selected.

In one embodiment, the polyanionic compound is a second nucleic acid. When using a second nucleic acid for elution of the bound, first nucleic acid, the second nucleic acid should not interfere with the subsequent process (e.g. RNA can be used to elute DNA if the next step is PCR analysis). The second nucleic acid preferably comprises at least 100 base pairs (bp), more preferably at least 200 bp, at least 500 bp or at least 1000 bp. It may be, for example, plasmid DNA or genomic DNA or a carrier nucleic acid, such as polydeoxyadenosine ("poly-dA"), polydeoxythymidine ("poly-dT") or a co-polymer of polydeoxyadenosine and polydeoxythymidine ("poly-dA:dT")

The anionic compound may be added in the presently disclosed methods either as free acid or as a salt. Suitable cations for use in such salts are, for example, any alkaline cation, such as sodium and lithium.

2. Elution

Elution of the bound nucleic acid from the anion exchange material is achieved using the anionic compound comprising at least two anionic groups as defined herein. Preferably, elution is performed using an elution buffer containing the anionic compound. The elution buffer preferably is an aqueous solution which may further contain, for example, a buffering agent, e.g. as described above with respect to the binding solution, organic components and/or salts. In one embodiment, the pH used for elution preferably is in the range of from about 5 to about 13, from about 5 to about 9.5, or from about 5 to about 8.5. In another embodiment, the pH lies in a range from about 8.2 to about 9.0, in particular when the eluate is supposed to be used directly in a amplification reaction such as PCR, RT-PCR, or a isothermal amplification reaction.

Elution of nucleic acids from the anion exchange material can be performed without the necessity of severe changes in the pH. In one embodiment, the pH during the elution step does not render the anion exchange material neutral or negatively charged. In another embodiment, the pH during elution does not significantly reduce the positive charge of the anion exchange material. In yet another embodiment, the pH during the elution step is not above the pKa of the anion exchange material and/or the capture moieties thereof.

In another embodiment, the solution used for eluting the nucleic acid from the anion exchange material does not comprise a high salt concentration. In another embodiment, the total salt concentration in the elution solution does not exceed 1 M, is at or below 0.5 M, 300 mM, 200 mM, 150 mM, 100 mM, 50 mM or 30 mM. In another embodiment, the elution solution does not contain any salts except for the anionic compound comprising at least two anionic groups.

Nucleic acids in biological samples are preferably first bound to anion-exchange material, for example, anion-exchange magnetic beads. The material is then washed to get rid of proteins and other undesirable impurities. Nucleic acids are then eluted by a solution comprising at least one anionic compound comprising at least two anionic groups as defined herein. This procedure requires no change or at least no severe change in pH for the elution step. In fact, the pH of the wash and elution buffer can be the same.

During elution, the anionic compound is present in a concentration high enough to effect elution of at least a part of the bound nucleic acids. In one embodiment, the anionic compound is present in a concentration high enough to effect elution of a majority of the bound nucleic acids. In one embodiment, the anionic compound is present in a concentration high enough to effect elution of substantially all of the bound nucleic acids. As just one example, the concentration of a non-polymeric anionic compound during elution is selected in the range of from about 1 mg/l to about 1 g/l, more preferably from about 10 mg/l to about 500 mg/l, even more preferably from about 20 mg/l to about 100 mg/l. As another example, the amount of the polyanionic compound is in the range of from about 0.01% to about 5%, more preferably from about 0.025% to about 2.5%, even more preferably from about 0.1% to about 2.0% or from about 0.5% to about 1.0%.

The optimal concentration of anionic compounds to be used in the eluate should be determined for any particular application. Namely, the concentration should preferably be high enough to provide high recovery of nucleic acids, but not too high to compromise any subsequent operations and processes. On the other hand, if the anionic compounds used in nucleic acid isolation step decrease efficiency of the subsequent procedures such as amplifications, such negative effects can be overcome by specific adjustments of conditions.

For example, when DNA elution from AXpH beads, which are specific magnetic silica beads bearing polyethyleneimine groups available from QIAGEN, Germany, was performed with 1% polyacrylic acid as an example of a polyanionic compound, it completely inhibited PCR when the eluates comprised $1/10^{th}$ of the PCR volume. However, PCR efficiency was completely restored when $MgCl_2$ concentration was increased from 5 mM to 11 mM. Accordingly, in certain embodiments, after isolation, the isolated nucleic acid can be amplified in the presence of $Mg^{2+}$ at a concentration of about 10 to about 40 mM. The polyanionic compounds may be used at varying concentrations necessary to elute the nucleic acid. For example, the concentration may advantageously be 0.1% to about 2.0% and in certain embodiments, the concentration is from about 0.5% to about 1.0%. It is understood that any numerical value recited herein includes all values from the lower value to the upper value (and including the lower value and the upper value). For example, all possible combinations of numerical values between the lowest value and the highest value enumerated are to be considered expressly stated in this application. For example, for a concentration range stated as 0.025% to about 2.5%, it is intended that values such as 0.05, 0.2, 0.3, 0.4, 1.8, 1.9, etc. or any ranges within this range such as 0.3 to 1.0 or 0.4 to 2.4, etc., are expressly enumerated in this specification. These low concentrations have little or no effect on subsequent detection/analysis steps such as amplification or enzymatic reactions. Thus, the eluate can be used directly in such downstream reactions without neutralization (which is typically required when using pH based elution) and/or without using a desalting step (when using a salt buffer based elution).

By way of example, PAA elutes DNA from anion-exchange magnetic beads at concentrations that do not significantly affect PCR or isothermal amplification such as tHDA (thermophilic Helicase Dependent Amplification). The concentration of PAA is typically, but not limited to, from 0.025-2.5%. In one embodiment, PAA is present at a concentration of from 0.1% to 2.0%. In another embodiment, and more preferably 0.5-1.0%), and the exact concentration depends also on the volume of the sample that is included into the PCR. For example, higher PAA concentrations provide better nucleic acid recovery from AXpH beads but tend to somewhat slow down amplification. Thus, if higher PAA concentrations are used for elution, then it may be preferable to dilute the sample in downstream reactions or use the sample in a larger overall total volume in downstream reactions. As an example, if DNA was eluted by 1% PAA, this may lead to unsatisfactory results when 8 μL of such eluates are loaded per 25 μL PCR reaction. However, the same eluates will yield the expected results if either the volumes of eluates are smaller (e.g., 2 μL of such eluate per 25 μL PCR) or total PCR volumes are higher (e.g., 8 μL of the eluate is loaded into 100 μL PCR reaction). Thus, PAA concentration in the elution buffer, sample volume per PCR and the volumes of individual PCR should be found experimentally as a reasonable compromise between required assay sensitivity and limitations of PCR volume. Alternatively, concentrations of polyanionic compounds that could be inhibitory to PCR or other nucleic acid amplification techniques can be tolerated if the eluates are used in applications that do not require amplification; for example, in nucleic acid hybridization techniques. Thus, eluates can be used directly for nucleic acid detection.

According to one embodiment, the elution is performed at elevated temperatures such as e.g. at temperatures $\geq 50°$ C., $\geq 60°$ C. or even $\geq 70°$ C.

The present disclosure also provides methods for nucleic acid isolation, analysis and in particular amplification that allow automation utilizing an anion exchange material that is suitable for the gentle isolation of DNA as well as RNA. Further, the eluted DNA or RNA does not generally need additional handling steps such as a neutralization step or desalting step in order to be fully compatible with downstream reactions.

Eluates, Analysis, and Amplification Compositions

One advantage of the isolation and elution methods disclosed herein is that an eluate comprising the nucleic acid of interest can be generated without resorting to pH switch or high salt methods. As such, the eluates generated according to the methods described herein may be used directly in various analytical methods, including, for example, amplification procedures such as PCR, RT-PCR, helicase-dependent amplification, hybrid capture assays, sequencing or transfection. In case the eluted nucleic acid is used in amplification procedures, any anionic compound comprising at least two anionic groups as defined herein can be used. However, in certain embodiments including a subsequent amplification reaction, in particular a PCR, the anionic compound is not dextran sulfate.

Thus, in one aspect, an eluate obtained according to any of the above-described methods is provided. In one embodiment, the eluate is directly compatible with a subsequent enzymatic reaction. By "directly compatible," it is meant that the resulting eluate does not require any further processing steps (such as desalting, neutralization, et cetera) before it may be included in an enzymatic reaction mixture. In another embodiment, the eluate is obtained by a method comprising: a) providing a nucleic acid-anion exchange complex; and b) adding a composition comprising an anionic compound comprising at least two anionic groups to the nucleic acid-anion exchange complex, wherein the anionic compound displaces the nucleic acid from the anion exchange material, and further wherein the composition comprising the anionic compound further comprises amplification components. By way of example and not limitation, said amplification components may be: an enzyme having a polymerase activity; an enzyme having a reverse transcriptase activity; an enzyme having a helicase activity; nucleotides; primer nucleic acids; amplification buffers; a nick-inducing agent; a source of $Mg^{2+}$ and/or $Mn^{2+}$, for example, $MgCl_2$ and/or $MnCl_2$; a ribonucleotide triphosphate (NTP); a deoxyribonucleotide triphosphate (dNTP); a source of $K^+$, for example, KCl; a source of $NH_4^+$, for example, $(NH_4)_2SO_4$; or a reducing agent, for example, 2-mercapthoethanol and/or dithiothreitol (DTT).

In another aspect, a method of analyzing a nucleic acid is provided, said method comprising, consisting essentially of, or consisting of: a) providing a nucleic acid-anion exchange complex; b) adding a composition comprising an anionic compound comprising at least two anionic groups to the nucleic acid-anion exchange complex; and c) analyzing the nucleic acid in the presence of the anionic compound.

In one embodiment, the analysis method comprises a nucleic acid amplification. Nucleic acid amplifications can be broadly separated into two categories: temperature cycled amplifications and isothermic amplifications. Either class of amplification may be used. The amplification in the disclosed methods can be either a temperature cycled amplification or an isothermic amplification. Exemplary methods of amplification include, but are not limited to, polymerase chain reaction ("PCR"), reverse transcriptase ("RT") reaction, thermophilic helicase-dependent amplification ("tHDA"), whole genome amplification, and ligase chain reaction ("LCR"). Exemplary analytical methods comprising an amplification step include, but are not limited to, PCR, RT-PCR, real time PCR, real time RT-PCR, quantitative real time PCR, quantitative real time RT-PCR, multiplex analysis, melting curve analysis, high resolution melting curve analysis, tHDA, RT-tHDA, real time tHDA, quantitative real time tHDA, quantitative real time RT-tHDA, NIA, RT-NIA, real time NIA, quantitative real time NIA, and quantitative real time RT-NIA.

In temperature cycled amplifications, such as PCR, the temperature typically is raised above the melting point of the target nucleic acid to "melt" any double stranded portions, and then lowered to a point at which oligonucleotide primers anneal with single stranded portion of the target nucleic acid, then raised again to a temperature at which the primers remain annealed and the polymerase is active.

In isothermic amplifications, such as tHDA and whole genome amplification, an agent is added to the reaction mixture to permit amplification without temperature cycling. For example, in tHDA, an enzyme having helicase activity is added to the amplification mixture. As used herein, "helicase" or "an enzyme with, or having, helicase activity" refers to any enzyme capable of unwinding a double stranded nucleic acid. The helicase functions to unwind double stranded nucleic acids, thus obviating the need for repeated melting cycles. Exemplary helicases include *E. coli* helicase I, II, III, & IV, Rep, DnaB, PriA, PcrA, T4 Gp41 helicase, T4 Dda helicase, T7 Gp4 helicases, SV40 Large T antigen, yeast RAD. Additional helicases that may be useful include RecQ helicase, thermostable UvrD helicases from *T. tengcongensis* and *T. thermophilus*, thermostable DnaB helicase from *T. aquaticus*, and MCM helicase from archaeal and eukaryotic organisms. As another example, in nick-initiated amplification ("NIA"), a nick-inducing agent is used to induce breaks in the phosphodiester bonds of the nucleic acid backbone. A polymerase having strand displacement activity can then initiate amplification at the site of the nick, using one strand of the nucleic acid as a primer and the other strand as a template. As used herein, "nick-inducing agent" refers to any enzymatic or chemical reagent or physical treatment that introduces breaks in the phosphodiester bond between two adjacent nucleotides in one strand of a double-stranded nucleic acid. Examples of nick-inducing enzymes include Bpu10 I, BstNB I, Alw I, BbvC I, BbvC I, Bsm I, BsrD, and *E. coli* endonuclease I.

Analysis in the Presence of an Anion Exchange Material

Anion exchange materials are know to interfere with interfere with the analysis of nucleic acids. Separate and apart from their utility as elution agents, the anionic compounds as described throughout also have the unexpected property of permitting analysis of nucleic acids in the presence of anion exchange materials. Accordingly, the present disclosure relates to materials and methods of analyzing nucleic acids in the presence of anion exchange materials, wherein a anionic compound is added during the analysis step.

In one embodiment, a method of analyzing a nucleic acid of interest in the presence of an anion exchange material is disclosed, said method comprising: a) purifying the nucleic acid of interest from a sample using the anion exchange material; and b) analyzing the nucleic acid in a first solution comprising at least one anionic compound, wherein the anionic compound comprises at least two anionic groups. In one embodiment, the anionic compound is non-polymeric. In another embodiment, the anionic compound is a polyanionic compound.

In another embodiment, the purifying step comprises the steps of: (1) contacting a sample comprising the nucleic acid with the anion exchange material, (2) forming a nucleic acid-anion exchange complex between the anion exchange material and the nucleic acid, and (3) isolating the nucleic acid-anion exchange complex from the sample.

In a further aspect, the purifying step comprises the steps of: (1) contacting a sample comprising the nucleic acid with the anion exchange material, (2) forming a complex between the anion exchange material and the nucleic acid, (3) isolating the complex from the sample, and (4) washing the complex to remove impurities. The wash conditions may be selected such that substantially all non-nucleic acid material is removed. The wash conditions further may be refined such that specific nucleic acids are removed as impurities as well.

In another embodiment, the nucleic acid is eluted from the nucleic acid-anion exchange complex before the anionic compound is added. For example, the nucleic acid may be eluted using pH switch or high salt solutions. In such a case, the resulting eluant will likely need to be further processed before it can be used in an analytical process. As another example, the nucleic acid may be eluted using a solution comprising an anionic compound, as described above. The eluate may then be separated from a substantial portion of the anion exchange material before an analysis (as in bead carryover), or the eluate may be analyzed in the presence of the entire portion of the In another embodiment, an analytical solution comprising the anionic compound is added directly to the nucleic acid-anion exchange complex. By way of example and not limitation, where the analysis method is an amplification, a nucleic acid amplification composition comprising an anionic compound comprising at least two anionic groups may be added directly to the nucleic acid-anion exchange complex.

As used herein, the term "nucleic acid amplification composition" shall refer to any composition comprising an anionic compound as described above and further having the appropriate components and physical properties such that a nucleic acid amplification may be conducted therein. Such components may include in the appropriate circumstance, but are not limited to: buffers; salt solutions; primers; nucleotide triphosphates; macromolecules such as RNase, RNase inhibitors, coenzymes, and/or catalysts; polyethylene glycol; sorbitol; and DMSO. Physical properties include, but are not limited to, pH, ionic strength, and $Mg^{2+}$ concentration. The precise identity of the additional components and physical properties will depend on numerous factors, including but not limited to: the particular amplification method being used; the identity of the nucleic acid being amplified; the length and G/C content of the desired amplicon; and the particular polymerase and/or helicase being used. These additional components and physical properties will be immediately apparent to the person having skill in the art. By way of example and not limitation, said amplification components may be any combination of: an enzyme having a polymerase activity; an enzyme having a reverse transcriptase activity; an enzyme having a helicase activity; nucleotides; primer nucleic acids; amplification buffers; a nick-inducing agent; a source of $Mg^{2+}$ and/or $Mn^{2+}$, for example, $MgCl_2$ and/or $MnCl_2$; a ribonucleotide triphosphate (NTP); a deoxyribonucleotide triphosphate (dNTP); a source of $K^+$, for example, KCl; a source of $NH_4^+$, for example, $(NH_4)_2SO_4$; or a reducing agent, for example, 2-mercapthoethanol and/or dithiothreitol (DTT).

The nucleic acid amplification composition may be provided at a working (1×) concentration or in a concentrated format. By way of example and not limitation, concentrated formats may be provided as aqueous solutions at 5×, 10×, 20×, or 50× concentrations, or as lyophilized concentrates.

In one embodiment, the nucleic acid amplification composition comprises a) at least one target nucleic acid; b) an anion exchange material; c) at least one anionic compound comprising at least two anionic groups; and d) at least one protein having a polymerase activity.

Another embodiment relates to a nucleic acid amplification composition comprising a) at least one target nucleic acid; b) an anion exchange material; c) at least one anionic compound comprising at least two anionic groups; d) at least one protein having a polymerase activity; and e) at least one protein having a helicase activity.

Such materials and methods are particularly suitable for use in automated methods.

Kits

The present disclosure also provides a kit for isolating nucleic acid from a sample such as a biological sample, the kit comprising an anion exchange material, preferably an anion exchange material as described above; and an elution buffer comprising at least one anionic compound comprising at least two anionic groups as described above. The kit may further comprise one or more components selected from the group consisting of washing buffers, loading buffers, equilibration buffers, lysis buffers (e.g. for lysing the sample such as a cell or tissue sample), nucleases such as RNases and/or DNases, RNase or DNase inhibitors, and instructions for its use. The kit for isolating nucleic acid may also comprise further components suitable for analyzing and/or amplifying the isolated nucleic acid.

Furthermore, the present disclosure also provides a kit for amplifying nucleic acid, the kit comprising an enzyme having a polymerase activity and at least one anionic compound comprising at least two anionic groups, preferably a non-polymeric anionic compound as described above. The kit may further comprise one or more additional components such as an enzyme having a reverse transcriptase activity; an enzyme having a helicase activity; nucleotides; primer nucleic acids; amplification buffers; a nick-inducing agent; a source of $Mg^{2+}$ and/or $Mn^{2+}$, for example, $MgCl_2$ and/or $MnCl_2$; a ribonucleotide triphosphate (NTP); a deoxyribonucleotide triphosphate (dNTP); a source of $K^+$, for example, KCl; a source of $NH_4^+$, for example, $(NH_4)_2SO_4$; a reducing agent, for example, 2-mercapthoethanol and/or dithiothreitol (DTT) and instructions for its use. The kit for amplifying nucleic acid may further contain any of the components of the kit for isolating nucleic acid.

The various components of the kits disclosed herein may be provided at a working (1×) concentration or in a concentrated format. By way of example and not limitation, concentrated formats may be provided as aqueous solutions at 5×, 10×, 20×, or 50× concentrations, or as lyophilized concentrates.

Use

The present disclosure also provides the use of an anionic compound comprising at least two anionic groups, preferably a non-polymeric compound comprising at least two anionic groups, for displacing a nucleic acid reversibly bound to an anion-exchange material from said anion-exchange material. The anionic compound, the non-polymeric compound, the nucleic acid and/or the anion-exchange material are preferably as described above.

The present disclosure also provides a method of isolating a nucleic acid from a sample containing a nucleic acid. The method comprises the step of: a) contacting the sample comprising the nucleic acid with an anion-exchange material to allow binding of the nucleic acid. The anion-exchange material is capable of reversibly binding the nucleic acid. The method further comprises the steps of: b) optionally washing the anion-exchange material to remove unbound sample components; and c) eluting the bound nucleic acid by adding at least one compound comprising at least two anionic groups, wherein the anionic compound(s) is capable of displacing the nucleic acids from the anion-exchange material.

Details with respect to the compound comprising at least two anionic groups and the anion exchange material and the method are discussed in detail above. It is referred to the above disclosure.

As discussed above, the present disclosure also provides a method of analyzing, preferably amplifying a nucleic acid in the presence of an anion exchange material, said method comprising the steps of complexing the nucleic acid with the anion exchange material to form a nucleic acid-anion exchange complex; optionally separating the nucleic acid-anion exchange complex from other material; and analyzing, preferably amplifying the nucleic acid in a solution comprising at least one compound comprising at least two anionic groups. The anionic compound preferably does not inhibit or interfere with the amplifying reaction, respectively analysis step. Furthermore, the anionic compound preferably reduces or removes any inhibitory effect the anion exchange material has on the amplifying reaction or analysis step. That is, the anion exchange material, when present, may reduce the efficacy of the analysis, in particular the amplification step. This reduction in efficacy is at least partially neutralized by the presence of the anionic compound used according to the invention.

As discussed above, also provided is a method of isolating a nucleic acid from a sample comprising a nucleic acid, said method comprising:
  a) contacting the sample with an anion-exchange material, wherein the anion-exchange material reversibly binds nucleic acid;
  b) optionally washing the anion-exchange material to remove unbound sample components; and
  c) eluting bound nucleic acid by adding at least one non-polymeric compound comprising at least two anionic groups, wherein the compound displaces the bound nucleic acid from the anion-exchange material to obtain an isolated nucleic acid.

According to one embodiment, the anion-exchange material comprises a solid phase that is modified with a positively ionizable capture moiety. The positively ionizable capture moiety may have one or more of the following characteristics:
  a) it is selected from the group consisting of primary, secondary or tertiary amins having the formula $R_3N$, $R_2NH$, $RNH_2$ and/or $X—(CH_2)_n—Y$ wherein
    X is $R_2N$, RNH or $NH_2$,
    Y is $R_2N$, RNH or $NH_2$,
    R is independently of each other a linear, branched or cyclic alkyl, alkenyl, alkynyl or aryl substituent which may comprise one or more heteroatoms, preferably selected from O, N, S and P, and
    n is an integer in the range of from 0 to 20, preferably 0 to 18, and/or
  b) it is selected from the group consisting of aminomethyl, aminoethyl, diethylaminoethyl, trimethylamino, triethylaminoethyl, spermine, spermidine, 3-(propylamino)propylamine, polyamidoamine dendrimers, polyethylenimine, N-morpholinoethyl, and polylysine, and/or
  c) it is selected from the group consisting of spermine, spermidine and polyethylenimine.

The non-polymeric compound may have one or more of the following characteristics:
  a) it comprises at least 2 anionic groups, and preferably between 3 and 6 anionic groups;
  b) it is an organic compound, preferably having from 2 to 20 carbon atoms, more preferably having from 2 to 12 carbon atoms;
  c) it is a carboxylic acids such as oxalic acid, fumaric acid, glutaric acid, maleic acid, malic acid, malonic acid, succinic acid, glutaric acid, adipic acid, pimelic acid, suberic acid, azelaic acid, tartronic acid, tartaric acid, citric acid, isocitric acid, citraconic acid, mesaconic acid, itaconic acid, aconitic acid, propane-1,2,3-tricarboxylic acid, aconitic acid, butane-1,2,3,4-tetracarboxylic acid, triethyl-1,1,2-ethanetricarboxylic acid, cyclopropane dicarboxylic acid, cyclobutane dicarboxylic acid, cyclobutane tricarboxylic acid, cyclopentane dicarboxylic acid, cyclohexane dicarboxylic acid, cyclohexane tricarboxylic acid, cyclohexane tetracarboxylic acid, cyclohexane hexacarboxylic acid, cyclooctane dicarboxylic acid, phthalic acid, isophthalic acid, terephthalic acid, hemimellitic acid, trimellitic acid, trimesic acid, mellophanic acid, prehnitic acid, pyromellitic acid, benzene pentacarboxylic acid, and mellitic acid, hexacarboxylic acid of dierythritol, octaacetic acid of trierythritol, iminodiacetic acid, nitrilotriacetic acid, ethylenediamine tetraacetic acid, diethylenetriamine pentaacetic acid, α-ketoglutaric acid, glutamic acid, aspartic acid, dicarboxymalonic acid, (18-crown-6)-2,3,11,12-tetracarboxylic acid, oligomers of 2 to 10, preferably 2 to 6, polymerizable or condensable acidic monomers such as acrylic acid, methacrylic acid or vinylacetic acid, which are optionally substituted by one or more substituents;
  d) it is a organosulfonic acid such as methyl disulfonic acid, ethyl disulfonic acid, benzene disulfonic acid, phenole disulfonic acid, and naphthalene disulfonic acid, which are optionally substituted by one or more substituents;
  e) it is a organophosphonic acid, such as hydroxyethane diphosphonic acid;
  f) it is an organophosphate; and/or
  g) it is carbonate or diacetylacetone.

As described above, anion-exchange material magnetic beads, preferably magnetic silica beads or magnetic polymer beads, can be used that are functionalized with positively ionizable capture moieties and wherein as said non-polymeric compound a carboxylic acid selected from oxalic acid, mellitic acid, pyromellitic acid and citric acid can be used.

The elution step of said method may have one or more of the following characteristics:
  a) the pH during elution does not lie above the pKa of the positively ionizable groups of the capture moiety;
  b) the pH during elution is in a range from 5 to 13, preferably 5 to 8.5;
  c) the total salt concentration during solution does not exceed 1M, preferably 0.5M.

The method may further comprise the step of amplifying the isolated nucleic acid, preferably without performing intermediate purification, buffering or desalting steps.

As discussed above, also provided is a method of analyzing, preferably amplifying a nucleic acid in the presence of an anion exchange material, said method comprising:
  a) complexing the nucleic acid with the anion exchange material to form a nucleic acid-anion exchange complex;
  b) separating the nucleic acid-anion exchange complex from other material; and
  c) analyzing, preferably amplifying the nucleic acid in a solution comprising at least one non-polymeric compound comprising at least two anionic groups.

The analysis step may comprise PCR, RT-PCR, quantitative real time PCR, quantitative real time RT-PCR, multiplex analysis, melting curve analysis, high resolution melting curve analysis, tHDA, RT-tHDA, quantitative real time tHDA or quantitative real time RT-tHDA, or a combination thereof.

According to one embodiment of said method, the nucleic acid is not eluted from the anion exchange material prior to the analysis step.

According to one embodiment, the anion exchange material as defined above and/or a non-polymeric compound as described above is used.

Also provided is a kit for isolating a nucleic acid from a sample, the kit comprising:
a) an anion exchange material; and
b) an elution buffer comprising at least one non-polymeric compound comprising at least two anionic groups.

According to one embodiment, the anion exchange material as defined above and/or a non-polymeric compound as described above is used.

EXAMPLES

I. Materials

1. Anionic Exchange Modification of Magnetic Silica Gel

In a 100 ml one-necked flask with two-necked cap are provided 23 ml deionised water, 3 ml 250 mM $NaPO_4$, pH 6.0, 100 µl 3-glycidoxypropyl-trimethoxysilane and 91.7 µl diethylaminopropyl-triethoxysilane. The solution is adjusted to pH 5.50 with 2 M NaOH. Before add-on, 2 g MagAttract Beads "G" are put in a nalgene-flask with 15 ml deionised water, shaken for 5 minutes on a shaker at level 5, magnetically separated (3 minutes) and the supernatant water is drained. The suspension is refilled up to total 7 g and added into the reaction flask. The nalgene-flask is washed once with 1 ml deionised water. Then, the flask is added to a KPG-stirrer and a reflux condenser. Stirring rate is 500/min. The temperature of the suspension is raised up to 90° C. using an oil bath (heater without magnet). 90° C. is hold for 4 h. Afterwards, the oil bath is removed and the suspension is stirred 1 h to cool down. The flask volume is converted into a 60 ml nalgene-flask and the stirrer is washed with a little deionised water. To convert the rest of the beads, the suspension in the nalgene-flask is magnetically separated for 3 minutes and the flask is washed once with the liquid. The beads are separated with a magnet at the bottle neck and the fluid is drained. For washing the following amount of liquid is added to the beads; the suspension is shaken for 5 minutes at the shaker at level 5, then, the beads are separated with a magnet at the bottle neck and the fluid is drained. Washing was done with 2×25 ml Tris/NaCl-buffer, 1×25 ml deionised water and 3×25 ethanol. Subsequently, to convert into water, washing with 3×25 ml deionised-water was performed.

2. Synthesis of "Base-Free" Nucleic Acid

Dissolve under cover gas 530 mg (2.2 mmol) 2-cyanoethyl-N,N-diisopropylchlorophosphoramidite in 15 ml dichloromethane and parallel in a 100 ml three-necked-flask 146 µl (154 mg, 2 mmol) 1,3-propanediol in water-free dichloromethane. Put the solutions together in the three-necked-flask and let them react for 3 hours. Then, 16 ml "activator-solution" (0.25 M 4,5-Dicyanoimidazole in $CH_3CN$) is added, shaken for 1 h by room temperature, then, add 4 ml "Oxidizer Solution" (1 M iodine in $H_2O$/Pyridin/THF, 2:21:77 v/v/v) and react overnight. After bleaching, add several iodine balls till the yellow stain does not disappear anymore. Afterwards, put the flask into a fridge. If no precipitate is shown, add once more 50 ml hexane and then condense because no precipitate has shown. Then, the residue is washed twice with 40 ml hexane, decant and resuspend in 50 ml RNase free water. Dialyse against 5 l 50 mM $NaH_2PO_4$, pH 7.0 and twice against 5 l VE-water with a dialyse tube (MWCO 5,000). Afterwards the solvent is removed with freeze-drying. The yield of this experiment was 40 mg.

3. Synthesis of Amino Functional Magnetic Carboxylate Beads

Resuspend 500 mg of magnetic particles (Carboxyl-Adembeads, Ademtech, order no. 02111) in 10 ml 50 mM MES buffer, pH 6.1 and add 11.5 ml of a 50 mg/ml solution of N-hydroxysulfosuccinimide. Mix with a mini shaker. Add 10 ml of a 52 µmol/l solution of 1-ethyl-3-(3-dimethylaminopropyl)carbodiimide and mix again. Afterwards, it is reacted for 30 minutes on a rotating shaker. Then, the supernatant is removed. Resuspend in 50 ml 50 mM MES buffer, pH 6.1 and make 10 ml aliquots thereof. After magnetic separation the supernatants are removed. Then, resuspend in 1 ml 50 mM MES buffer, pH 6.1 and add 2 ml of the amine in a concentration of 500 mg/ml in 50 mM MES and a pH of 8.5, mix well. After 10 minutes ultrasound treatment it is reacted for 1 h on a rotating shaker. Afterwards wash twice with 10 ml 50 mM MES buffer, pH 6.1, separate magnetically and discard the supernatant. Resuspend the particles in 2 ml MES-buffer with a pH from 4.5 to 7.0.

4. Synthesis of with Polyethylenimine Modified Magnetic Carboxylate Beads

Resuspend 500 mg of magnetic particles (Estapor) in 10 ml 50 mM MES buffer, pH 6.1 and add 11.5 ml of a 50 mg/ml solution of 1-ethyl-3-(3-dimethylaminopropyl)carbodiimide and mix again. Afterwards, it is reacted for 30 minutes on a rotating shaker. Then, the supernatant is removed. Resuspend in 50 ml 50 mM MES buffer, pH 6.1 and make 10 ml aliquots thereof. After magnetic separation the supernatants are removed. Then, resuspend in 1 ml 50 mM MES buffer, pH 6.1 add 2 ml of polyethylenimine in a concentration of 500 mg/ml in 50 mM MES and a pH of 8.5, mix well. After 10 minutes ultrasound treatment it is reacted for 1 h on the rotating shaker. Afterwards wash twice with 10 ml 200 mM NaCl, 50 mM MES buffer, pH 7.0 as well as four times with 10 ml 50 mM MES buffer, pH 6.1. After magnetic separation, the supernatants are removed. The particles are resuspended in 2 ml MES buffer with a pH from 4.5 to 7.0.

II. Working Examples

Example 1

Nucleic Acid Elution Using a Secondary Nucleic Acid and Magnetic Anion Exchange Silica Particles 1 µg of a DNA fragment of 300 bp are dissolved in 100 µl buffer (25 mM MES, pH 7.0). Then, 1 mg of a magnetic silica gel prepared according to Example 1.1 are added and incubated at RT and 1,000 rpm. After magnetic separation, the supernatant is discarded. Then the beads are washed twice by incubation in 100 µl deionised water at 1,000 rpm on the thermal shaker for 5 min, magnetic separation and discarding of the supernatant. 50 µl elution buffer containing 1-3 µg of a 500 bp DNA fragment are added to the beads, and after 5 min incubation on the thermal shaker and magnetic separation the supernatant is obtained. Then the elution is repeated using 50 µl elution buffer containing 50 mM Tris, 50 mM NaCl, pH 8.5.

Figure 1:
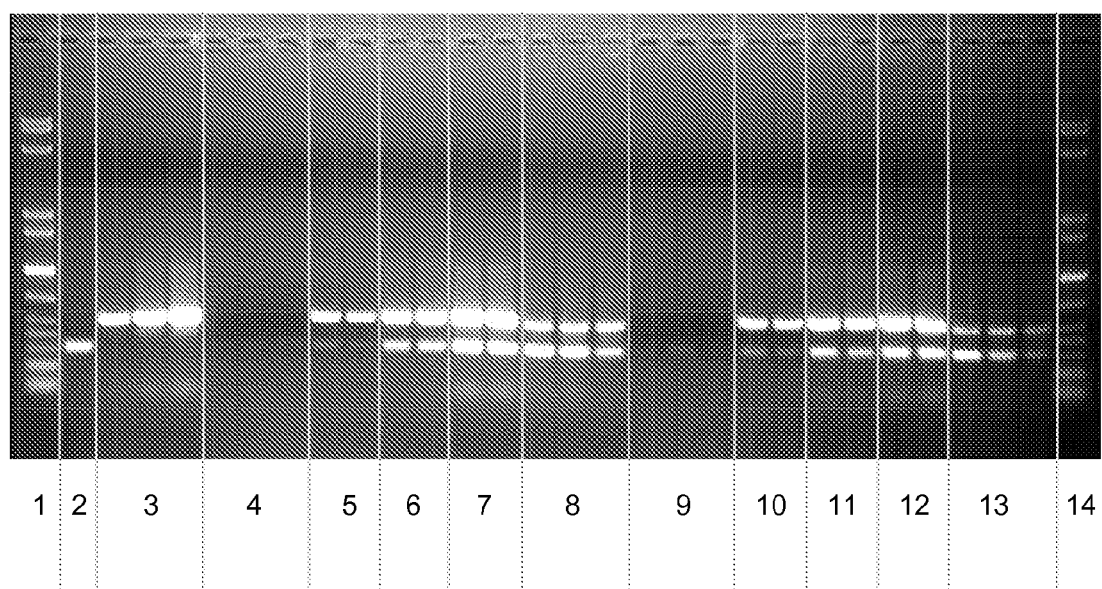
FIG. 1 shows a gel-electrophoretic analysis of the bound and eluted nucleic acids. A 300 bp DNA fragment was bound onto diethylaminopropyl magnetic beads and eluted using a 500 bp DNA fragment. The gels are loaded as follows.

FIG. 1 shows that there is no DNA in the remaining sample and that the entire DNA was bound by the magnetic particles. In the eluates with 1, 2 or 3 µg secondary DNA and pH 7 DNA fragments of 300 bp and 500 bp are visible, showing that the secondary DNA (500 bp) has displaced at least part of the bound first DNA (300 bp). In the second eluate at pH 8.5 the remaining DNA fragments were eluted.

Example 2

Nucleic Acid Elution with Different Anionic Compounds and Slightly Alkaline Buffers 2 µg plasmid DNA (pUC21) are solved in 25 mM MES, pH 8.0 or 8.5 and 0.25 mg magnetic particles coated with polyethylenimine (50 mg/ml in deionised water) are added. The dispersion is mixed for 5 min at RT and 1,000 rpm. After magnetic separation, the supernatant is removed. Then, the beads are washed twice by incubation in 100 µl deionised water at RT and 1,000 rpm on the thermal shaker for 5 min, magnetic separation and discarding of the supernatant. Elution is performed using 100 µl elution buffer (25 mM MES, pH 8.0 or 8.5) additionally containing 2,000 ng dextransulfate (Mw 9,000-25,000), polyacrylic acid, oxalic acid or mellitic acid. Then, a second elution is performed using 50 µl 50 mM MES, 50 mM NaCl, pH 8.5.

FIG. 2 shows that using 2,000 ng dextransulfate, polyacrylic acid, oxalic acid or mellitic acid most of the pDNA is eluted from the magnetic particles. The second elution at pH 8.5 only elutes remainders of the plasmid.

Example 3

Elution Using Carboxylic Acids

2 µg plasmid DNA (pUC21) are solved in 25 mM MES, pH 7.0 and 0.125 mg magnetic particles coated with spermine (50 mg/ml in deionised water) are added. Then, the dispersion is incubated for 5 min at RT and 1,000 rpm. After magnetic separation the supernatant is removed. Then, the beads are washed twice by incubation in 100 µl deionised water at RT and 1,000 rpm on the thermal shaker for 5 min, magnetic separation and discarding of the supernatant. Elution is performed using 100 µl elution buffer (25 mM MES, pH 7.0) additionally containing 2,000, 5,000 or 10,000 ng of carboxymethyldextrane, dextransulfate (Mw 6,500-10,000), dextransulate (Mw 9,000-25,000), polyacrylic acid, poly(4-styrenesulfonate maleic acid), acetic acid, oxalic acid, citric acid, pyromellitic acid or mellitic acid. Then, a second elution is performed using 50 µl 50 mM MES, 50 mM NaCL, pH 8.5.

FIG. 3 shows that using 2,000-10,000 ng dextransulfate, polyacrylic acid, poly(4-styrenesulfonate maleic acid), oxalic acid, citric acid, pyromellitic acid, or mellitic acid, elution of the bound nucleic acid is achieved. Acetic acid eluted only low amounts of plasmid. Here, the majority of the plasmid is eluted in the second elution step. The other compounds, however, are capable of eluting the bound nucleic acid.

Example 4

Elution Using "Base-Free" Nucleic Acid

2 µg plasmid DNA (pUC21) are solved in 25 mM MES, pH 7.0 and 0.25 mg magnetic particles coated with spermine (pH 7.0, 7.5) or polyethylenimine (pH 8.0, 8.5), respectively, (each 50 mg/ml in deionised water) are added. Then, the dispersion is mixed for 5 min at RT and 1,000 rpm. After magnetic separation, the supernatants are removed. Then, the beads are washed twice by incubation in 100 µl deionised water at RT and 1,000 rpm on the thermal shaker for 5 min, magnetic separation and removal of the supernatant. Elution is performed with 100 µl elution buffer (25 mM MES, pH 7.0, 7.5, 8.0, or 8.5) additionally comprising 2,000, 5,000 or 10,000 ng "base-free" DNA. Then, a second elution is performed using 50 µl 50 mM MES, 50 mM NaCl, pH 8.5.

FIG. 4 shows binding of the plasmid DNA to the solid phase since no DNA could be detected in the remaining sample. At pH 7.0 and 7.5 it is not possible to remove the DNA from the spermine beads. However, at pH 8.0 and 8.5 the plasmid is eluted from the polyethylenimine beads.

Example 5

PCR Inhibition by Different Anions

To a β-actin PCR reaction mixture 5, 10 or 20 ng genomic DNA and 20 ng each of acetic acid, oxalic acid, citric acid, polyacrylic acid or mellitic acid are added. In parallel the PCR results without addition of a carboxylic acid as control and a blank value are determined.

The results of the inhibition tests (FIG. 5) show that PCR performs well in the presence of any of the tested carboxylic acids. In particular, the addition of acetic acid, oxalic acid or citric acid does not influence the PCR at all. Addition of polyacrylic acid and mellitic acid likewise do not inhibit PCR in these examples, although a mild increase of the ct-value is detectable. As is shown in the subsequent examples, however, polyacrylic acid can under some conditions inhibit PCR. The inhibitory effects of e.g. polyacrylic acid can be reversed/rescued by increasing the $Mg^{2+}$ concentration as demonstrated at FIG. 24.

Example 6

PCR Inhibition Assay Using Citric Acid

To a β-actin PCR reaction mixture 5 or 10 ng genomic DNA and 30, 60, 120 or 240 ng citric acid are added. In parallel, the PCR results without addition of the carboxylic acid as control and a blank value are determined. Then, the β-actin PCR is performed and the Ct-values are determined. The Ct-value represents the number of reaction cycles of the PCR until the amount of the produced nucleic acid exceeds a certain threshold level (which is used to distinguish between the signal of the nucleic acid product and background signals).

As shown in FIG. 6 the Ct-value even decreases with increasing amount of citric acid. One possible explanation for this is that the citric acid complexes cationic components of the PCR buffer and thereby increases specificity of the PCR reaction. No inhibitory influence of the citric acid could be detected when adding up to 360 ng to 5 ng gDNA.

Example 7

DNA Binding and Release Using a Secondary DNA

1 µg DNA fragment (100 bp) is solved in 100 µl 25 mM MES buffer, pH 7.0. 15 µl of a suspension of spermine-modified magnetic particles (26.4 mg/ml) are added and the suspension is mixed for 5 min at RT and 1,000 rpm. After magnetic separation, the supernatant is removed. Then, the particles are washed twice by incubation in 100 µl deionised water at RT and 1,000 rpm for 5 min, magnetic separation and removal of the supernatant. Then, the primary DNA is eluted using 50 µl elution buffer (25 mM MES, pH 7.0) containing 1, 2 or 3 µg DNA of 500 bp or 1000 bp. Elution is performed by incubation in the elution buffer for 5 min at RT and 1,000 rpm, magnetic separation and obtaining of the supernatant. Samples of the supernatants after binding, washing and elution are then electrophoretically separated on an agarose gel.

FIG. 7 shows that the shorter primary DNA is bound to the magnetic particles and effectively eluted by the longer secondary DNA.

Example 8

DNA Binding and Release Using a Secondary DNA Having a Shorter Length

1 µg DNA fragment of 500 bp or 1000 bp is solved in 100 µl 25 mM MES buffer, pH 7.0. 15 µl of a suspension of spermine-modified magnetic particles (17 mg/ml) are added and the suspension is mixed for 5 min at RT and 1,000 rpm bound to spermine-modified magnetic particles. After magnetic separation, the supernatant is removed. Then, the particles are washed twice by incubation in 100 µl deionised water at RT and 1,000 rpm for 5 min, magnetic separation and removal of the supernatant. Then, elution is performed using 50 µl elution buffer (25 mM MES, pH 7.0) containing 1, 2 or 3 µg DNA of 200 bp. Elution is performed by incubation in the elution buffer for 5 min at RT and 1,000 rpm, magnetic separation and obtaining of the supernatant. For control, a second elution using 50 µl 50 mM Tris, 50 mM NaCl, pH 8.5 is performed. Samples of the supernatants after binding, washing, first and second elution are then electrophoretically separated on an agarose gel.

FIG. 8 shows that also a longer primary DNA can effectively be eluted using a shorter secondary DNA. The subsequent control elution only shows low amounts of residual primary DNA.

Example 9

DNA Binding and Release Using RNA for Elution 0.125 mg spermine-modified beads are suspended in 100 µl 25 mM MES buffer, pH 7.0 and 1 µg of a DNA fragment of 500 bp is added. The suspension is incubated for 5 min at RT and 1,000 rpm, magnetically separated and the supernatant is removed. Then, the beads are washed twice by incubation in 100 µl deionised water for 5 min, magnetic separation and removal of the supernatant. Then, elution is performed using 50 µl elution buffer (25 mM MES, pH 7.0) containing 1, 2 or 3 µg RNA. Elution is performed by incubation in the elution buffer for 5 min, magnetic separation and obtaining of the supernatant. For control, a second elution using 50 µl 50 mM Tris, 50 mM NaCl, pH 8.5 is performed. Samples of the supernatants after binding, washing, first and second elution are then electrophoretically separated on an agarose gel.

FIG. 9 shows that significant amounts of the bound DNA are eluted using 3 µg RNA.

Example 10

RNA Binding and Release Using DNA for Elution 0.125 mg spermine-modified beads are suspended in 100 µl 25 mM MES buffer, pH 7.0 and 2 µg RNA are added. The suspension is incubated for 5 min at RT and 1,000 rpm, magnetically separated and the supernatant is removed. Then, the beads are washed twice by incubation in 100 µl deionised water for 5 min, magnetic separation and removal of the supernatant. Then, elution is performed using 50 µl elution buffer (25 mM MES, pH 7.0) containing 1, 2 or 3 µg DNA of 500 bp. Elution is performed by incubation in the elution buffer for 5 min, magnetic separation and obtaining of the supernatant. For control, a second elution using 50 µl 50 mM Tris, 50 mM NaCl, pH 8.5 is performed. Samples of the supernatants after binding, washing, first and second elution are then electrophoretically separated on an agarose gel.

FIG. 10 shows that the bound RNA is eluted from the beads using DNA. Using 3 µg DNA, nearly the entire bound RNA is eluted.

Example 11

Genomic DNA Binding and Release Using Plasmid DNA for Elution 0.125 mg or 0.25 mg spermine-modified beads are suspended in 100 µl 25 mM MES buffer, pH 7.0 and 1 µg genomic DNA is added. The suspension is incubated for 5 min at RT and 1,000 rpm, magnetically separated and the supernatant is removed. Then, the beads are washed twice by incubation in 100 µl deionised water for 5 min, magnetic separation and removal of the supernatant. Then, elution is performed using 50 µl elution buffer (12.5 mM MES, pH 7.0) containing 1, 2 or 3 µg plasmid DNA. Elution is performed by incubation in the elution buffer for 5 min, magnetic separation and obtaining of the supernatant. For control, a second elution using 50 µl 50 mM Tris, 50 mM NaCl, pH 8.5 is performed. Samples of the supernatants after binding, washing, first and second elution are then electrophoretically separated on an agarose gel.

FIG. 11 shows elution of the genomic DNA when 3 µg plasmid DNA are used.

Example 12

Plasmid DNA Binding and Release Using Genomic DNA for Elution 0.25 mg spermine-modified beads are suspended in 100 µl 25 mM MES buffer, pH 7.0 and 1 µg plasmid DNA (pUC21) is added. The suspension is incubated for 5 min at RT and 1,000 rpm, magnetically separated and the supernatant is removed. Then, the beads are washed twice by incubation in 100 µl deionised water for 5 min, magnetic separation and removal of the supernatant. Then, elution is performed using 50 µl elution buffer (12.5 mM MES, pH 7.0) containing 1, 2 or 3 µg genomic DNA. Elution is performed by incubation in the elution buffer for 5 min, magnetic separation and obtaining of the supernatant. For control, a second elution using 50 µl 50 mM Tris, 50 mM NaCl, pH 8.5 is performed. Samples of the supernatants after binding, washing, first and second elution are then electrophoretically separated on an agarose gel.

FIG. 12 shows that plasmid DNA can effectively be eluted using genomic DNA. The subsequent control elution only shows low amounts of residual plasmid DNA.

Example 13 siRNA Binding and Release Using a Short DNA Fragment for Elution 0.125 mg polyethylenimine-modified beads prepared according to example 1.4 are suspended in 100 µl 25 mM MES buffer, pH 8.0 and 1 µg siRNA (Qiagen, ordering no. SI00300650) is added. The suspension is incubated for 5 min at RT and 1,000 rpm, magnetically separated and the supernatant is removed. Then, the beads are washed twice by incubation in 100 µl deionised water for 5 min, magnetic separation and removal of the supernatant. Then, elution is performed using 50 µl elution buffer (25 mM MES, pH 8.0) containing 2 or 3 µg DNA of 300 bp. Elution is performed by incubation in the elution buffer for 5 min, magnetic separation and obtaining of the supernatant. For control, a second elution using 50 µl 50 mM Tris, 50 mM NaCl, pH 8.5 is performed. Samples of the supernatants after binding, washing, first and second elution are then electrophoretically separated on an agarose gel.

FIG. 13 shows that the bound siRNA is effectively eluted using the short DNA fragment. The subsequent control elution only shows low amounts of residual RNA.

Example 14

Analysis of Inhibitory Effects of Plasmid DNA on a PCR Using Genomic DNA

For analyzing the influence of the plasmid DNA used for elution on a PCR using the primary DNA, a serial assay of β-actin PCRs with different amounts of genomic DNA and added plasmid DNA is performed. For the PCR, an Applied Biosystems 7500 Real-Time PCR system (Applied Biosystems, Foster City, Calif., USA), TaqMan β-Actin Control Reagents (PE Applied Biosystems, ordering no. 401846), a QuantiTect Probe PCRMastermix (nucleotides, polymerases and salts; Qiagen, ordering no. 127 137 815) and the fluorescence dye FAM (from the β-Actin Control Reagents) are used. The genomic DNA is obtained from a nucleic acid preparation from human blood using the kit QIAamp Blood (Qiagen, ordering no. 51106), and the plasmid DNA (pUC21) is prepared by plasmid isolation from *E. coli* using the Qiagen Plasmid Mega Kit (Qiagen, ordering no. 12183). The amounts of genomic DNA and plasmid DNA used as well as the recorded Ct-values are shown in Table 1.

TABLE 1

| genomic DNA (ng) | plasmid DNA (ng) | Ct value |
|---|---|---|
| 2 | 0 | 29 |
| 2 | 10 | 30 |
| 2 | 25 | 30 |
| 2 | 50 | 30 |
| 2 | 100 | 28 |
| 2 | 250 | 30 |
| 2 | 500 | 33 |
| 2 | 1000 | 35 |
| 2 | 2000 | 40 |
| 10 | 0 | 26 |
| 10 | 10 | 27 |
| 10 | 25 | 28 |
| 10 | 50 | 27 |
| 10 | 100 | 27 |
| 10 | 250 | 29 |
| 10 | 500 | 30 |
| 10 | 1000 | 33 |
| 10 | 2000 | 37 |
| 20 | 0 | 26 |
| 20 | 10 | 25 |
| 20 | 25 | 27 |
| 20 | 50 | 26 |
| 20 | 100 | 26 |
| 20 | 250 | 27 |
| 20 | 500 | 28 |
| 20 | 1000 | 36 |
| 20 | 2000 | 38 |

An inhibitory effect—indicated by a higher Ct-value—is only seen when using a very high excess of plasmid DNA. As shown in the other examples, only an excess of up to 5-fold of the secondary nucleic acid is necessary for efficient elution of the bound nucleic acid, while an inhibitory effect of the secondary nucleic acid could only be detected at a 25-fold excess or more. Therefore, under the conditions used herein the use of a secondary nucleic acid to elute a first nucleic acid off from an anion exchange material does not interfere with a subsequent PCR reaction.

Example 15

Elution Using Polyacrylic Acid (PAA)

Figure 14A:
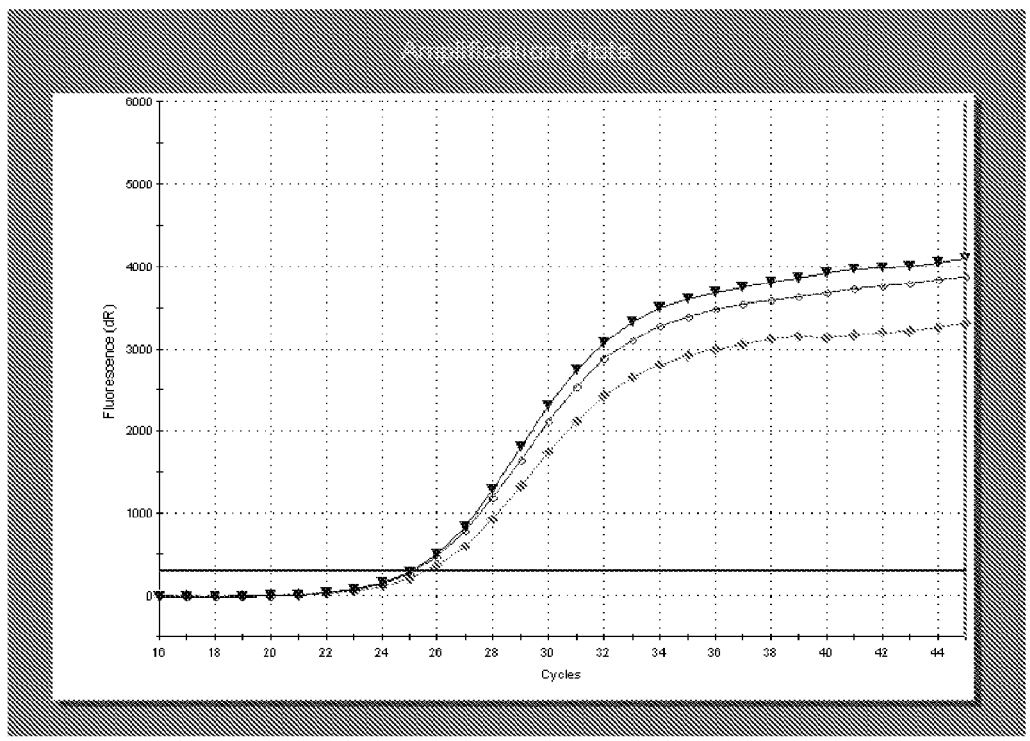
Figure 14A:
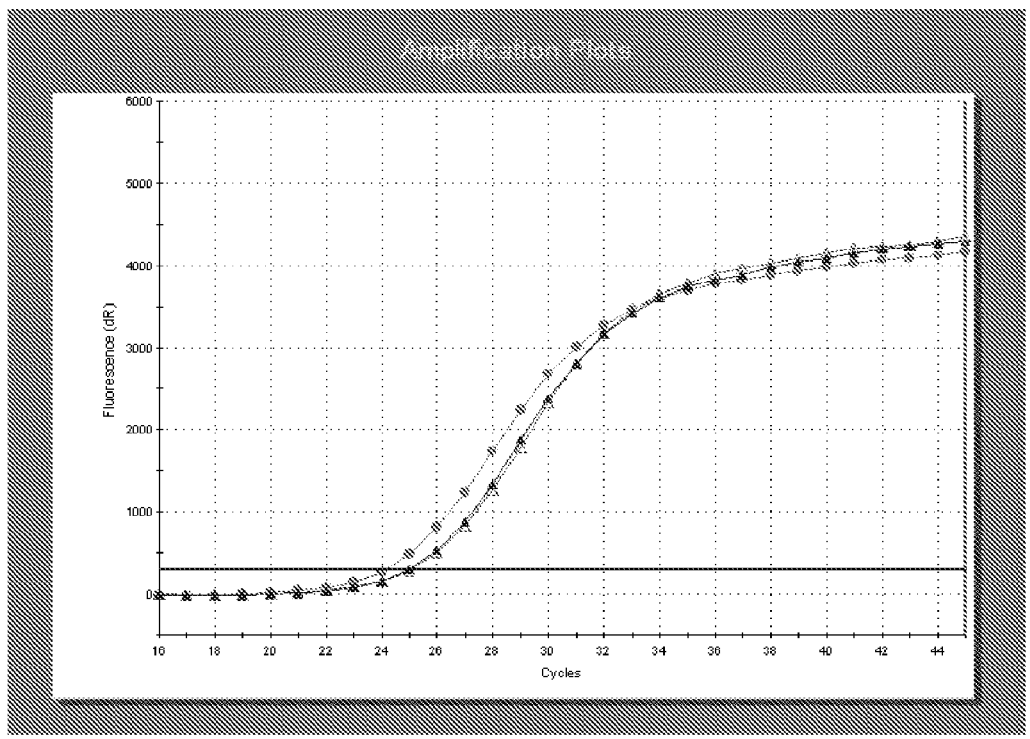
Figure 14B:
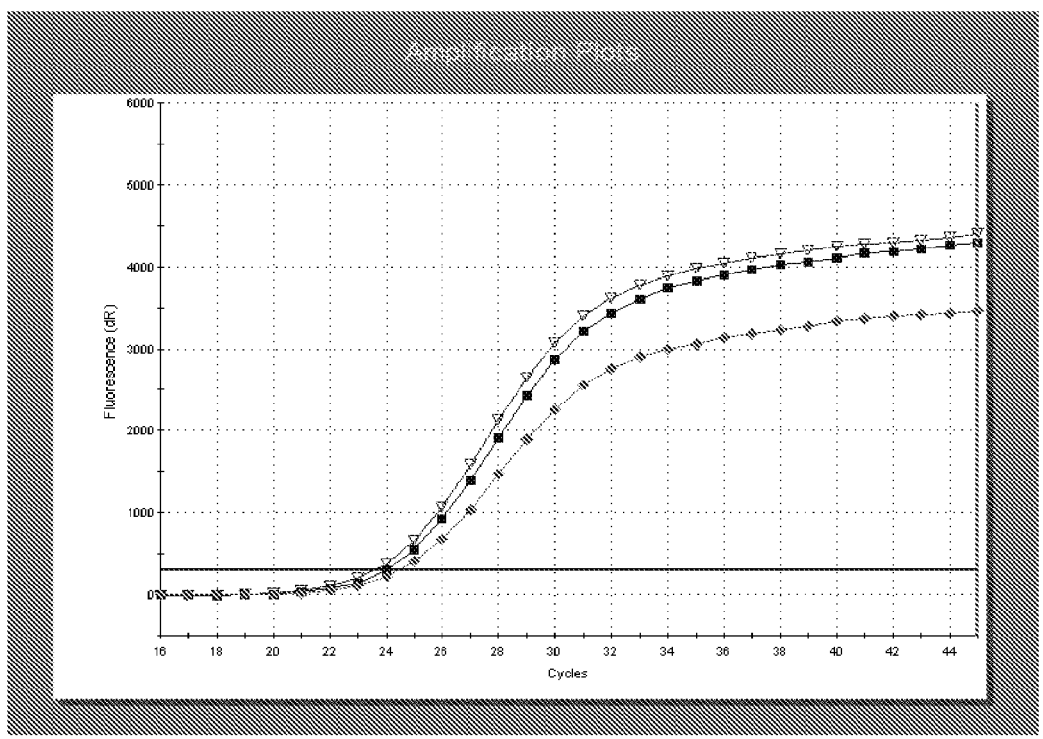
Figure 14B:
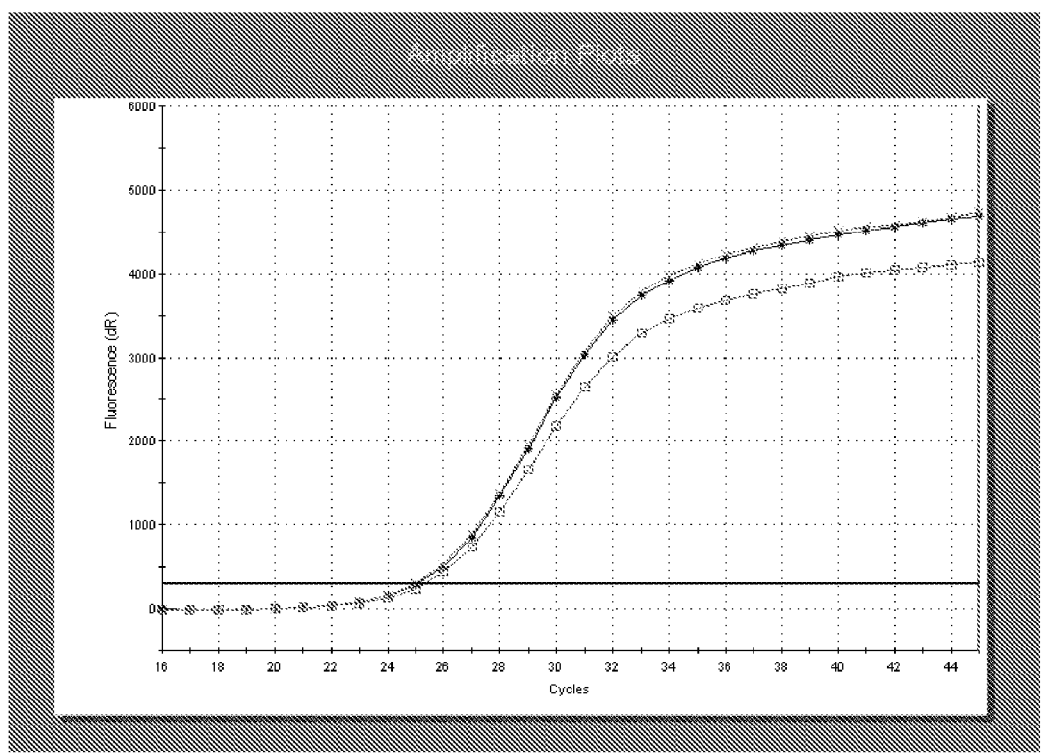
Figure 14C:
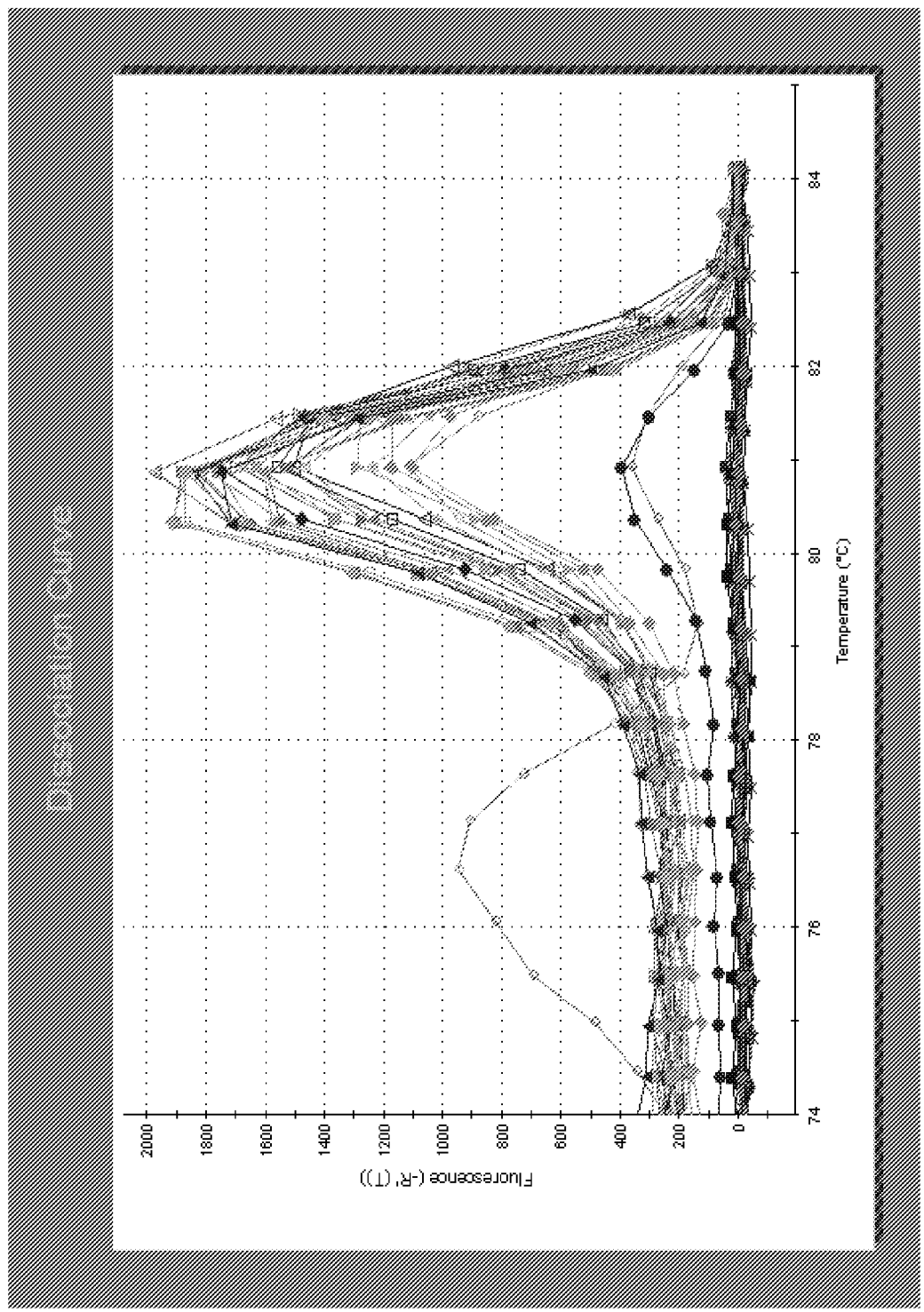

DNA samples containing $5\times10^5$ copies of *Neisseria gonorrhoeae* (NG) DNA were added to 1 mL PreserCyt® media. 0.5 mL of Lysis buffer (2% Triton X-100, 0.2 M EDTA, 40 mM Sodium Citrate, 40 mM Boric acid in 100 mM Tris HCl, pH 7.0) was then added, bringing the pH of the sample to ~7.8. The sample was then mixed with 30 µL of an AXpH™ bead suspension and incubated at 60° C. for 10 minutes. The AXpH™ beads were magnetically separated and washed once with 500 µl of wash buffer (0.1% NP-40 in 0.1 mM Tris, pH8.0). Elution was then conducted by adding either: (a) 25 µL of wash buffer or (b) solutions of PAA, Na salt (Fw>200,000; pH adjusted to 8.0 with Tris base) in wash buffer. The eluates (2.5 µL samples) were then compared in real-time PCR performed in triplicate 25 µL reactions for each eluate to an equivalent amount of control DNA in the same elution buffer that had not been processed according to the procedure described above. Thus, control dilutions of DNA would mimic a 100% recovery of DNA from the beads and also reveal if PAA has any negative effect on PCR. The threshold cycles (Ct) were detected using a TaqMan-MGB probe (TET channel, see FIGS. 14A-14C). To confirm product identity, EvaGreen fluorescent dye was also added to the PCR to record post-PCR melting curves (FIG. 14C).

Results are summarized in Table 2. The "Eluate" column shows the results of using the indicated buffer to elute the nucleic acid from AXpH™ beads. The "Control" column shows the results of diluting the nucleic acid directly in the indicated buffer composition. "ΔCt rec." is calculated by subtracting the average of the "Control" column replicates from the average of the "Eluate" column replicates for each buffer composition. "ΔCt eff." is calculated by subtracting the average of the "Control" column replicates for each buffer from the average of the "Control" column replicates for the Wash Buffer. Thus, "ΔCt rec." reflects the efficiency of DNA elution from AXpH™ beads, and "ΔCt eff." shows any potential loss in PCR efficiency caused by the presence of PAA in the amplification reaction. Ideally, both parameters should be close to zero, reflecting high efficiency recovery and no inhibition of the PCR reaction.

Data in Table 2 demonstrate that recovery of DNA from AXpH™ beads in PAA elution is close to 100%. The pH of both wash buffer and elution buffers with PAA was identical at pH 8.0, which rules out any pH effects in DNA elution. FIGS. 14A-14C show that amplification curves in PCR are normal and PAA does not promote artifact formation in PCR.

TABLE 2

| | Channel | Eluate (Ct) | | | | Control (Ct) | | | | ΔCt (rec.) | ΔCt eff. |
| --- | --- | --- | --- | --- | --- | --- | --- | --- | --- | --- | --- |
| | | 1 | 2 | 3 | Avg. | 1 | 2 | 3 | Avg. | | |
| Wash buffer | tet | No Ct | 39.4 | 38.9 | 39.1 | 22.7 | 22.4 | 23.0 | 22.7 | 16.4 | 0.0 |
| | FAM | No Ct | 40.4 | 37.6 | 39.0 | 23.8 | 23.7 | 24.1 | 23.9 | 15.2 | 0.0 |
| 0.025% PAA | tet | 28.4 | 29.1 | 28.2 | 28.6 | 22.8 | 22.7 | 22.8 | 22.7 | 5.9 | 0.0 |
| | FAM | 29.1 | 29.5 | 28.9 | 29.2 | 23.6 | 23.5 | 23.5 | 23.5 | 5.7 | −0.3 |
| 0.05% PAA | tet | 25.8 | 27.7 | 26.1 | 26.9 | 23.3 | 34.0 | 23.0 | 26.7 | 0.2 | 4.0 |
| | FAM | 26.5 | 27.9 | 26.7 | 27.3 | 24.0 | 33.0 | 23.6 | 26.9 | 0.5 | 3.0 |
| 0.1% PAA | tet | 25.7 | 25.2 | 25.1 | 25.1 | 25.1 | 24.1 | 25.0 | 24.7 | 0.4 | 2.0 |
| | FAM | 25.9 | 25.6 | 25.5 | 25.5 | 25.7 | 24.5 | 25.2 | 25.1 | 0.4 | 1.3 |
| 0.125% PAA | tet | 25.1 | 25.4 | 25.0 | 25.2 | 23.6 | 24.0 | 24.5 | 24.0 | 1.2 | 1.3 |
| | FAM | 25.7 | 25.8 | 25.6 | 25.7 | 24.2 | 24.3 | 24.7 | 24.4 | 1.3 | 0.5 |

Example 16

Comparison of Elution of DNA with PAA to "pH-Shift" Elution

The experiment was performed essentially as Example 15 with the following differences: (a) each set of 3 samples contained $10^5$, $10^3$ and 10 copies of NG DNA; (b) one set of samples was eluted with 25 µL of 0.5% PAA; (c) one set of samples was eluted with an alkaline solution (15 µL of 0.1 M NaOH, with subsequent neutralization with 10 µL of 170 mM Tris HCl, pH 8.0); and (d) a control set of NG DNA was prepared to simulate 100% recovery of samples from AXpH™ beads by diluting the appropriate amount of NG DNA in wash buffer. As shown in FIG. 15, results for the elution by alkali and PAA are comparable.

Example 17

Elution with Different PAA Size Fractions, Polymethacrylic Acid, and Polyglutamic Acid This experiment demonstrated that DNA is eluted by two different samples of polyacrylic acid (PAA—heavy "PAAH" and PAA—light "PAAL") and polymethacrylic acid (PMA) but not by the wash buffer from AXpH™ beads. Each DNA sample contained 5×10⁵ copies of *Neisseria gonorrhoeae* (NG) DNA in 1 mL PreserCyt® media. After adding 0.5 mL of Lysis buffer (2% Triton X-100, 0.2 M EDTA, 40 mM Sodium Citrate, 40 mM Boric acid in 100 mM Tris HCl, pH 7.0); the final pH of the sample was ~7.8), the sample was mixed with 30 µL of AXpH™ bead suspension and incubated at 60° C. for 10 minutes. The AXpH™ beads were magnetically separated and washed once with 500 µl of wash buffer (0.1% NP-40 in 0.1 mM Tris, pH8.0). Elution was then conducted by adding either: (a) 25 µL of wash buffer; (b) 0.25% PAAH (polyacrylic acid, Na salt, Fw>200,000) in wash buffer; (c) 0.1% PAAL (polyacrylic acid, Na salt, Fw~5,100) in wash buffer; (d) 0.1% PMA (polymethacrylic acid, Na salt, Fw~483,000) in wash buffer. The eluates (2 µL samples) were then compared in real-time PCR performed in triplicate 25 µL reactions for each eluate to an equivalent amount of control DNA that had not been processed according to the procedure described above. The threshold cycles (Ct) were detected using EvaGreen fluorescent dye. The average Ct's were 27.2 (PAAH), 24.4 (PAAL), 26.1 (PMA) and 23.5 (control DNA), respectively. Wash buffer eluate gave no amplification products. These results show that the elution of *Neisseria gonorrhoeae* (NG) DNA was caused not by "pH-shift" but by the presence of PAA and PMA.

Additionally, this experiment demonstrated that PAA of lower formula weight, PMA, and polyglutamic acid ("PGA") also eluted DNA from AXpH™ beads. Each DNA sample contained 5 µl of $10^5$ copies of NG DNA in PreserCyt® media. Lysis buffer (as described in Example 15) was added, the sample vortexed and incubated at 60° C. for 10 minutes. Each sample was shaken once after 5 minutes. The AXpH™ beads were magnetically separated, the supernatant aspirated and washed with 500 µl of wash buffer (as described in Example 15) followed by separation of the beads and aspiration of the wash buffer. Elution was then conducted by adding either: a) wash buffer; b) alkaline solution; c) wash buffer containing PAAH; d) wash buffer containing PAAL; e) wash buffer containing PMA; or f) wash buffer containing PGA. As seen in Table 3, wash buffer control demonstrated good washing off of the DNA in a single step. Alkali wash buffer was ineffective. PAAH gave very good recovery. PAAL worked even better than PAAH. PMA provided recovery results as good as PAAL but efficiency was somewhat lower.

TABLE 3

| | Dye | Eluates | | | | Ct | | | | ΔCt rec. | ΔCt eff. |
| --- | --- | --- | --- | --- | --- | --- | --- | --- | --- | --- | --- |
| | | 1 | 2 | 3 | Avg | 1 | 2 | 3 | Avg | | |
| Wash Buffer | Tet | 43.67 | N/A | N/A | N/A | 23.6 | 23.5 | 23.5 | 23.5 | N/A | 0.0 |
| | FAM | 43.72 | N/A | N/A | N/A | 23.6 | 23.5 | 23.4 | 23.5 | N/A | 0.0 |
| Alkali | Tet | N/A | N/A | N/A | N/A | 23.5 | 23.6 | 23.7 | 23.6 | N/A | 0.1 |
| | FAM | N/A | N/A | N/A | N/A | 23.8 | 23.8 | 24 | 23.8 | N/A | 0.3 |
| 0.25% PAA-H | Tet | 28.1 | 28.8 | 28.2 | 28.5 | 26.6 | 27.2 | 27.3 | 27.0 | 1.5 | 3.5 |
| | FAM | 27.0 | 27.4 | 27.0 | 27.2 | 25.8 | 26.3 | 26.3 | 26.1 | 1.1 | 2.6 |
| 0.1% PAA-L | Tet | 24.9 | 24.9 | 25.0 | 24.9 | 24.0 | 23.9 | 24.0 | 24.0 | 0.9 | 0.5 |
| | FAM | 24.5 | 24.4 | 24.5 | 24.4 | 24.1 | 23.9 | 23.9 | 23.9 | 0.5 | 0.4 |
| 0.1% PMA | Tet | 26.3 | 26.6 | 26.5 | 26.6 | 24.0 | 24.0 | 23.8 | 23.9 | 2.6 | .4 |
| | FAM | 25.9 | 26.1 | 26.0 | 26.1 | 24.3 | 24.1 | 23.9 | 24.1 | 1.9 | 0.6 |

TABLE 3-continued

| | | Eluates | | | | Ct | | | | ΔCt | ΔCt |
|---|---|---|---|---|---|---|---|---|---|---|---|
| | Dye | 1 | 2 | 3 | Avg | 1 | 2 | 3 | Avg | rec. | eff. |
| 0.1% | Tet | 35.0 | 34.4 | 34.5 | 34.4 | 23.4 | 23.2 | 23.5 | 23.4 | 11.1 | −0.1 |
| PGA | FAM | 34.9 | 34.1 | 34.2 | 34.1 | 23.5 | 23.2 | 23.4 | 23.4 | 10.8 | −0.1 |

Example 17

Elution of RNA with PAA

This example demonstrates that RNA also can be eluted from AXpH™ beads by polyacrylic acid. The RNA used in this example was a 7,983 nt transcript of cloned HPV16 sequence. 25 µL of the RNA solution ($7.5 \times 10^4$ copies/4) in 1 mL PresevCyt media were added to the suspension of 60 µL Qiagen AXpH™ beads in 1 mL Lysis Buffer (as described in Example 15), and incubated at 60° C. and washed as described in Example 15. After the wash step, the beads were re-suspended in 500 µL Wash Buffer and divided in 2×250 µL. After magnetic separation of the beads, one portion was eluted with 25 µL of 0.5% PAA (>200,000) containing 0.1% NP-40 for 10 min at 60 C; the other portion of beads was eluted with 2.5% PAA containing 0.1% NP-40 under the same conditions. After separating the beads, the eluate from the $1^{st}$ portion was loaded directly into reverse transcription/PCR while the eluate from the $2^{nd}$ portion was diluted 5-fold with water. In both cases 2.5 µL eluate volumes were added into 25 µL one-step reverse transcription-PCR reactions using Qiagen 1-Step QuantiTech Virus Kit, containing the primers and TaqMan® probe for the HPV16 6467-6590 region. RNA controls were prepared by diluting the RNA solution with the corresponding elution buffers appropriately, to mimic 100% elution of RNA from the AXpH™ beads (i.e., 10- and 50-fold dilution of the $7.5 \times 10^4$ copies/4 RNA stock solution for the 0.5% and 2.5% PAA eluates, respectively). The one-step RT/PCR was performed in triplicates for each eluate/control according to the manufacturer's protocol. Results are shown in Table 4. The resulting difference in Ct's between control dilutions and eluates is within the experimental error, suggesting that RNA elution was close to 100%.

TABLE 4

| | | Ct (dR) | | | | |
|---|---|---|---|---|---|---|
| Eluate | Set | 1 | 2 | 3 | Average Ct | ΔCt |
| 0.5% PAA | Control | 24.66 | 24.45 | 25.04 | 24.7 | 0.0 |
| | Eluate | 24.1 | 23.63 | 23.85 | 23.9 | −0.8 |
| 2.5% PAA | Control | 27.44 | 27.4 | 27.67 | 27.5 | 0.0 |
| | Eluate | 25.78 | 25.76 | 25.65 | 25.7 | −1.8 |

Example 18

Effect of Anion Exchange Materials on PCR and Reversal by Polyanionic Compounds

It has been anecdotally observed that anion exchange materials can interfere with effective amplification of purified nucleic acids. To demonstrate this effect, real time PCR was performed in the absence of AXpH beads or in the presence of a 1:10,000, 1:1,000, or 1:100 dilution of AXpH beads. Results are shown at FIG. 16. Inhibition is shown by a shift of the linear phase of the amplification curve to the right.

Carrier DNA was tested to determine if it could reverse this inhibitory effect. Bovine serum albumin ("BSA") was tested as a control. Real time PCR amplifications were performed in triplicate in the presence of 1:50 dilutions of AXpH™ beads and either 1 mg/ml BSA (at dilutions of 1:1 and 1:10 for final concentrations of 0.1 and 0.01 mg/ml BSA) or 100 ng/ml carrier DNA. Fluorescent signals were generated using reporter probes labeled with either FAM (top curve) or 5'-Tetrachloro-Fluorescein ("TET") dye (lower curve). Results are shown at FIG. 17 and FIG. 18.

Polyacrylic acid was then tested to determine whether this effect was specific for nucleic acids or if it could be replicated with other polyanionic compounds. Real time PCR amplifications were performed in triplicate in the presence of 1:200, 1:250; 1:400; and 1:500 dilutions of AXpH beads in the presence ("PAA+") or absence ("PAA−") of 25 ng/ml PAA. Fluorescent signals were generated using reporter probes labeled with either FAM (top curve) or 5'-Tetrachloro-Fluorescein dye ("TET") (lower curve). As can be seen at FIG. 18, polyacrylic acid was similarly able to reverse PCR inhibition by anion exchange materials. Results are shown at FIG. 19.

In addition, PAA was tested over a range of target concentrations to determine if this effect holds for low target concentration in the presence of high anion exchange concentrations. Real time PCR amplifications were performed in triplicate on 10, $10^3$, and $10^5$ copies of a target nucleic acid in the presence of a 1:25 dilution of AXpH beads and 0 or 25 ng/mL PAA. Fluorescent signals were generated using reporter probes labeled with either FAM (top curve) or 5'-Tetrachloro-Fluorescein dye ("TET") (lower curve). Results are shown at FIG. 20.

Example 19

Effect of Anion Exchange Materials on tHDA and Reversal by Polyanionic Compounds Although PCR is the most commonly used method of amplifying nucleic acids, other methods are known. In order to determine if the effect is specific for PCR, tHDA amplification was performed in the presence of anion exchange material either with or without polacrylic acid.

As can be seen at FIG. 21, the presence of polyacrylic acid rescues amplification using tHDA at both low and high target nucleic acid concentrations. Thus, polyanionic compounds are effective at rescuing amplifications using either PCR or tHDA.

Example 20

Amplification of Nucleic Acids in the Presence of Anion Exchange Materials

Nucleic acids commonly are eluted and separated from anion exchange materials before analysis, owing to the inhibitory effect of the anion exchange materials. It would be advantageous, however, to be able to analyze the nucleic acid without having to separate it from the beads. Therefore, anionic compounds as disclosed herein were tested to determine if they permit real time PCR amplification of nucleic acids in the presence of the anion exchange material.

In one example, three different polyanionic compounds were tested in a real time PCR: polyacrylic acid, polymethacrylic acid, and polyglutamic acid. Target NG DNA was added to AXpH beads, vortexed, and incubated for 10 minutes. The beads were then magnetically separated from the supernatant and washed with wash buffer (10 mM Tris, pH 8; 0.1% NP-40 alternative) by vortexing. The bead were magnetically separated from the wash buffer and resuspended by vortexing the beads in either wash buffer or wash buffer plus 0.25% of the respective polyanionic compound. A portion of these suspensions were then added to plate wells for analysis. Results are shown at FIG. 22.

As another example, polyglutamic acid ("PGA") was compared to polyadenylate ("poly-A") and carboxymethyl dextran ("CMD"). This analysis was performed substantially as above, except 1.25% of PGA, poly-A, or CMD was used where appropriate. Results are shown at FIG. 23.

Example 22

Effect of Polyanionic Compound on PCR and Reversal by $Mg^{2+}$

PAA inhibits PCR, which can be corrected by increasing the concentration of $Mg^{2+}$. Target NG DNAs were amplified in the presence of either 0.05 or 0.1% PAA in the presence of two types of anion exchange materials and 3, 7, or 11 mM $Mg^{2+}$. As can be seen in the figure, increasing the concentration of $Mg^{2+}$ reversed the inhibitory effect of PAA. Results are shown at FIG. 24.

The invention claimed is:

1. A method of eluting a nucleic acid from an anion exchange material to form an eluate, said method comprising:
    a) providing a nucleic acid-anion exchange complex; and
    b) eluting the nucleic acid from the nucleic acid-anion exchange complex, wherein said eluting comprises addition of an elution buffer comprising an anionic compound to the nucleic acid-anion exchange complex, wherein said anionic compound comprises at least two anionic groups,
wherein said anionic compound disrupts the nucleic acid-anion exchange complex, and
wherein said nucleic acid-anion exchange complex is provided by a method comprising:
    i) providing a sample comprising a nucleic acid; and
    ii) adding the sample to an anion exchange material under pH and salt conditions at which the anion exchange material reversibly complexes with the nucleic acid,
wherein the elution buffer has a pH and salt concentration that does not exceed the pH and salt conditions at which the nucleic acid-anion exchange complex is formed,
wherein said nucleic acid-anion exchange complex is formed at a pH of 7 or greater and
wherein said nucleic acid-anion exchange complex is not exposed to a pH of less than 7 prior to said eluting of step (b).

2. The method of claim 1, wherein the anionic compound is present in the elution buffer at a concentration sufficient to disrupt the nucleic acid-anion exchange complex, and wherein the elution buffer possesses a pH such that, in the absence of the anionic compound, the nucleic acid-anion exchange complex would not be disrupted.

3. The method of claim 1 wherein the anion exchange material comprises a positively ionizable capture moiety selected from the group consisting of:
    a) An amine of the formula $R_3N$;
    b) An amine of the formula $R_2NH$;
    c) An amine of the formula $RNH_2$; and
    d) An amine of the formula $X-(CH_2)_n-Y$,
wherein:
    X is $R_2N$, RNH or $NH_2$,
    Y is $R_2N$, RNH or $NH_2$,
    R is independently of each other a linear, branched or cyclic alkyl, alkenyl, alkynyl or aryl substituent which may comprise one or more heteroatoms, preferably selected from O, N, S and P, and
    n is an integer in the range of from 0 to 20.

4. The method of claim 1 wherein the anion exchange material comprises a polyethylenimine (PEI)-modified magnetic silica bead.

5. The method of claim 1 wherein the anionic compound is selected from the group consisting of:
    a) a non-polymeric compound selected from the group consisting of: a carboxylic acid, an oligomer of polymerizable or condensable acidic monomers, an organosulfonic acid, an organophosphonic acid, an organophosphate, a carbonate, and a diacetylacetone; and
    b) a polyanionic compound selected from the group consisting of: a polymerized unsaturated carboxylic acid; a copolymer of an unsaturated carboxylic acid and at least one other monomer; a polypeptide of an acidic amino acid; a copolymer of an acidic amino acid with at least one other amino acid; a polycarbohydrate bearing a covalently attached ionizable group selected from the group consisting of carboxylic acid, sulfonic acid, phosphonic acid, phosphate, and carbonate; a polystyrene bearing a covalently attached ionizable group selected from the group consisting of carboxylic acid, sulfonic acid, phosphonic acid, phosphate, and carbonate; a second nucleic acid; and a nucleic acid analog.

6. The method of claim 1 wherein the anionic compound comprises at least three anionic groups.

7. The method of claim 1 wherein the anionic compound is a non-polymeric compound comprising from 2 to 20 carbon atoms.

8. The method of claim 1 wherein the anionic compound is selected from the group consisting of: oxalic acid, mellitic acid, pyromellitic acid, citric acid, polyacrylic acid (PAA), polymethacrylic acid (PMA), polyglutamic acid (PGA), and dextran sulfate (DS).

9. The method of claim 1 wherein the elution buffer has a pH such that, in the absence of the anionic compound, the nucleic acid-anion exchange complex would not be disrupted.

10. The method of claim 1 wherein the elution buffer has a pH that does not exceed the pKa of the positively ionizable groups of the capture moiety.

11. The method of claim 1 wherein the elution buffer has a pH in a range from 7 to 13.

12. The method of claim 1 wherein the elution buffer has a pH in a range from 7 to 8.5.

13. The method of claim 1 wherein the elution buffer has a total salt concentration of approximately 1M or less.

14. The method of claim 1 wherein the elution buffer has a total salt concentration of approximately 0.5M or less.

15. The method of claim 1 wherein the elution buffer has a pH in a range from 8.2 to 9.

16. The method of claim 1 wherein the elution buffer further comprises an enzyme having a polymerase activity and, optionally, a source of $Mg^{2+}$.

17. The method of claim 2, wherein the elution buffer possesses a pH and salt concentration suitable for performing a nucleic acid amplification reaction.

18. The method of claim 2, wherein the elution buffer further comprises an enzyme having a polymerase activity and optionally comprising $Mg^{2+}$ or a source thereof.

* * * * *